US012667463B2

(12) United States Patent
Croll

(10) Patent No.: US 12,667,463 B2
(45) Date of Patent: Jun. 30, 2026

(54) FEMORAL PROSTHESES WITH UPSIZING AND DOWNSIZING CAPABILITIES

(71) Applicant: Zimmer, Inc., Warsaw, IN (US)

(72) Inventor: Vanessa Croll, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1025 days.

(21) Appl. No.: 17/717,898

(22) Filed: Apr. 11, 2022

(65) Prior Publication Data

US 2022/0233321 A1 Jul. 28, 2022

Related U.S. Application Data

(63) Continuation of application No. 16/675,938, filed on Nov. 6, 2019, now Pat. No. 11,324,599, which is a continuation of application No. 15/971,743, filed on May 4, 2018, now Pat. No. 10,500,054.

(60) Provisional application No. 62/505,322, filed on May 12, 2017.

(51) Int. Cl.
*A61F 2/38* (2006.01)
*A61F 2/30* (2006.01)

(52) U.S. Cl.
CPC .......... *A61F 2/3859* (2013.01); *A61F 2/3886* (2013.01); *A61F 2/389* (2013.01); *A61F 2002/30616* (2013.01); *A61F 2002/3863* (2013.01)

(58) Field of Classification Search
None
See application file for complete search history.

(56) References Cited

U.S. PATENT DOCUMENTS

| | | | |
|---|---|---|---|
| 3,774,244 | A | 11/1973 | Walker |
| 4,016,606 | A | 4/1977 | Murray et al. |
| 4,257,129 | A | 3/1981 | Volz |
| 4,301,553 | A | 11/1981 | Noiles |
| 4,340,978 | A | 7/1982 | Buechel et al. |
| 4,501,266 | A | 2/1985 | McDaniel |
| 4,568,348 | A | 2/1986 | Johnson et al. |

(Continued)

FOREIGN PATENT DOCUMENTS

| | | |
|---|---|---|
| AU | 2011343440 B2 | 4/2014 |
| AU | 2011286306 B2 | 10/2014 |

(Continued)

OTHER PUBLICATIONS

Translation of FR2773059 retrieved from espacenet on Jun. 6, 2025 (Year: 2025).*

(Continued)

*Primary Examiner* — Megan Y Wolf
(74) *Attorney, Agent, or Firm* — Schwegman Lundberg & Woessner, P.A.

(57) ABSTRACT

According to one example, a femoral prosthesis system is provided that has a plurality of sizing options using two families of femoral prostheses is disclosed. The second family of femoral prostheses can have a predetermined increase in femoral posterior condylar offset relative to the first family of femoral prosthesis. In one example, the second family of femoral prostheses can have the predetermined increase in the femoral posterior condylar offset while maintaining substantially a same femoral medial-lateral condylar extent relative to a comparably sized one of the first family of femoral prostheses.

15 Claims, 7 Drawing Sheets

~ 302, 304

| CCK | | PERSONA CCK FEMORAL SIZE | | | | | | | | | | | | |
|---|---|---|---|---|---|---|---|---|---|---|---|---|---|---|
| | | 1 | 1+ | 3 | 3+ | 5 | 5+ | 7 | 7+ | 9 | 9+ | 11 | 11+ | 13 |
| PERSONA TIBIAL SIZE | A | 1-1+/AB | | 3-5+/AB | | | | | | | | 352 | | |
| | B | | | | | | | | | | | | | |
| | C | 1-1+/CD | | 3-5+/CD | | | | 7-9+/CD | | | | | | |
| | D | | | | | | | | | | | | | |
| | E | | | 3-5+/EF | | | | 7-9+/EF | | | | 11-11+/EF | | |
| | F | | | | | | | | | | | | | |
| | G | | | | | | | 7-9+/GH | | | | 11-13+/GH | | |
| | H | | | | | | | | | | | | | |
| | J | | | | | | | | | | | | 11-13/J | |

350

(56)                    References Cited

U.S. PATENT DOCUMENTS

| | | | |
|---|---|---|---|
| 4,673,408 A | 6/1987 | Grobbelaar |
| 4,711,639 A | 12/1987 | Grundei |
| 4,714,474 A | 12/1987 | Brooks, Jr. et al. |
| 4,759,767 A | 7/1988 | Lacey |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A | 6/1990 | Fabian et al. |
| 4,944,756 A | 7/1990 | Kenna |
| 4,944,757 A | 7/1990 | Martinez et al. |
| 4,950,298 A | 8/1990 | Gustilo et al. |
| 4,959,071 A | 9/1990 | Brown et al. |
| 4,963,152 A | 10/1990 | Hofmann et al. |
| 4,999,119 A | 3/1991 | Norman et al. |
| 5,007,933 A | 4/1991 | Sidebotham et al. |
| 5,047,057 A | 9/1991 | Lawes |
| 5,047,058 A | 9/1991 | Roberts et al. |
| 5,059,216 A | 10/1991 | Winters |
| 5,061,271 A | 10/1991 | Van Zile |
| 5,071,438 A | 12/1991 | Jones et al. |
| 5,108,442 A | 4/1992 | Smith |
| 5,116,375 A | 5/1992 | Hofmann |
| 5,133,758 A | 7/1992 | Hollister |
| 5,137,536 A | 8/1992 | Koshino |
| 5,147,405 A | 9/1992 | Van Zile |
| 5,171,283 A | 12/1992 | Pappas et al. |
| 5,192,328 A | 3/1993 | Winters |
| 5,194,066 A | 3/1993 | Van Zile |
| 5,197,488 A | 3/1993 | Kovacevic |
| 5,218,021 A | 6/1993 | Clark et al. |
| 5,219,362 A | 6/1993 | Tuke et al. |
| 5,226,915 A | 7/1993 | Bertin |
| 5,236,461 A | 8/1993 | Forte |
| 5,246,459 A | 9/1993 | Elias |
| 5,271,737 A | 12/1993 | Baldwin et al. |
| 5,275,603 A | 1/1994 | Ferrante et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,344,461 A | 9/1994 | Phlipot |
| 5,360,016 A | 11/1994 | Kovacevic |
| 5,364,402 A | 11/1994 | Mumme et al. |
| 5,370,699 A | 12/1994 | Hood et al. |
| 5,370,701 A | 12/1994 | Finn |
| 5,387,239 A | 2/1995 | Bianco et al. |
| 5,387,240 A | 2/1995 | Pottenger et al. |
| 5,391,721 A | 2/1995 | Hanen et al. |
| 5,395,401 A | 3/1995 | Bahler |
| 5,405,396 A | 4/1995 | Heldreth et al. |
| 5,413,604 A | 5/1995 | Hodge |
| 5,413,605 A | 5/1995 | Ashby et al. |
| 5,425,775 A | 6/1995 | Kovacevic et al. |
| 5,445,642 A | 8/1995 | McNulty et al. |
| 5,458,637 A | 10/1995 | Hayes |
| 5,470,354 A | 11/1995 | Hershberger et al. |
| 5,489,311 A | 2/1996 | Cipolletti |
| 5,507,820 A | 4/1996 | Pappas |
| 5,549,688 A | 8/1996 | Ries et al. |
| 5,556,433 A | 9/1996 | Gabriel et al. |
| 5,571,194 A | 11/1996 | Gabriel |
| 5,597,384 A * | 1/1997 | Walker ............... A61F 2/30721 |
| | | 206/459.5 |
| 5,609,639 A | 3/1997 | Walker |
| 5,609,641 A | 3/1997 | Johnson et al. |
| 5,609,643 A | 3/1997 | Colleran et al. |
| 5,609,645 A | 3/1997 | Vinciuerra |
| 5,613,970 A | 3/1997 | Houston et al. |
| 5,616,273 A | 4/1997 | Clark et al. |
| 5,656,785 A | 8/1997 | Trainor et al. |
| 5,658,341 A | 8/1997 | Delfosse |
| 5,658,342 A | 8/1997 | Draganich et al. |
| 5,658,344 A | 8/1997 | Hurlburt |
| 5,683,470 A | 11/1997 | Johnson et al. |
| 5,702,463 A | 12/1997 | Pothier et al. |
| 5,702,464 A | 12/1997 | Lackey et al. |
| 5,702,466 A | 12/1997 | Pappas et al. |
| 5,733,292 A | 3/1998 | Gustilo et al. |
| 5,755,801 A | 5/1998 | Walker et al. |
| 5,755,802 A | 5/1998 | Gerber |
| 5,776,200 A | 7/1998 | Johnson et al. |
| 5,782,925 A | 7/1998 | Collazo et al. |
| 5,824,100 A | 10/1998 | Kester et al. |
| 5,824,102 A | 10/1998 | Buscayret |
| 5,824,103 A | 10/1998 | Williams et al. |
| 5,871,539 A | 2/1999 | Pappas |
| 5,871,541 A | 2/1999 | Gerber |
| 5,871,543 A | 2/1999 | Hofmann |
| 5,871,545 A | 2/1999 | Goodfellow et al. |
| 5,871,546 A | 2/1999 | Colleran et al. |
| 5,879,394 A | 3/1999 | Ashby et al. |
| 5,906,643 A | 5/1999 | Walker |
| 5,911,723 A | 6/1999 | Ashby et al. |
| 5,928,286 A | 7/1999 | Ashby et al. |
| 5,964,808 A | 10/1999 | Blaha et al. |
| 5,968,099 A | 10/1999 | Badorf et al. |
| 5,976,147 A | 11/1999 | LaSalle et al. |
| 6,004,351 A | 12/1999 | Tomita et al. |
| 6,004,352 A | 12/1999 | Buni |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,080,195 A | 6/2000 | Colleran et al. |
| 6,090,144 A | 7/2000 | Letot et al. |
| 6,102,954 A | 8/2000 | Albrektsson et al. |
| 6,102,955 A | 8/2000 | Mendes et al. |
| 6,123,728 A | 9/2000 | Brosnahan et al. |
| 6,123,729 A | 9/2000 | Insall et al. |
| 6,126,692 A | 10/2000 | Robie et al. |
| 6,143,034 A | 11/2000 | Burrows |
| 6,197,064 B1 | 3/2001 | Haines et al. |
| 6,203,576 B1 | 3/2001 | Afriat et al. |
| 6,206,927 B1 | 3/2001 | Fell et al. |
| 6,210,443 B1 | 4/2001 | Marceaux et al. |
| 6,217,618 B1 | 4/2001 | Hileman |
| RE37,277 E | 7/2001 | Baldwin et al. |
| 6,258,127 B1 | 7/2001 | Schmotzer |
| 6,306,172 B1 | 10/2001 | O'Neil et al. |
| 6,325,828 B1 | 12/2001 | Dennis et al. |
| 6,379,388 B1 | 4/2002 | Ensign et al. |
| 6,406,497 B2 | 6/2002 | Takei et al. |
| 6,413,279 B1 | 7/2002 | Metzger et al. |
| 6,428,577 B1 | 8/2002 | Evans |
| 6,436,145 B1 | 8/2002 | Miller |
| 6,485,519 B2 | 11/2002 | Meyers et al. |
| 6,491,726 B2 | 12/2002 | Pappas |
| 6,506,215 B1 | 1/2003 | Letot et al. |
| 6,506,216 B1 | 1/2003 | McCue et al. |
| 6,558,426 B1 | 5/2003 | Masini |
| 6,607,559 B2 | 8/2003 | Ralph et al. |
| 6,623,526 B1 | 9/2003 | Lloyd |
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |
| 6,755,864 B1 | 6/2004 | Brack et al. |
| 6,770,078 B2 | 8/2004 | Bonutti |
| 6,869,448 B2 | 3/2005 | Tuke |
| 6,916,340 B2 | 7/2005 | Metzger et al. |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |

(56)                References Cited

U.S. PATENT DOCUMENTS

| 7,083,652 B2 | 8/2006 | McCue et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,731,755 B2 | 6/2010 | Wyss et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,105,386 B2 | 1/2012 | Perrone, Jr. et al. |
| 8,141,437 B2 | 3/2012 | Amirouche et al. |
| 8,152,853 B2 | 4/2012 | Belcher |
| 8,163,028 B2 | 4/2012 | Metzger et al. |
| 8,187,280 B2 | 5/2012 | May et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,268,006 B2 | 9/2012 | Meyers et al. |
| 8,317,870 B2 | 11/2012 | Wagner et al. |
| 8,328,873 B2 | 12/2012 | Metzger et al. |
| 8,366,782 B2 | 2/2013 | Wright |
| 8,491,589 B2 | 7/2013 | Fisher et al. |
| 8,506,571 B2 | 8/2013 | Chana et al. |
| RE44,476 E | 9/2013 | Meyers et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,617,250 B2 | 12/2013 | Metzger |
| 8,628,580 B2 | 1/2014 | Sanford et al. |
| 8,690,954 B2 | 4/2014 | Parisi et al. |
| 8,740,984 B2 | 6/2014 | Hartdegen et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,795,282 B2 | 8/2014 | Earl et al. |
| 8,808,387 B2 | 8/2014 | Hawkins et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 8,979,936 B2 | 3/2015 | White et al. |
| 8,998,997 B2 | 4/2015 | Ries et al. |
| 9,011,459 B2 | 4/2015 | Claypool et al. |
| 9,060,866 B2 | 6/2015 | Fankhauser et al. |
| 9,072,607 B2 | 7/2015 | Parisi et al. |
| 9,131,945 B2 | 9/2015 | Aram et al. |
| 9,149,206 B2 | 10/2015 | Claypool et al. |
| 9,173,744 B2 | 11/2015 | Donno et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,095 B2 | 4/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 9,925,052 B2 | 3/2018 | Dai et al. |
| 10,010,330 B2 | 7/2018 | Claypool et al. |
| 10,092,407 B2 | 10/2018 | Faccioli et al. |
| 10,188,530 B2 | 1/2019 | Claypool et al. |
| 10,195,041 B2 | 2/2019 | Wentorf et al. |
| 10,195,056 B2 | 2/2019 | Wogoman et al. |
| 10,265,181 B2 | 4/2019 | Wentorf et al. |
| 10,278,827 B2 | 5/2019 | Drury et al. |
| 10,413,415 B2 | 9/2019 | Parisi et al. |
| 10,470,889 B2 | 11/2019 | Wentorf et al. |
| 10,500,054 B2 | 12/2019 | Croll |
| 10,517,735 B2 | 12/2019 | Lloyd et al. |
| 10,537,445 B2 | 1/2020 | Wogoman et al. |
| 10,543,099 B2 | 1/2020 | Sanford et al. |
| 10,575,956 B2 | 3/2020 | Dai et al. |
| 10,675,153 B2 | 6/2020 | Byrd et al. |
| 10,835,380 B2 | 11/2020 | Drury et al. |
| 10,898,337 B2 | 1/2021 | Parisi et al. |
| 11,051,948 B2 | 7/2021 | Arnold et al. |
| 11,160,659 B2 | 11/2021 | Drury et al. |
| 11,207,198 B2 | 12/2021 | Oh et al. |
| 11,224,519 B2 | 1/2022 | Wentorf et al. |
| 11,324,598 B2 | 5/2022 | Dai et al. |
| 11,324,599 B2 | 5/2022 | Croll |
| 11,426,282 B2 | 8/2022 | Yager |
| 11,471,288 B2 | 10/2022 | Parisi et al. |
| 11,547,571 B2 | 1/2023 | Byrd et al. |
| 11,911,279 B2 | 2/2024 | Drury et al. |
| 12,239,540 B2 | 3/2025 | Wentorf et al. |
| 12,383,407 B2 | 8/2025 | Parisi et al. |
| 12,458,502 B2 | 11/2025 | Byrd et al. |
| 2001/0001478 A1 | 5/2001 | Dams et al. |
| 2001/0047210 A1 | 11/2001 | Wolf |
| 2002/0058997 A1 | 5/2002 | O'connor et al. |
| 2002/0072802 A1 | 6/2002 | O'Neil et al. |
| 2002/0103541 A1 | 8/2002 | Meyers et al. |
| 2002/0120340 A1 | 8/2002 | Metzger et al. |
| 2002/0161448 A1 | 10/2002 | Hayes, Jr. et al. |
| 2003/0055509 A1 | 3/2003 | Mccue et al. |
| 2003/0199985 A1 | 10/2003 | Masini |
| 2004/0019382 A1 | 1/2004 | Amirouche et al. |
| 2004/0019383 A1 | 1/2004 | Beguec |
| 2004/0034432 A1 | 2/2004 | Hughes et al. |
| 2004/0059340 A1 | 3/2004 | Serra et al. |
| 2004/0064191 A1 | 4/2004 | Wasielewski |
| 2004/0122441 A1 | 6/2004 | Muratsu |

(56) References Cited

U.S. PATENT DOCUMENTS

| | | |
|---|---|---|
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |
| 2004/0267371 A1 | 12/2004 | Hayes, Jr. et al. |
| 2005/0055102 A1 | 3/2005 | Tornier et al. |
| 2005/0075736 A1 | 4/2005 | Collazo |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0177170 A1 | 8/2005 | Fisher et al. |
| 2005/0197710 A1 | 9/2005 | Naegerl |
| 2005/0209701 A1 | 9/2005 | Suguro et al. |
| 2005/0209702 A1 | 9/2005 | Todd et al. |
| 2005/0246030 A1 | 11/2005 | Yao |
| 2005/0267485 A1 | 12/2005 | Cordes et al. |
| 2005/0267584 A1 | 12/2005 | Burdulis et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0025866 A1 | 2/2006 | Serafin et al. |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0111726 A1 | 5/2006 | Felt et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor |
| 2006/0195195 A1 | 8/2006 | Burstein et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135924 A1 | 6/2007 | Verhoogen |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0058945 A1 | 3/2008 | Hajaj et al. |
| 2008/0058947 A1 | 3/2008 | Earl et al. |
| 2008/0058948 A1 | 3/2008 | Biegun et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hintermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0140212 A1 | 6/2008 | Metzger et al. |
| 2008/0161918 A1 | 7/2008 | Fankhauser et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0262624 A1 | 10/2008 | White et al. |
| 2008/0281426 A1 | 11/2008 | Fitz et al. |
| 2008/0288080 A1 | 11/2008 | Sancheti |
| 2008/0300689 A1 | 12/2008 | Mc Kinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0043396 A1 | 2/2009 | Komistek |
| 2009/0062806 A1 | 3/2009 | Scott et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-Ganz et al. |
| 2009/0264894 A1 | 10/2009 | Wasielewski |
| 2009/0265011 A1 | 10/2009 | Mandell |
| 2009/0265013 A1 | 10/2009 | Mandell |
| 2009/0287310 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191298 A1 | 7/2010 | Earl et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0292804 A1 | 11/2010 | Samuelson |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0066246 A1 | 3/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0098824 A1 | 4/2011 | Jukes et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0153026 A1 | 6/2011 | Heggendorn et al. |
| 2011/0190898 A1 | 8/2011 | Lenz et al. |
| 2011/0202139 A1 | 8/2011 | Metzger et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0185055 A1 | 7/2012 | Maloney et al. |
| 2012/0232429 A1 | 9/2012 | Fischer et al. |
| 2012/0290088 A1 | 11/2012 | Amirouche et al. |
| 2012/0296437 A1 | 11/2012 | Wyss et al. |

(56) References Cited

U.S. PATENT DOCUMENTS

| | | | |
|---|---|---|---|
| 2012/0310246 A1 | 12/2012 | Belcher et al. |
| 2012/0310361 A1 | 12/2012 | Zubok et al. |
| 2012/0323335 A1 | 12/2012 | Parisi et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2013/0131820 A1 | 5/2013 | Wentorf et al. |
| 2013/0173010 A1 | 7/2013 | Irwin |
| 2013/0226305 A1 | 8/2013 | Donno et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2013/0345820 A1 | 12/2013 | Maloney et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0025644 A1 | 1/2015 | Heggendorn et al. |
| 2015/0066150 A1 | 3/2015 | Dai et al. |
| 2015/0088140 A1 | 3/2015 | Toler et al. |
| 2015/0190243 A1 | 7/2015 | Claypool et al. |
| 2015/0257889 A1 | 9/2015 | Kang |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0030053 A1 | 2/2016 | Yager et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2017/0231773 A1 | 8/2017 | Lu |
| 2017/0266011 A1 | 9/2017 | Wentorf et al. |
| 2017/0281354 A1 | 10/2017 | Soffiatti et al. |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0161166 A1 | 6/2018 | Dai et al. |
| 2018/0256346 A1 | 9/2018 | Byrd et al. |
| 2018/0325684 A1 | 11/2018 | Croll |
| 2019/0142594 A1 | 5/2019 | Yager |
| 2019/0209333 A1 | 7/2019 | Drury et al. |
| 2019/0328535 A1 | 10/2019 | Drury et al. |
| 2019/0350718 A1 | 11/2019 | Parisi et al. |
| 2020/0030106 A1 | 1/2020 | Wentorf et al. |
| 2020/0060833 A1 | 2/2020 | Arnold et al. |
| 2020/0069433 A1 | 3/2020 | Croll |
| 2020/0113702 A1 | 4/2020 | Sanford et al. |
| 2020/0146830 A1 | 5/2020 | Dai et al. |
| 2020/0237518 A1 | 7/2020 | Byrd et al. |
| 2021/0022875 A1 | 1/2021 | Drury et al. |
| 2021/0113340 A1 | 4/2021 | Parisi et al. |
| 2022/0096243 A1 | 3/2022 | Wentorf et al. |
| 2022/0241081 A1 | 8/2022 | Garino |
| 2022/0346962 A1 | 11/2022 | Yager |
| 2023/0113335 A1 | 4/2023 | Byrd et al. |
| 2024/0000575 A1 | 1/2024 | Drury et al. |
| 2025/0169959 A1 | 5/2025 | Wentorf et al. |

FOREIGN PATENT DOCUMENTS

| | | | |
|---|---|---|---|
| CA | 2190029 A1 | 11/1995 |
| CA | 2856070 C | 7/2016 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 4/1998 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101222886 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058446 A | 5/2011 |
| CN | 102058448 A | 5/2011 |
| CN | 102917670 A | 2/2013 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 103732186 A | 4/2014 |
| CN | 104039273 A | 9/2014 |
| CN | 104066402 A | 9/2014 |
| CN | 104093380 A | 10/2014 |
| CN | 104135968 | 11/2014 |
| CN | 104135969 A | 11/2014 |
| CN | 104203160 A | 12/2014 |
| CN | 104321263 A | 1/2015 |
| CN | 104379094 A | 2/2015 |
| CN | 104736105 A | 6/2015 |
| CN | 105055052 A | 11/2015 |
| CN | 105167889 A | 12/2015 |
| CN | 103118634 B | 8/2016 |
| CN | 103118636 B | 8/2016 |
| CN | 104093380 B | 8/2016 |
| CN | 106037997 | 10/2016 |
| CN | 103370025 B | 11/2016 |
| CN | 106073949 A | 11/2016 |
| CN | 106214292 A | 12/2016 |
| CN | 108135701 A | 6/2018 |
| CN | 106073949 B | 12/2018 |
| CN | 109310504 A | 2/2019 |
| CN | 110022798 A | 7/2019 |
| CN | 110402123 A | 11/2019 |
| CN | 110636818 A | 12/2019 |
| CN | 113317912 A | 8/2021 |
| CN | 113317912 | 6/2024 |
| EP | 0021421 A1 | 1/1981 |
| EP | 0303467 A2 | 2/1989 |
| EP | 0327495 A2 | 8/1989 |
| EP | 0340919 A1 | 11/1989 |
| EP | 0372811 A1 | 6/1990 |

(56) References Cited

FOREIGN PATENT DOCUMENTS

| | | | |
|---|---|---|---|
| EP | 0306744 B1 | 4/1992 | |
| EP | 0495340 A1 | 7/1992 | |
| EP | 0636353 A1 | 2/1995 | |
| EP | 0672397 A1 | 9/1995 | |
| EP | 0552950 B1 | 9/1996 | |
| EP | 0536457 B1 | 1/1997 | |
| EP | 0642328 B1 | 12/1998 | |
| EP | 0592750 B1 | 1/1999 | |
| EP | 0903125 A1 | 3/1999 | |
| EP | 0956836 A1 | 11/1999 | |
| EP | 0956836 B1 | 11/1999 | |
| EP | 1025818 A2 | 8/2000 | |
| EP | 1097679 A1 | 5/2001 | |
| EP | 0709074 B1 | 12/2002 | |
| EP | 1327424 A1 | 7/2003 | |
| EP | 1378216 A2 | 1/2004 | |
| EP | 1477143 A1 | 11/2004 | |
| EP | 1568336 A1 | 8/2005 | |
| EP | 1719478 A2 | 11/2006 | |
| EP | 1722721 A1 | 11/2006 | |
| EP | 1354571 B1 | 6/2007 | |
| EP | 1396240 B1 | 4/2008 | |
| EP | 1604623 B1 | 6/2008 | |
| EP | 1996122 A1 | 12/2008 | |
| EP | 0927009 B1 | 1/2009 | |
| EP | 2011455 A1 | 1/2009 | |
| EP | 1696835 B1 | 2/2009 | |
| EP | 1132063 A2 | 9/2009 | |
| EP | 1591082 B1 | 9/2009 | |
| EP | 2140838 A2 | 1/2010 | |
| EP | 2140839 A1 | 1/2010 | |
| EP | 2143403 A1 | 1/2010 | |
| EP | 2237177 A1 | 10/2010 | |
| EP | 1555962 B1 | 2/2011 | |
| EP | 2319460 A1 | 5/2011 | |
| EP | 2324799 A2 | 5/2011 | |
| EP | 2335654 A1 | 6/2011 | |
| EP | 2347733 A1 | 7/2011 | |
| EP | 0689808 B1 | 9/2012 | |
| EP | 2595573 A1 | 5/2013 | |
| EP | 2782525 A1 | 10/2014 | |
| EP | 2830543 A1 | 2/2015 | |
| EP | 2830544 A1 | 2/2015 | |
| EP | 2830544 B1 | 9/2016 | |
| EP | 2918235 B1 | 1/2017 | |
| EP | 3143964 A2 | 3/2017 | |
| EP | 2595574 B1 | 5/2017 | |
| EP | 3111894 B1 | 12/2018 | |
| EP | 3241527 | 10/2024 | |
| EP | 3621558 | 1/2025 | |
| EP | 3848005 | 4/2025 | |
| EP | 4014930 | 4/2025 | |
| EP | 4014929 B1 | 6/2025 | |
| FR | 2728782 A1 | 7/1996 | |
| FR | 2736819 A1 | 1/1997 | |
| FR | 2747914 A1 | 10/1997 | |
| FR | 2773059 A1 * | 7/1999 | ........... A61F 2/3868 |
| FR | 2778332 A1 | 11/1999 | |
| FR | 2788964 A1 | 8/2000 | |
| FR | 2824260 A1 | 11/2002 | |
| FR | 2852819 A1 | 10/2004 | |
| FR | 2926719 A1 | 7/2009 | |
| GB | 225347 A | 12/1924 | |
| GB | 2253147 A | 9/1992 | |
| GB | 2296443 A * | 7/1996 | ........... A61F 2/3886 |
| GB | 2345446 A | 7/2000 | |
| IN | 7145DELNP2014 A | 4/2015 | |
| JP | 61247449 A | 11/1986 | |
| JP | 62270153 A | 11/1987 | |
| JP | 06203576 A | 7/1994 | |
| JP | 09289998 A | 11/1997 | |
| JP | 09511668 A | 11/1997 | |
| JP | 2000000255 A | 1/2000 | |
| JP | 2000245758 A | 9/2000 | |
| JP | 2003516183 A | 5/2003 | |
| JP | 2004166802 A | 6/2004 | |
| JP | 2004254811 A | 9/2004 | |
| JP | 3734270 B2 | 1/2006 | |
| JP | 2007054488 A | 3/2007 | |
| JP | 2007509709 A | 4/2007 | |
| JP | 2007222616 A | 9/2007 | |
| JP | 2009082713 A | 4/2009 | |
| JP | 2009245619 A | 10/2009 | |
| JP | 2010022827 A | 2/2010 | |
| JP | 2010188051 A | 9/2010 | |
| JP | 2010240406 A | 10/2010 | |
| JP | 2010259808 A | 11/2010 | |
| JP | 2011004848 | 1/2011 | |
| JP | 2011092738 A | 5/2011 | |
| JP | 2012500667 A | 1/2012 | |
| JP | 2012531265 A | 12/2012 | |
| JP | 2015512307 A | 4/2013 | |
| JP | 2013535276 A | 9/2013 | |
| JP | 2013536005 A | 9/2013 | |
| JP | 2013536006 A | 9/2013 | |
| JP | 2013536007 A | 9/2013 | |
| JP | 2014505517 A | 3/2014 | |
| JP | 2014508554 A | 4/2014 | |
| JP | 2014522292 A | 9/2014 | |
| JP | 2014239900 A | 12/2014 | |
| JP | 2015502203 A | 1/2015 | |
| JP | 2015504333 A | 2/2015 | |
| JP | 2015504759 A | 2/2015 | |
| JP | 2015513966 A | 5/2015 | |
| JP | 2015231566 A | 12/2015 | |
| JP | 2016028729 A | 3/2016 | |
| JP | 5980341 B2 | 8/2016 | |
| JP | 2016195841 A | 11/2016 | |
| JP | 2017221732 A | 12/2017 | |
| JP | 2021142355 A | 9/2021 | |
| KR | 20150096186 | 8/2015 | |
| WO | WO-9305729 A2 | 4/1993 | |
| WO | WO-9409725 A1 | 5/1994 | |
| WO | WO-9514444 A1 | 6/1995 | |
| WO | WO-9514446 A1 | 6/1995 | |
| WO | WO-9530389 A1 | 11/1995 | |
| WO | WO-9535074 A1 | 12/1995 | |
| WO | WO-9934755 A1 | 7/1999 | |
| WO | WO-0141680 A1 | 6/2001 | |
| WO | WO-200141680 A1 | 6/2001 | |
| WO | WO-03099106 A2 | 12/2003 | |
| WO | WO-2004058108 A1 | 7/2004 | |
| WO | WO-2005037147 A1 | 4/2005 | |
| WO | WO-2005051240 A1 | 6/2005 | |
| WO | WO-2005122967 A1 | 12/2005 | |
| WO | WO-2006058057 A2 | 6/2006 | |
| WO | WO-2006092167 A1 | 9/2006 | |
| WO | WO-2007108804 A1 | 9/2007 | |
| WO | WO-2007109641 A2 | 9/2007 | |
| WO | WO-2007119173 A2 | 10/2007 | |
| WO | WO-2009029631 A1 | 3/2009 | |
| WO | WO-2009088235 A2 | 7/2009 | |
| WO | WO-2009088236 A2 | 7/2009 | |
| WO | WO-2009088238 A2 | 7/2009 | |
| WO | WO-2009105495 A1 | 8/2009 | |
| WO | WO-2010001010 A1 | 1/2010 | |
| WO | WO-2010008803 A2 | 1/2010 | |
| WO | WO-2010011590 A1 | 1/2010 | |
| WO | WO-2010022272 A1 | 2/2010 | |
| WO | WO-2010023062 A2 | 3/2010 | |
| WO | WO-2010045537 A1 | 4/2010 | |
| WO | WO-2010075365 A2 | 7/2010 | |
| WO | WO-2011043955 A1 | 4/2011 | |
| WO | WO-2011063123 A2 | 5/2011 | |
| WO | WO-2011071979 A2 | 6/2011 | |
| WO | WO-2011072235 A2 | 6/2011 | |
| WO | WO-2011110865 A2 | 9/2011 | |
| WO | WO-2012004580 A1 | 1/2012 | |
| WO | WO-2012018563 A1 | 2/2012 | |
| WO | WO-2012018564 A1 | 2/2012 | |
| WO | WO-2012018565 A1 | 2/2012 | |
| WO | WO-2012018566 A1 | 2/2012 | |
| WO | WO-2012018567 A1 | 2/2012 | |
| WO | WO-2012020460 A1 | 2/2012 | |

(56)          References Cited

FOREIGN PATENT DOCUMENTS

| WO | WO-2012082628 A1 | 6/2012 | | |
| WO | WO-2012083280 A1 | 6/2012 | | |
| WO | WO-2012112698 A2 | 8/2012 | | |
| WO | 2012173704 | 12/2012 | | |
| WO | WO-2012173706 A1 | 12/2012 | | |
| WO | WO-2013003433 A1 | 1/2013 | | |
| WO | WO-2013013094 A1 | 1/2013 | | |
| WO | WO-2013041905 A1 * | 3/2013 | .............. | A61F 2/38 |
| WO | WO-2013074142 A1 | 5/2013 | | |
| WO | WO-2013074143 A1 | 5/2013 | | |
| WO | WO-2013074144 A1 | 5/2013 | | |
| WO | WO-2013074145 A1 | 5/2013 | | |
| WO | WO-2013077919 A1 | 5/2013 | | |
| WO | WO-2013115849 A1 | 8/2013 | | |
| WO | WO-2013148954 A1 | 10/2013 | | |
| WO | WO-2013148960 A1 | 10/2013 | | |
| WO | WO-2017053196 A1 | 3/2017 | | |
| WO | WO-2018165442 A1 | 9/2018 | | |
| WO | WO-2018208612 A1 | 11/2018 | | |

OTHER PUBLICATIONS

"U.S. Appl. No. 16/179,201, Notice of Allowance mailed Apr. 21, 22", 9 pgs.
"U.S. Appl. No. 13/087,610, Non Final Office Action mailed Feb. 26, 2013", 7 pgs.
"U.S. Appl. No. 13/087,610, Notice of Allowance mailed Jun. 28, 2013", 6 pgs.
"U.S. Appl. No. 13/087,610, Notice of Allowance mailed Oct. 8, 2013", 7 pgs.
"U.S. Appl. No. 13/087,610, Response filed May 24, 2013 to Non Final Office Action mailed Feb. 26, 2013", 15 pgs.
"U.S. Appl. No. 13/189,324, Examiner Interview Summary mailed Jan. 13, 2014", 4 pgs.
"U.S. Appl. No. 13/189,324, Final Office Action mailed Jul. 16, 2013", 19 pgs.
"U.S. Appl. No. 13/189,324, Non Final Office Action mailed Dec. 11, 2012", 19 pgs.
"U.S. Appl. No. 13/189,324, Notice of Allowance mailed Feb. 20, 2014", 8 pgs.
"U.S. Appl. No. 13/189,324, PTO Response to 312 Amendment mailed May 29, 2014", 2 pgs.
"U.S. Appl. No. 13/189,324, Response filed Jan. 15, 2014 to Final Office Action dated Jul. 16, 2013", 23 pgs.
"U.S. Appl. No. 13/189,324, Response filed Jun. 10, 2013 to Non Final Office Action mailed Dec. 11, 2012", 24 pgs.
"U.S. Appl. No. 13/189,328, Non Final Office Action mailed Mar. 19, 2013", 10 pgs.
"U.S. Appl. No. 13/189,328, Notice of Allowance mailed Oct. 8, 2013", 12 pgs.
"U.S. Appl. No. 13/189,328, PTO Response to 312 Amendment mailed Dec. 13, 2013", 2 pgs.
"U.S. Appl. No. 13/189,328, Response filed Jan. 10, 2013 to Restriction Requirement mailed Dec. 10, 2012", 9 pgs.
"U.S. Appl. No. 13/189,328, Response filed Jul. 18, 2013 to Non Final Office Action mailed Mar. 19, 2013", 16 pgs.
"U.S. Appl. No. 13/189,328, Restriction Requirement mailed Dec. 10, 2012", 6 pgs.
"U.S. Appl. No. 13/189,336, Notice of Allowance mailed Sep. 13, 2013", 30 pgs.
"U.S. Appl. No. 13/189,336, PTO Response to 312 Amendment mailed Nov. 25, 2013", 2 pgs.
"U.S. Appl. No. 13/189,336, Response filed Apr. 15, 2013 to Restriction Requirement mailed Jan. 30, 2013", 21 pgs.
"U.S. Appl. No. 13/189,336, Response filed Jul. 17, 2013 to Restriction Requirement mailed Jun. 17, 2013", 20 pgs.
"U.S. Appl. No. 13/189,336, Restriction Requirement mailed Jan. 30, 2013", 5 pgs.
"U.S. Appl. No. 13/189,336, Restriction Requirement mailed Jun. 17, 2013", 6 pgs.

"U.S. Appl. No. 13/189,338, Notice of Allowance mailed Sep. 23, 2013", 23 pgs.
"U.S. Appl. No. 13/189,338, Response filed Apr. 15, 2013 to Restriction Requirement mailed Feb. 14, 2013", 18 pgs.
"U.S. Appl. No. 13/189,338, Response filed Jul. 17, 2013 to Restriction Requirement mailed Jun. 17, 2013", 16 pgs.
"U.S. Appl. No. 13/189,338, Restriction Requirement mailed Feb. 14, 2013", 5 pgs.
"U.S. Appl. No. 13/189,338, Restriction Requirement mailed Jun. 17, 2013", 6 pgs.
"U.S. Appl. No. 13/189,339, Notice of Allowance mailed Sep. 20, 2013", 16 pgs.
"U.S. Appl. No. 13/189,339, Response filed Apr. 15, 2013 to Restriction Requirement mailed Mar. 6, 2013", 11 pgs.
"U.S. Appl. No. 13/189,339, Response filed Jul. 17, 2013 to Restriction Requirement mailed Jun. 17, 2013", 10 pgs.
"U.S. Appl. No. 13/189,339, Restriction Requirement mailed Mar. 6, 2013", 6 pgs.
"U.S. Appl. No. 13/189,339, Restriction Requirement mailed Jun. 17, 2013", 7 pgs.
"U.S. Appl. No. 13/229,103, Applicant Interview Summary mailed Sep. 23, 2013", 2 pgs.
"U.S. Appl. No. 13/229,103, Examiner Interview Summary mailed Sep. 13, 2013", 3 pgs.
"U.S. Appl. No. 13/229,103, Non Final Office Action mailed Apr. 1, 2013", 18 pgs.
"U.S. Appl. No. 13/229,103, Notice of Allowance mailed Sep. 18, 2013", 9 pgs.
"U.S. Appl. No. 13/229,103, Response filed Jul. 1, 2013 to Non Final Office Action mailed Apr. 1, 2013", 19 pgs.
"U.S. Appl. No. 13/229,103, Supplemental Notice of Allowability mailed Oct. 18, 2013", 2 pgs.
"U.S. Appl. No. 13/459,037, Final Office Action mailed Sep. 23, 2013", 9 pgs.
"U.S. Appl. No. 13/459,037, Non Final Office Action mailed Apr. 23, 2013", 10 pgs.
"U.S. Appl. No. 13/459,037, Notice of Allowance mailed Jun. 13, 2014", 9 pgs.
"U.S. Appl. No. 13/459,037, Preliminary Amendment filed Apr. 27, 2012", 3 pgs.
"U.S. Appl. No. 13/459,037, Response filed Mar. 21, 2014 to Final Office Action mailed Sep. 23, 2013", 15 pgs.
"U.S. Appl. No. 13/459,037, Response filed Mar. 28, 2013 to Restriction Requirement mailed Feb. 26, 2013", 9 pgs.
"U.S. Appl. No. 13/459,037, Response filed Jul. 23, 2013 to Non Final Office Action mailed Apr. 23, 2013", 19 pgs.
"U.S. Appl. No. 13/459,037, Restriction Requirement mailed Feb. 26, 2013", 6 pgs.
"U.S. Appl. No. 13/459,041, Non Final Office Action mailed Jan. 15, 2014", 16 pgs.
"U.S. Appl. No. 13/459,041, Non Final Office Action mailed Sep. 9, 2014", 14 pgs.
"U.S. Appl. No. 13/459,041, Notice of Allowance mailed Apr. 2, 2015", 10 pgs.
"U.S. Appl. No. 13/459,041, Preliminary Amendment mailed Apr. 27, 2012", 7 pgs.
"U.S. Appl. No. 13/459,041, PTO Response to Rule 312 Communication mailed Jun. 9, 2015", 2 pgs.
"U.S. Appl. No. 13/459,041, Response filed May 15, 2014 to Non-Final Office Action dated Jan. 15, 2014", 24 pgs.
"U.S. Appl. No. 13/459,041, Response filed Sep. 23, 2013 to Restriction Requirement mailed Jul. 25, 2013", 18 pgs.
"U.S. Appl. No. 13/459,041, Response filed Dec. 9, 2014 to Non-Final Office Action mailed Sep. 9, 2014", 23 pgs.
"U.S. Appl. No. 13/459,041, Restriction Requirement mailed Jul. 25, 2013", 9 pgs.
"U.S. Appl. No. 13/459,048, Non Final Office Action mailed Jul. 11, 2013", 6 pgs.
"U.S. Appl. No. 13/459,048, Notice of Allowance mailed Nov. 26, 2013", 10 pgs.
"U.S. Appl. No. 13/459,048, Preliminary Amendment filed Apr. 27, 2012", 7 pgs.

(56)  References Cited

OTHER PUBLICATIONS

"U.S. Appl. No. 13/459,048, Response filed Nov. 11, 2013 to Non-Final Office Action mailed Jul. 11, 2013", 16 pgs.
"U.S. Appl. No. 13/459,056, Examiner Interview Summary mailed Dec. 26, 2013", 3 pgs.
"U.S. Appl. No. 13/459,056, Non Final Office Action mailed Jul. 25, 2013", 11 pgs.
"U.S. Appl. No. 13/459,056, Notice of Allowance mailed Feb. 20, 2014", 5 pgs.
"U.S. Appl. No. 13/459,056, Preliminary Amendment filed Apr. 27, 2012", 7 pgs.
"U.S. Appl. No. 13/459,056, PTO Response to Rule 312 Communication mailed May 22, 2014", 2 pgs.
"U.S. Appl. No. 13/459,056, Response filed Jan. 24, 2014 to Non-Final office Action mailed Jul. 25, 2013", 27 pgs.
"U.S. Appl. No. 13/459,056, Response filed Apr. 8, 2013 to Restriction Requirement mailed Mar. 6, 2013", 15 pgs.
"U.S. Appl. No. 13/459,056, Restriction Requirement mailed Mar. 6, 2013", 6 pgs.
"U.S. Appl. No. 13/593,339, Non Final Office Action mailed Oct. 4, 2013", 7 pgs.
"U.S. Appl. No. 13/593,339, Notice of Allowance mailed Feb. 14, 2014", 9 pgs.
"U.S. Appl. No. 13/593,339, Preliminary Amendment filed Aug. 23, 2012", 6 pgs.
"U.S. Appl. No. 13/593,339, Response filed Jan. 31, 2014 to Non-Final Office Action dated Oct. 4, 2013", 19 pgs.
"U.S. Appl. No. 13/593,339, Response filed Aug. 30, 2013 to Restriction Requirement mailed Aug. 1, 2013", 14 pgs.
"U.S. Appl. No. 13/593,339, Restriction Requirement mailed Aug. 1, 2013", 5 pgs.
"U.S. Appl. No. 13/593,339, Supplemental Notice of Allowability mailed Mar. 31, 2014", 2 pgs.
"U.S. Appl. No. 13/594,543, Corrected Notice of Allowance mailed Mar. 16, 2016", 2 pgs.
"U.S. Appl. No. 13/594,543, Examiner Interview Summary mailed Jan. 22, 2016", 3 pgs.
"U.S. Appl. No. 13/594,543, Final Office Action mailed Jul. 17, 2014", 12 pgs.
"U.S. Appl. No. 13/594,543, Final Office Action mailed Nov. 20, 2015", 28 pgs.
"U.S. Appl. No. 13/594,543, Non Final Office Action mailed Jun. 19, 2015", 30 pgs.
"U.S. Appl. No. 13/594,543, Non Final Office Action mailed Dec. 26, 2013", 15 pgs.
"U.S. Appl. No. 13/594,543, Non-Final Office Action mailed Jan. 9, 2015", 23 pgs.
"U.S. Appl. No. 13/594,543, Notice of Allowance mailed Mar. 1, 2016", 9 pgs.
"U.S. Appl. No. 13/594,543, Preliminary Amendment filed Aug. 24, 2012", 4 pgs.
"U.S. Appl. No. 13/594,543, Response filed Feb. 8, 2016 to Final Office Action mailed Nov. 20, 2015", 17 pgs.
"U.S. Appl. No. 13/594,543, Response filed Apr. 7, 2015 to Non-Final Office Action mailed Jan. 9, 2015", 27 pgs.
"U.S. Appl. No. 13/594,543, Response filed May 7, 2014 to Non-Final office Action mailed Dec. 26, 2013", 17 pgs.
"U.S. Appl. No. 13/594,543, Response filed Sep. 21, 2015 to Non-Final Office Action mailed Jun. 19, 2015", 25 pgs.
"U.S. Appl. No. 13/594,543, Response filed Oct. 11, 2013 to Restriction Requirement mailed Sep. 12, 2013", 8 pgs.
"U.S. Appl. No. 13/594,543, Response filed Dec. 17, 2014 to Final Office Action mailed Jul. 17, 2014", 15 pgs.
"U.S. Appl. No. 13/594,543, Restriction Requirement mailed Sep. 12, 2013", 5 pgs.
"U.S. Appl. No. 13/819,116, Advisory Action mailed Jan. 5, 2016", 3 pgs.
"U.S. Appl. No. 13/819,116, Corrected Notice of Allowance mailed Oct. 21, 2016", 2 pgs.

"U.S. Appl. No. 13/819,116, Examiner Interview Summary mailed Apr. 18, 2016", 11 pgs.
"U.S. Appl. No. 13/819,116, Final Office Action mailed Jul. 26, 2016", 6 pgs.
"U.S. Appl. No. 13/819,116, Final Office Action mailed Oct. 21, 2015", 15 pgs.
"U.S. Appl. No. 13/819,116, Non Final Office Action mailed Feb. 17, 2016", 15 pgs.
"U.S. Appl. No. 13/819,116, Non Final Office Action mailed Jun. 2, 2015", 14 pgs.
"U.S. Appl. No. 13/819,116, Notice of Allowance mailed Sep. 29, 2016", 5 pgs.
"U.S. Appl. No. 13/819,116, Preliminary Amendment filed Feb. 26, 2013", 8 pgs.
"U.S. Appl. No. 13/819,116, Response filed Mar. 27, 2015 to Restriction Requirement mailed Feb. 12, 2015", 11 pgs.
"U.S. Appl. No. 13/819,116, Response filed Apr. 29, 2016 to Non Final Office Action mailed Feb. 17, 2016", 17 pgs.
"U.S. Appl. No. 13/819,116, Response filed Jul. 16, 2015 to Non Final Office Action mailed Jun. 2, 2015", 22 pgs.
"U.S. Appl. No. 13/819,116, Response filed Sep. 14, 2016 Final Office Action mailed Jul. 26, 2016", 10 pgs.
"U.S. Appl. No. 13/819,116, Response filed Dec. 15, 2015 to Final Office Action mailed Oct. 21, 2015", 16 pgs.
"U.S. Appl. No. 13/819,116, Restriction Requirement mailed Feb. 12, 2015", 7 pgs.
"U.S. Appl. No. 13/836,586, Express Abandonment filed May 30, 2014", 1 pg.
"U.S. Appl. No. 13/836,665, Examiner Interview Summary mailed Jul. 17, 2014", 4 pgs.
"U.S. Appl. No. 13/836,665, Final Office Action mailed Jul. 25, 2014", 25 pgs.
"U.S. Appl. No. 13/836,665, Non Final Office Action mailed Jan. 30, 2014", 21 pgs.
"U.S. Appl. No. 13/836,665, Notice of Allowance mailed Jun. 9, 2015", 10 pgs.
"U.S. Appl. No. 13/836,665, Response filed Jan. 23, 2015 to Final Office Action mailed Jul. 25, 2014", 25 pgs.
"U.S. Appl. No. 13/836,665, Response filed May 30, 2014 to Non-Final Office Action mailed Jan. 30, 2014", 21 pgs.
"U.S. Appl. No. 13/837,294, Final Office Action mailed Apr. 25, 2016", 7 pgs.
"U.S. Appl. No. 13/837,294, Final Office Action mailed Jun. 2, 2016", 7 pgs.
"U.S. Appl. No. 13/837,294, Non Final Office Action mailed Dec. 10, 2015", 8 pgs.
"U.S. Appl. No. 13/837,294, Notice of Allowance mailed Aug. 25, 2016", 5 pgs.
"U.S. Appl. No. 13/837,294, Response filed Mar. 4, 2016 to Non Final Office Action mailed Dec. 10, 2015", 16 pgs.
"U.S. Appl. No. 13/837,294, Response filed Aug. 3, 2016 to Final Office Action mailed Jun. 2, 2016", 7 pgs.
"U.S. Appl. No. 13/837,294, Response filed Oct. 12, 2015 to Restriction Requirement mailed Aug. 24, 2015", 9 pgs.
"U.S. Appl. No. 13/837,294, Restriction Requirement mailed Aug. 24, 2015", 6 pgs.
"U.S. Appl. No. 13/837,774, Examiner Interview Summary mailed Jul. 22, 2014", 4 pgs.
"U.S. Appl. No. 13/837,774, Final Office Action mailed Mar. 17, 2016", 14 pgs.
"U.S. Appl. No. 13/837,774, Final Office Action mailed Jul. 28, 2014", 17 pgs.
"U.S. Appl. No. 13/837,774, Non Final Office Action mailed Feb. 10, 2014", 33 pgs.
"U.S. Appl. No. 13/837,774, Non Final Office Action mailed Sep. 18, 2015", 16 pgs.
"U.S. Appl. No. 13/837,774, Response filed Jan. 28, 2015 to Final Office Action mailed Jul. 28, 2014", 16 pgs.
"U.S. Appl. No. 13/837,774, Response filed Jun. 10, 2014 to Non-Final Office Action mailed Feb. 20, 2014", 29 pgs.
"U.S. Appl. No. 13/837,774, Response filed Jul. 7, 2015 to Restriction Requirement mailed May 20, 2015", 10 pgs.

(56) References Cited

OTHER PUBLICATIONS

"U.S. Appl. No. 13/837,774, Response filed Dec. 16, 2015 to Non Final Office Action mailed Sep. 18, 2015", 17 pgs.

"U.S. Appl. No. 13/837,774, Restriction Requirement mailed May 20, 2015", 6 pgs.

"U.S. Appl. No. 14/034,076, Appeal Brief Filed Apr. 18, 2016", 21 pgs.

"U.S. Appl. No. 14/034,076, Final Office Action mailed Dec. 21, 2015", 11 pgs.

"U.S. Appl. No. 14/034,076, Non Final Office Action mailed Jun. 24, 2015", 11 pgs.

"U.S. Appl. No. 14/034,076, Notice of Allowance mailed Oct. 28, 2016", 7 pgs.

"U.S. Appl. No. 14/034,076, Response filed Nov. 16, 2015 to Non Final Office Action mailed Jun. 24, 2015", 13 pgs.

"U.S. Appl. No. 14/034,937, Appeal Brief Filed Sep. 9, 2015", 41 pgs.

"U.S. Appl. No. 14/034,937, Appeal Decision mailed May 30, 2017", 34 pgs.

"U.S. Appl. No. 14/034,937, Final Office Action mailed Jun. 5, 2015", 22 pgs.

"U.S. Appl. No. 14/034,937, Non Final Office Action mailed Jan. 2, 2015", 21 pgs.

"U.S. Appl. No. 14/034,937, Notice of Allowance mailed Aug. 30, 2017", 14 pgs.

"U.S. Appl. No. 14/034,937, Preliminary Amendment filed Sep. 24, 2013", 3 pgs.

"U.S. Appl. No. 14/034,937, PTO Response to Rule 312 Communication mailed Oct. 10, 2017", 2 pgs.

"U.S. Appl. No. 14/034,937, Response filed Mar. 30, 2015 to Non-Final Office Action", 24 pgs.

"U.S. Appl. No. 14/034,937, Response filed Oct. 27, 2014 to Restriction Requirement mailed Sep. 11, 2014", 12 pgs.

"U.S. Appl. No. 14/034,937, Restriction Requirement mailed Sep. 11, 2014", 6 pgs.

"U.S. Appl. No. 14/034,937, Supplemental Preliminary Amendment filed Oct. 24, 2013", 11 pgs.

"U.S. Appl. No. 14/034,944, Non Final Office Action mailed Mar. 3, 2015", 16 pgs.

"U.S. Appl. No. 14/034,944, Notice of Allowance mailed Aug. 28, 2015", 7 pgs.

"U.S. Appl. No. 14/034,944, Preliminary Amendment filed Sep. 24, 2013", 3 pgs.

"U.S. Appl. No. 14/034,944, Response filed Jun. 23, 2015 to Non Final Office Action mailed Mar. 3, 2015", 15 pgs.

"U.S. Appl. No. 14/034,944, Response filed Dec. 15, 2014 to Restriction Requirement mailed Oct. 14, 2014", 12 pgs.

"U.S. Appl. No. 14/034,944, Restriction Requirement mailed Oct. 14, 2014", 6 pgs.

"U.S. Appl. No. 14/034,944, Supplemental Preliminary Amendment filed Oct. 24, 2013", 11 pgs.

"U.S. Appl. No. 14/034,954, Advisory Action mailed Aug. 25, 2015", 3 pgs.

"U.S. Appl. No. 14/034,954, Final Office Action mailed Jun. 1, 2015", 26 pgs.

"U.S. Appl. No. 14/034,954, Non Final Office Action mailed Dec. 19, 2014", 25 pgs.

"U.S. Appl. No. 14/034,954, Notice of Allowance mailed Nov. 20, 2015", 11 pgs.

"U.S. Appl. No. 14/034,954, Preliminary Amendment filed Sep. 24, 2013", 3 pgs.

"U.S. Appl. No. 14/034,954, Response filed Mar. 17, 2015 to Non Final Office Action mailed Dec. 19, 2014", 21 pgs.

"U.S. Appl. No. 14/034,954, Response filed Aug. 3, 2015 to Final Office Action mailed Jun. 1, 2015", 19 pgs.

"U.S. Appl. No. 14/034,954, Response filed Aug. 31, 2015 to Advisory Action mailed Aug. 25, 2015", 21 pgs.

"U.S. Appl. No. 14/034,954, Response filed Oct. 27, 2014 to Restriction Requirement mailed Aug. 25, 2014", 11 pgs.

"U.S. Appl. No. 14/034,954, Restriction Requirement mailed Aug. 25, 2014", 7 pgs.

"U.S. Appl. No. 14/034,954, Supplemental Preliminary Amendment filed Oct. 25, 2013", 8 pgs.

"U.S. Appl. No. 14/034,963, Final Office Action mailed Apr. 13, 2015", 22 pgs.

"U.S. Appl. No. 14/034,963, Final Office Action mailed Oct. 13, 2015", 11 pgs.

"U.S. Appl. No. 14/034,963, Non Final Office Action mailed Jul. 1, 2015", 15 pgs.

"U.S. Appl. No. 14/034,963, Non Final Office Action mailed Nov. 21, 2014", 19 pgs.

"U.S. Appl. No. 14/034,963, Notice of Allowance mailed Dec. 18, 2015", 5 pgs.

"U.S. Appl. No. 14/034,963, Preliminary Amendment filed Sep. 24, 2013", 3 pgs.

"U.S. Appl. No. 14/034,963, Response filed Mar. 20, 2015 to Non-Final Office Action mailed Nov. 21, 2014", 20 pgs.

"U.S. Appl. No. 14/034,963, Response filed Jun. 19, 2015 to Final Office Action mailed Apr. 13, 2015", 17 pgs.

"U.S. Appl. No. 14/034,963, Response filed Sep. 30, 2015 to Non Final Office Action mailed Jul. 1, 2015", 14 pgs.

"U.S. Appl. No. 14/034,963, Response filed Nov. 20, 2015 to Final Office Action mailed Oct. 13, 2015", 12 pgs.

"U.S. Appl. No. 14/063,032, Non Final Office Action mailed Jun. 20, 2014", 6 pgs.

"U.S. Appl. No. 14/063,032, Notice of Allowance mailed Dec. 19, 2014", 6 pgs.

"U.S. Appl. No. 14/063,032, Preliminary Amendment filed Oct. 25, 2013", 3 pgs.

"U.S. Appl. No. 14/063,032, Response filed Oct. 20, 2014 to Non-Final Office Action mailed Jun. 20, 2014", 9 pgs.

"U.S. Appl. No. 14/063,593, Advisory Action mailed Aug. 19, 2016", 3 pgs.

"U.S. Appl. No. 14/063,593, Final Office Action mailed Jun. 9, 2016", 10 pgs.

"U.S. Appl. No. 14/063,593, Non Final Office Action mailed Jan. 25, 2016", 9 pgs.

"U.S. Appl. No. 14/063,593, Non Final Office Action mailed Nov. 30, 2016", 12 pgs.

"U.S. Appl. No. 14/063,593, Notice of Allowance mailed May 2, 2017", 5 pgs.

"U.S. Appl. No. 14/063,593, Notice of Allowance mailed May 25, 2017", 5 pgs.

"U.S. Appl. No. 14/063,593, Preliminary Amendment filed Oct. 25, 2013", 3 pgs.

"U.S. Appl. No. 14/063,593, Response filed Jan. 4, 2016 to Restriction Requirement mailed Nov. 6, 2015", 6 pgs.

"U.S. Appl. No. 14/063,593, Response filed Feb. 24, 2017 to Non Final Office Action mailed Nov. 30, 2016", 17 pgs.

"U.S. Appl. No. 14/063,593, Response filed Apr. 20, 2016 to Non Final Office Action mailed Jan. 25, 2016", 17 pgs.

"U.S. Appl. No. 14/063,593, Response filed Aug. 11, 2016 to Final Office Action mailed Jun. 9, 2016", 10 pgs.

"U.S. Appl. No. 14/063,593, Restriction Requirement mailed Nov. 6, 2015", 6 pgs.

"U.S. Appl. No. 14/181,033, Non Final Office Action mailed May 1, 2015", 5 pgs.

"U.S. Appl. No. 14/181,033, Notice of Allowance mailed Jul. 17, 2015", 10 pgs.

"U.S. Appl. No. 14/181,033, Response filed Jun. 22, 2015 to Non-Final Office Action mailed May 1, 2015", 11 pgs.

"U.S. Appl. No. 14/278,805, Notice of Allowance mailed Dec. 1, 2015", 8 pgs.

"U.S. Appl. No. 14/278,805, Supplemental Notice of Allowability mailed Jan. 21, 2016", 2 pgs.

"U.S. Appl. No. 14/284,028, Non Final Office Action mailed Jul. 7, 2015", 17 pgs.

"U.S. Appl. No. 14/284,028, Notice of Allowance mailed Nov. 6, 2015", 5 pgs.

"U.S. Appl. No. 14/284,028, Response filed Oct. 6, 2015 to Non Final Office Action mailed Jul. 7, 2015", 15 pgs.

(56) References Cited

OTHER PUBLICATIONS

"U.S. Appl. No. 14/284,028, Supplemental Notice of Allowability mailed Feb. 26, 2016", 5 pgs.

"U.S. Appl. No. 14/284,028, Supplemental Preliminary Amendment filed Jul. 8, 2014", 13 pgs.

"U.S. Appl. No. 14/284,144, Final Office Action mailed Aug. 7, 2015", 13 pgs.

"U.S. Appl. No. 14/284,144, Non Final Office Action mailed Mar. 25, 2015", 26 pgs.

"U.S. Appl. No. 14/284,144, Notice of Allowance mailed Oct. 29, 2015", 8 pgs.

"U.S. Appl. No. 14/284,144, Preliminary Amendment filed May 21, 2014", 3 pgs.

"U.S. Appl. No. 14/284,144, Response filed Oct. 9, 2015 to Final Office Action mailed Aug. 7, 2015", 13 pgs.

"U.S. Appl. No. 14/284,144, Response filed Jun. 23, 2015 to Non Final Office Action mailed Mar. 25, 2015", 22 pgs.

"U.S. Appl. No. 14/284,144, Supplemental Preliminary Amendment filed Jul. 3, 2014", 10 pgs.

"U.S. Appl. No. 14/304,009, Notice of Allowance mailed Nov. 16, 2016", 7 pgs.

"U.S. Appl. No. 14/304,009, Preliminary Amendment Filed Jul. 31, 2014", 7 pgs.

"U.S. Appl. No. 14/471,440, Notice of Allowance mailed Nov. 13, 2017", 9 pgs.

"U.S. Appl. No. 14/471,440, Response filed Aug. 16, 2017 to Restriction Requirement mailed Jun. 30, 2017", 8 pgs.

"U.S. Appl. No. 14/471,440, Restriction Requirement mailed Jun. 30, 2017", 6 pgs.

"U.S. Appl. No. 14/490,153, Final Office Action mailed Apr. 15, 2015", 18 pgs.

"U.S. Appl. No. 14/490,153, Non Final Office Action mailed Nov. 12, 2014", 9 pgs.

"U.S. Appl. No. 14/490,153, Notice of Allowance mailed Aug. 14, 2015", 10 pgs.

"U.S. Appl. No. 14/490,153, Preliminary Amendment filed Sep. 18, 2014", 3 pgs.

"U.S. Appl. No. 14/490,153, Response filed Feb. 18, 2015 to Non-Final Office Action mailed Nov. 12, 2014", 14 pgs.

"U.S. Appl. No. 14/490,153, Response filed Jul. 7, 2015 to Final Office Action mailed Apr. 15, 2015", 14 pgs.

"U.S. Appl. No. 14/660,217, Corrected Notice of Allowance mailed May 26, 2016", 3 pgs.

"U.S. Appl. No. 14/660,217, Non Final Office Action mailed Dec. 17, 2015", 8 pgs.

"U.S. Appl. No. 14/660,217, Notice of Allowance mailed Apr. 26, 2016", 5 pgs.

"U.S. Appl. No. 14/660,217, Preliminary Amendment filed Mar. 18, 2015", 9 pgs.

"U.S. Appl. No. 14/660,217, Response filed Mar. 23, 2016 to Non Final Office Action mailed Dec. 17, 2015", 14 pgs.

"U.S. Appl. No. 14/740,690, Non Final Office Action mailed Dec. 7, 2016", 19 pgs.

"U.S. Appl. No. 14/740,690, Notice of Allowability mailed Aug. 29, 2017", 2 pgs.

"U.S. Appl. No. 14/740,690, Notice of Allowance mailed Jun. 13, 2017", 9 pgs.

"U.S. Appl. No. 14/740,690, Response filed Mar. 3, 2017 to Non Final Office Action mailed Dec. 7, 2016", 14 pgs.

"U.S. Appl. No. 14/791,952, Corrected Notice of Allowance mailed Jul. 21, 2017", 2 pgs.

"U.S. Appl. No. 14/791,952, Final Office Action mailed Mar. 31, 2017", 8 pgs.

"U.S. Appl. No. 14/791,952, Final Office Action mailed Sep. 1, 2016", 17 pgs.

"U.S. Appl. No. 14/791,952, Non Final Office Action mailed Apr. 21, 2016", 12 pgs.

"U.S. Appl. No. 14/791,952, Non Final Office Action mailed Dec. 29, 2016", 12 pgs.

"U.S. Appl. No. 14/791,952, Notice of Allowance mailed May 30, 2017", 7 pgs.

"U.S. Appl. No. 14/791,952, Preliminary Amendment filed Jul. 7, 2015", 7 pgs.

"U.S. Appl. No. 14/791,952, Response filed Mar. 20, 2017 to Non Final Office Action mailed Dec. 29, 2016", 12 pgs.

"U.S. Appl. No. 14/791,952, Response filed May 17, 2017—to Final Office Action mailed Mar. 31, 2017", 10 pgs.

"U.S. Appl. No. 14/791,952, Response filed Jul. 15, 2016 to Non Final Office Action mailed Apr. 21, 2016", 18 pgs.

"U.S. Appl. No. 14/791,952, Response filed Nov. 21, 2016 to Final Office Action mailed Sep. 1, 2016", 15 pgs.

"U.S. Appl. No. 14/833,385, Examiner Interview Summary mailed Dec. 27, 2017", 3 pgs.

"U.S. Appl. No. 14/833,385, Final Office Action mailed Nov. 13, 2017", 9 pgs.

"U.S. Appl. No. 14/833,385, Non Final Office Action mailed Jun. 19, 2017", 10 pgs.

"U.S. Appl. No. 14/833,385, Preliminary Amendment filed Aug. 25, 2015", 6 pgs.

"U.S. Appl. No. 14/833,385, Response filed May 12, 2017 to Restriction Requirement mailed Mar. 17, 2017", 8 pgs.

"U.S. Appl. No. 14/833,385, Response filed Sep. 18, 2017 to Non Final Office Action mailed Jun. 19, 2017", 14 pgs.

"U.S. Appl. No. 14/833,385, Restriction Requirement mailed Mar. 17, 2017", 6 pgs.

"U.S. Appl. No. 14/918,721, Final Office Action mailed Oct. 20, 2016", 5 pgs.

"U.S. Appl. No. 14/918,721, Non Final Office Action mailed Jun. 16, 2016", 6 pgs.

"U.S. Appl. No. 14/918,721, Notice of Allowance mailed Feb. 1, 2017", 9 pgs.

"U.S. Appl. No. 14/918,721, Preliminary Amendment filed Oct. 23, 2015", 8 pgs.

"U.S. Appl. No. 14/918,721, PTO Response to Rule 312 Communication mailed Mar. 17, 2017", 2 pgs.

"U.S. Appl. No. 14/918,721, Response filed Sep. 12, 2016 to Non Final Office Action mailed Jun. 16, 2016", 12 pgs.

"U.S. Appl. No. 14/918,721, Response filed Dec. 13, 2016 to Final Office Action mailed Oct. 20, 2016", 9 pgs.

"U.S. Appl. No. 14/926,281, Non Final Office Action mailed Jun. 21, 2017", 17 pgs.

"U.S. Appl. No. 14/926,281, Notice of Allowance mailed Nov. 16, 2017", 9 pgs.

"U.S. Appl. No. 14/926,281, Preliminary Amendment filed Oct. 30, 2015", 8 pgs.

"U.S. Appl. No. 14/926,281, Response filed Sep. 18, 2017 to Non Final Office Action mailed Jun. 21, 2017", 11 pgs.

"U.S. Appl. No. 15/003,091, Preliminary Amendment filed Jan. 22, 2016", 12 pgs.

"U.S. Appl. No. 15/003,091, Non Final Office Action mailed Jun. 20, 2017", 14 pgs.

"U.S. Appl. No. 15/003,091, Notice of Allowance mailed Nov. 6, 2017", 8 pgs.

"U.S. Appl. No. 15/003,091, PTO Response to Rule 312 Communication mailed Jan. 23, 2018", 2 pgs.

"U.S. Appl. No. 15/003,091, Response filed Sep. 20, 2017 to Non Final Office Action mailed Jun. 20, 2017", 17 pgs.

"U.S. Appl. No. 15/045,799, Non Final Office Action mailed Nov. 1, 2016", 8 pgs.

"U.S. Appl. No. 15/045,799, Notice of Allowance mailed Mar. 10, 2017", 10 pgs.

"U.S. Appl. No. 15/045,799, Preliminary Amendment filed Feb. 18, 2016", 9 pgs.

"U.S. Appl. No. 15/045,799, PTO Response to Rule 312 Communication mailed Apr. 18, 2017", 2 pgs.

"U.S. Appl. No. 15/045,799, Response filed Feb. 1, 2017 to Non Final Office Action mailed Nov. 1, 2016", 15 pgs.

"U.S. Appl. No. 15/062,252, Preliminary Amendment filed Mar. 9, 2016", 8 pgs.

"U.S. Appl. No. 15/062,262, Non Final Office Action mailed Jul. 22, 2016", 12 pgs.

(56)          References Cited

OTHER PUBLICATIONS

"U.S. Appl. No. 15/062,262, Notice of Allowance mailed Jan. 31, 2017", 5 pgs.

"U.S. Appl. No. 15/062,262, PTO Response to Rule 312 Communication mailed Mar. 7, 2017", 2 pgs.

"U.S. Appl. No. 15/062,262, Response filed Oct. 24, 2016 to Non Final Office Action mailed Jul. 22, 2016", 13 pgs.

"U.S. Appl. No. 15/177,734, Non Final Office Action mailed Feb. 10, 2017", 21 pgs.

"U.S. Appl. No. 15/177,734, Notice of Allowance mailed May 17, 2017", 7 pgs.

"U.S. Appl. No. 15/177,734, Preliminary Amendment filed Jun. 22, 2016", 8 pgs.

"U.S. Appl. No. 15/177,734, Response filed Apr. 19, 2017 to Non Final Office Action mailed Feb. 10, 2017", 22 pgs.

"U.S. Appl. No. 15/211,812, Non Final Office Action mailed Jan. 27, 2017", 5 pgs.

"U.S. Appl. No. 15/211,812, Notice of Allowance mailed May 31, 2017", 5 pgs.

"U.S. Appl. No. 15/211,812, Preliminary Amendment filed Sep. 8, 2016", 8 pgs.

"U.S. Appl. No. 15/211,812, Response filed Apr. 19, 2017 to Non Final Office Action mailed Jan. 27, 2017", 9 pgs.

"U.S. Appl. No. 15/267,793, Non Final Office Action mailed Jun. 14, 2018", 12 pgs.

"U.S. Appl. No. 15/267,793, Notice of Allowability mailed Jan. 17, 2019", 2 pgs.

"U.S. Appl. No. 15/267,793, Notice of Allowance mailed Dec. 21, 2018", 5 pgs.

"U.S. Appl. No. 15/267,793, Response Filed Apr. 11, 2018 to Restriction Requirement Mailed Feb. 16, 2018", 8 pgs.

"U.S. Appl. No. 15/267,793, Response filed Aug. 22, 2018 Non Final Office Action mailed Jun. 14, 2018", 16 pgs.

"U.S. Appl. No. 15/267,793, Restriction Requirement mailed Feb. 16, 2018", 7 pgs.

"U.S. Appl. No. 15/424,328, Non Final Office Action mailed Jun. 23, 2017", 5 pgs.

"U.S. Appl. No. 15/424,328, Notice of Allowance mailed Oct. 16, 2017", 6 pgs.

"U.S. Appl. No. 15/424,328, Preliminary Amendment filed Feb. 28, 2017", 10 pgs.

"U.S. Appl. No. 15/424,328, Response filed Sep. 20, 2017 to Non Final Office Action mailed Jun. 23, 2017", 9 pgs.

"U.S. Appl. No. 15/435,620, Final Office Action mailed Dec. 15, 2017", 9 pgs.

"U.S. Appl. No. 15/435,620, Non Final Office Action mailed Jul. 26, 2017", 10 pgs.

"U.S. Appl. No. 15/435,620, Notice of Allowance mailed Mar. 13, 2018", 5 pgs.

"U.S. Appl. No. 15/435,620, Preliminary Amendment filed Mar. 20, 2017", 7 pgs.

"U.S. Appl. No. 15/435,620, Response filed Feb. 12, 2018 to Final Office Action mailed Dec. 15, 2017", 9 pgs.

"U.S. Appl. No. 15/435,620, Response filed Oct. 25, 2017 to Non Final Office Action mailed Jul. 26, 2017", 13 pgs.

"U.S. Appl. No. 15/616,561, Non Final Office Action mailed Aug. 9, 2018", 8 pgs.

"U.S. Appl. No. 15/616,561, Notice of Allowability mailed Feb. 12, 2019", 2 pgs.

"U.S. Appl. No. 15/616,561, Notice of Allowance mailed Dec. 10, 2018", 7 pgs.

"U.S. Appl. No. 15/616,561, Preliminary Amendment filed Jun. 8, 2017", 7 pgs.

"U.S. Appl. No. 15/616,561, Response filed Nov. 8, 2018 to Non Final Office Action mailed Aug. 9, 2018", 11 pgs.

"U.S. Appl. No. 15/703,678, Non Final Office Action mailed Apr. 8, 2019", 11 pgs.

"U.S. Appl. No. 15/703,678, Notice of Allowance mailed Sep. 17, 2019", 7 pgs.

"U.S. Appl. No. 15/703,678, Preliminary Amendment filed Sep. 28, 2017", 9 pgs.

"U.S. Appl. No. 15/703,678, Response Filed Jan. 3, 2019 to Restriction Requirement Mailed Nov. 5, 2018", 8 pgs.

"U.S. Appl. No. 15/703,678, Response filed Jul. 3, 2019 to Non-Final Office Action mailed Apr. 8, 2019", 20 pgs.

"U.S. Appl. No. 15/703,678, Restriction Requirement mailed Nov. 5, 2018", 6 pgs.

"U.S. Appl. No. 15/703,692, Corrected Notice of Allowability mailed Jul. 8, 2019", 2 pgs.

"U.S. Appl. No. 15/703,692, Non Final Office Action mailed Jan. 14, 2019", 11 pgs.

"U.S. Appl. No. 15/703,692, Notice of Allowance mailed May 7, 2019", 5 pgs.

"U.S. Appl. No. 15/703,692, Preliminary Amendment filed Sep. 28, 2017", 9 pgs.

"U.S. Appl. No. 15/703,692, Response filed Apr. 4, 2019 to Non Final Office Action mailed Jan. 14, 2019", 11 pgs.

"U.S. Appl. No. 15/703,698, Corrected Notice of Allowability mailed Dec. 18, 2018", 2 pgs.

"U.S. Appl. No. 15/703,698, Non Final Office Action mailed Apr. 6, 2018", 7 pgs.

"U.S. Appl. No. 15/703,698, Notice of Allowance mailed Sep. 12, 2018", 5 pgs.

"U.S. Appl. No. 15/703,698, Preliminary Amendment filed Sep. 28, 2017", 8 pgs.

"U.S. Appl. No. 15/703,698, Response filed Jul. 6, 2018 to Non Final Office Action mailed Apr. 6, 2018", 10 pgs.

"U.S. Appl. No. 15/703,713, Non Final Office Action mailed Mar. 27, 2018", 29 pgs.

"U.S. Appl. No. 15/703,713, Notice of Allowance mailed Sep. 25, 2018", 11 pgs.

"U.S. Appl. No. 15/703,713, Response Filed Jun. 15, 2018 to Non-Final Office Action Mailed Mar. 27, 2018", 16 pgs.

"U.S. Appl. No. 15/703,713, Preliminary Amendment filed Sep. 28, 2017", 7 pgs.

"U.S. Appl. No. 15/720,866, Final Office Action mailed Feb. 28, 2020", 10 pgs.

"U.S. Appl. No. 15/720,866, Non Final Office Action mailed Sep. 9, 2019", 12 pgs.

"U.S. Appl. No. 15/720,866, Notice of Allowance mailed Sep. 23, 2020", 7 pgs.

"U.S. Appl. No. 15/720,866, PTO Response to Rule 312 Communication mailed Nov. 20, 2020", 2 pgs.

"U.S. Appl. No. 15/720,866, Response filed Jan. 9, 2020 to Non Final Office Action mailed Sep. 9, 2019", 11 pgs.

"U.S. Appl. No. 15/720,866, Response filed May 27, 2020 to Final Office Action mailed Feb. 28, 2020", 13 pgs.

"U.S. Appl. No. 15/720,866, Response filed Jul. 10, 2019 to Restriction Requirement mailed May 14, 2019", 10 pgs.

"U.S. Appl. No. 15/720,866, Response filed Nov. 13, 2017 to Non Final Office Action mailed Sep. 14, 2017", 10 pgs.

"U.S. Appl. No. 15/720,866, Restriction Requirement mailed May 14, 2019", 7 pgs.

"U.S. Appl. No. 15/720.866, Preliminary Amendment filed Nov. 13, 2017", 9 pgs.

"U.S. Appl. No. 15/827,654, Examiner Interview Summary mailed Apr. 26, 2019", 4 pgs.

"U.S. Appl. No. 15/827,654, Final Office Action mailed Feb. 19, 2019", 19 pgs.

"U.S. Appl. No. 15/827,654, Non Final Office Action mailed Sep. 7, 2018", 21 pgs.

"U.S. Appl. No. 15/827,654, Notice of Allowance mailed Jul. 8, 2019", 8 pgs.

"U.S. Appl. No. 15/827,654, Preliminary Amendment filed Dec. 22, 2017", 11 pgs.

"U.S. Appl. No. 15/827,654, Response Filed May 20, 2019 to Final Office Action Mailed Feb. 19, 2019", 17 pgs.

"U.S. Appl. No. 15/827,654, Response filed Jun. 6, 2018 to Restriction Requirement mailed Apr. 6, 2018", 11 pgs.

"U.S. Appl. No. 15/827,654, Response filed to Non Final Office Action mailed Sep. 7, 2018", 24 pgs.

(56) References Cited

OTHER PUBLICATIONS

"U.S. Appl. No. 15/827,654, Restriction Requirement mailed Apr. 6, 2018", 6 pgs.

"U.S. Appl. No. 15/890,735, Notice of Allowance mailed Oct. 29, 2019", 11 pgs.

"U.S. Appl. No. 15/915,886, Non Final Office Action mailed Aug. 2, 2019", 9 pgs.

"U.S. Appl. No. 15/915,886, Notice of Allowance mailed Jan. 16, 2020", 9 pgs.

"U.S. Appl. No. 15/915,886, PTO Response to Rule 312 Communication mailed May 8, 2020", 2 pgs.

"U.S. Appl. No. 15/915,886, Response Filed Nov. 4, 2019 to Non-Final Office Action Mailed Aug. 2, 2019", 8 pgs.

"U.S. Appl. No. 15/971,743, Notice of Allowance mailed Aug. 6, 2019", 8 pgs.

"U.S. Appl. No. 16/179,201, Advisory Action mailed Jun. 25, 2021", 3 pgs.

"U.S. Appl. No. 16/179,201, Examiner Interview Summary mailed Feb. 8, 2021", 3 pgs.

"U.S. Appl. No. 16/179,201, Examiner Interview Summary mailed Nov. 9, 2021", 4 pgs.

"U.S. Appl. No. 16/179,201, Examiner Interview Summary mailed Nov. 17, 2021", 3 pgs.

"U.S. Appl. No. 16/179,201, Final Office Action mailed Apr. 20, 2021", 11 pgs.

"U.S. Appl. No. 16/179,201, Non Final Office Action mailed Sep. 22, 2021", 11 pgs.

"U.S. Appl. No. 16/179,201, Non Final Office Action mailed Nov. 2, 2020", 15 pgs.

"U.S. Appl. No. 16/179,201, Response filed Jan. 28, 2021 to Non Final Office Action mailed Nov. 2, 2020", 16 pgs.

"U.S. Appl. No. 16/179,201, Response filed Jun. 18, 2021 to Final Office Action mailed Apr. 20, 2021", 16 pgs.

"U.S. Appl. No. 16/179,201, Response filed Oct. 5, 2020 to Restriction Requirement mailed Aug. 7, 2020", 9 pgs.

"U.S. Appl. No. 16/179,201, Response filed Dec. 3, 2021 to Non Final Office Action mailed Sep. 22, 2021", 11 pgs.

"U.S. Appl. No. 16/179,201, Restriction Requirement mailed Aug. 7, 2020", 10 pgs.

"U.S. Appl. No. 16/179,201, Supplemental Response filed Feb. 19, 2021 to Non-Final Office Action mailed Nov. 2, 2020", 17 pgs.

"U.S. Appl. No. 16/352,287, Final Office Action mailed May 25, 2021", 8 pgs.

"U.S. Appl. No. 16/352,287, Non Final Office Action mailed Dec. 10, 2020", 12 pgs.

"U.S. Appl. No. 16/352,287, Notice of Allowance mailed Jun. 30, 2021", 7 pgs.

"U.S. Appl. No. 16/352,287, Response filed Feb. 22, 2021 to Non Final Office Action mailed Dec. 10, 2020", 14 pgs.

"U.S. Appl. No. 16/352,287, Response filed Jun. 18, 2021 to Final Office Action mailed May 25, 2021", 8 pgs.

"U.S. Appl. No. 16/352,287, Response filed Oct. 12, 2020 to Restriction Requirement mailed Aug. 17, 2020", 8 pgs.

"U.S. Appl. No. 16/352,287, Restriction Requirement mailed Aug. 17, 2020", 6 pgs.

"U.S. Appl. No. 16/389,381, Non Final Office Action mailed Mar. 30, 2020", 9 pgs.

"U.S. Appl. No. 16/389,381, Notice of Allowance mailed Jul. 16, 2020", 5 pgs.

"U.S. Appl. No. 16/389,381, Response filed Jun. 19, 2020 to Non Final Office Action mailed Mar. 30, 2020", 9 pgs.

"U.S. Appl. No. 16/530,423, Final Office Action mailed Nov. 4, 2021", 11 pgs.

"U.S. Appl. No. 16/530,423, Non Final Office Action mailed Mar. 3, 2022", 14 pgs.

"U.S. Appl. No. 16/530,423, Non Final Office Action mailed May 17, 2021", 10 pgs.

"U.S. Appl. No. 16/530,423, Preliminary Amendment filed Aug. 28, 2019", 7 pgs.

"U.S. Appl. No. 16/530,423, Response filed Feb. 4, 2022 to Final Office Action mailed Nov. 4, 2021", 15 pgs.

"U.S. Appl. No. 16/530,423, Response filed Aug. 11, 2021 to Non Final Office Action mailed May 17, 2021", 15 pgs.

"U.S. Appl. No. 16/596,194, Amendment Under 1.312 Filed Dec. 7, 2021", 9 pgs.

"U.S. Appl. No. 16/596,194, Final Office Action mailed May 20, 2021", 21 pgs.

"U.S. Appl. No. 16/596,194, Non Final Office Action mailed Jan. 22, 2021", 19 pgs.

"U.S. Appl. No. 16/596,194, Notice of Allowance mailed Sep. 9, 2021", 10 pgs.

"U.S. Appl. No. 16/596,194, Preliminary Amendment Filed Nov. 14, 2019", 8 pgs.

"U.S. Appl. No. 16/596,194, PTO Response to Rule 312 Communication mailed Dec. 13, 2021", 2 pgs.

"U.S. Appl. No. 16/596,194, Response filed Apr. 12, 2021 to Non Final Office Action mailed Jan. 22, 2021", 15 pgs.

"U.S. Appl. No. 16/596,194, Response filed Aug. 18, 2021 to Final Office Action mailed May 20, 2021", 15 pgs.

"U.S. Appl. No. 16/715,092, Final Office Action mailed Mar. 16, 2022", 8 pgs.

"U.S. Appl. No. 16/715,092, Non Final Office Action mailed Sep. 22, 2021", 8 pgs.

"U.S. Appl. No. 16/715,092, Preliminary Amendment filed Mar. 19, 2020", 10 pgs.

"U.S. Appl. No. 16/715,092, Response filed Aug. 9, 2021 to Restriction Requirement mailed Jun. 25, 2021", 7 pgs.

"U.S. Appl. No. 16/715,092, Response filed Dec. 10, 2021 to Non Final Office Action mailed Sep. 22, 2021", 14 pgs.

"U.S. Appl. No. 16/715,092, Restriction Requirement mailed Jun. 25, 2021", 6 pgs.

"U.S. Appl. No. 16/743,746, Notice of Allowance mailed Jan. 13, 2022", 14 pgs.

"U.S. Appl. No. 16/743,746, Preliminary Amendment filed Mar. 19, 2020", 8 pgs.

"U.S. Appl. No. 16/743,746, Supplemental Notice of Allowability mailed Jan. 27, 2022", 2 pgs.

"U.S. Appl. No. 16/849,394, Preliminary Amendment filed Jun. 3, 2020", 7 pgs.

"U.S. Appl. No. 17/068,435, Preliminary Amendment filed Nov. 13, 2020", 7 pgs.

"U.S. Appl. No. 17/134,885, Preliminary Amendment filed Jan. 18, 2021", 10 pgs.

"U.S. Appl. No. 17/545,728, Preliminary Amendment filed Jan. 7, 2022", 10 pgs.

"Australian Application Serial No. 2011286306, First Examiner Report mailed Jun. 19, 2013", 4 pgs.

"Australian Application Serial No. 2011286306, Response filed Jun. 3, 2014 to First Examiner Report mailed Jun. 19, 2013", 16 pgs.

"Australian Application Serial No. 2011286307, First Examiner Report mailed Oct. 17, 2013", 2 pgs.

"Australian Application Serial No. 2011286307, Response filed May 21, 2014 to First Examiner Report mailed Oct. 17, 2013", 16 pgs.

"Australian Application Serial No. 2011286308, First Examiner Report mailed Jun. 21, 2013", 4 pgs.

"Australian Application Serial No. 2011286308, Response filed Jun. 6, 2014 First Examiner Report mailed Jun. 21, 2013", 19 pgs.

"Australian Application Serial No. 2011286309, First Examiner Report mailed Jun. 21, 2013", 3 pgs.

"Australian Application Serial No. 2011286309, Response filed Jun. 10, 2014 to First Examiner Report mailed Jun. 21, 2013", 4 pgs.

"Australian Application Serial No. 2011343440, First Examiner Report mailed Feb. 17, 2014", 3 pgs.

"Australian Application Serial No. 2011343440, Response filed Mar. 21, 2014 to Office Action mailed Feb. 17, 2014", 1 pg.

"Australian Application Serial No. 2012271243, Office Action mailed Apr. 1, 2015", 2 pgs.

"Australian Application Serial No. 2012271243, Response filed Apr. 8, 2015 to Office Action mailed Apr. 1, 2015", 4 pgs.

"Australian Application Serial No. 2012271243, Response filed Apr. 15, 2015 to Office Action mailed Apr. 13, 2015", 1 pg.

(56)            References Cited

OTHER PUBLICATIONS

"Australian Application Serial No. 2012271243, Subsequent Examiners Report mailed Apr. 13, 2015", 2 pgs.

"Australian Application Serial No. 2012341026, First Examiner Report mailed Jul. 14, 2014", 2 pgs.

"Australian Application Serial No. 2012341026, Response filed Nov. 21, 2014 to First Examiner Report mailed Jul. 14, 2014", 1 pg.

"Australian Application Serial No. 2012341026, Statement of Proposed Amendment filed Jun. 18, 2014", 25 pgs.

"Australian Application Serial No. 2012368262, First Examiner Report mailed Nov. 2, 2016", 4 pgs.

"Australian Application Serial No. 2012368262, Response filed Jan. 17, 2017 to Office Action mailed Nov. 2, 2016", 21 pgs.

"Australian Application Serial No. 2012368262, Response filed May 15, 2017 to Subsequent Examiners Report mailed Mar. 16, 2017", 2 pgs.

"Australian Application Serial No. 2012368262, Subsequent Examiners Report mailed Mar. 16, 2017", 3 pgs.

"Australian Application Serial No. 2013238046, First Examiner Report mailed Nov. 26, 2015", 2 pgs.

"Australian Application Serial No. 2013238046, Response filed Feb. 2, 2016 to First Examiner Report mailed Nov. 26, 2015", 1 pg.

"Australian Application Serial No. 2013238054, First Examiner Report mailed Oct. 17, 2016", 4 pgs.

"Australian Application Serial No. 2013238054, Response filed Jan. 18, 2017 to First Examiner Report mailed Oct. 17, 2016", 9 pgs.

"Australian Application Serial No. 2014250709, First Examiner Report mailed Dec. 21, 2015", 3 pgs.

"Australian Application Serial No. 2014250709, Response filed May 4, 2016 to First Examiner Report mailed Dec. 21, 2015", 12 pgs.

"Australian Application Serial No. 2014250709, Subsequent Examiners Report mailed May 31, 2016", 6 pgs.

"Australian Application Serial No. 2014250710, First Examiner Report mailed Dec. 11, 2015", 7 pgs.

"Australian Application Serial No. 2014250710, Response filed Mar. 22, 2016 to First Examiner Report mailed Dec. 11, 2015", 18 pgs.

"Australian Application Serial No. 2014250710, Response filed May 4, 2016 to Subsequent Examiners Report mailed Mar. 23, 2016", 15 pgs.

"Australian Application Serial No. 2014250710, Subsequent Examiners Report mailed Mar. 23, 2016", 3 pgs.

"Australian Application Serial No. 2014250711, First Examiner Report mailed Feb. 12, 2016", 7 pgs.

"Australian Application Serial No. 2014250711, Response filed Apr. 27, 2016 to First Examiner Report mailed Feb. 12, 2016", 32 pgs.

"Australian Application Serial No. 2015201511, First Examination Report mailed Apr. 18, 2016", 2 pgs.

"Australian Application Serial No. 2015201511, Response filed Jun. 30, 2016 to First Examiner Report mailed Apr. 18, 2016", 12 pgs.

"Australian Application Serial No. 2015238820, First Examination Report mailed May 30, 2017", 3 pgs.

"Australian Application Serial No. 2015238820, Response filed Jul. 12, 2017 to First Examination Report mailed May 30, 2017", 12 pgs.

"Australian Application Serial No. 2016225911, First Examiners Report mailed Jun. 2, 2017", 3 pgs.

"Australian Application Serial No. 2016225911, Response filed Aug. 22, 2017 to First Examiners Report mailed Jun. 2, 2017", 18 pgs.

"Australian Application Serial No. 2017235987, First Examination Report mailed Nov. 1, 2018", 4 pgs.

"Australian Application Serial No. 2017251736, First Examiners Report mailed Oct. 31, 2017", 2 pgs.

"Australian Application Serial No. 2018266322, First Examination Report mailed Dec. 19, 2019", 2 pgs.

"Australian Application Serial No. 2020204019, First Examination Report mailed Jun. 18, 2021", 7 pgs.

"Australian Application Serial No. 2020204019, Response filed Jan. 11, 2022 to Subsequent Examiners Report mailed Nov. 16, 2021", 19 pgs.

"Australian Application Serial No. 2020204019, Response filed Aug. 19, 2021 to First Examination Report mailed Jun. 18, 2021", 3 pgs.

"Australian Application Serial No. 2020204019, Subsequent Examiners Report mailed Sep. 2, 2021", 4 pgs.

"Australian Application Serial No. 2020204019, Subsequent Examiners Report mailed Nov. 16, 2021", 3 pgs.

"Bi-Cruciate Stabilized Knee System", Design Rationale, Smith & Nephew Journal, (2006), 20 pgs.

"Brazil Application Serial No. BR1120130016698, Office Action mailed Aug. 27, 2019", (W/ English Translation), 8 pages.

"Brazil Application Serial No. BR1120130016698, Response filed Dec. 9, 2019 to Office Action mailed Aug. 27, 2019", w/ English Claims, 22 pgs.

"Brazil Application Serial No. BR1120130016736, Office Action mailed Aug. 27, 2019", (with English translation), 8 pages.

"Brazil Application Serial No. BR1120130016736, Response filed Dec. 9, 2019 to Office Action mailed Aug. 27, 2019", w/ English Claims, 25 pgs.

"Brazilian Application Serial No. BR1120130016736, Response filed Oct. 5, 2020 to Office Action mailed Jun. 10, 2020", (W/ English Translation of Claims), 91 pgs.

"Canadian Application Serial No. 2,806,321, Office Action mailed Jan. 15, 2018", 3 pgs.

"Canadian Application Serial No. 2,806,321, Response filed Jan. 22, 2018 to Office Action mailed Jan. 15, 2018", 7 pgs.

"Canadian Application Serial No. 2,806,321, Response filed Dec. 6, 2017 to Office Action mailed Jun. 15, 2017", 12 pgs.

"Canadian Application Serial No. 2,806,325, Office Action mailed Mar. 14, 2016", 4 pgs.

"Canadian Application Serial No. 2,806,325, Response filed Sep. 14, 2016 to Office Action mailed Mar. 14, 2016", 17 pgs.

"Canadian Application Serial No. 2,806,326, Examiner's Rule 30(2) Requisition mailed Sep. 20, 2018", 4 pgs.

"Canadian Application Serial No. 2,806,326, Office Action mailed Feb. 8, 2018", 4 pgs.

"Canadian Application Serial No. 2,806,326, Office Action mailed Jun. 19, 2017", 3 pgs.

"Canadian Application Serial No. 2,806,326, Response Filed Mar. 20, 2019 to Examiner's Rule 30(2) Requisition mailed Sep. 20, 2018", 4 pgs.

"Canadian Application Serial No. 2,806,326, Response filed Jul. 20, 2018 to Office Action mailed Feb. 8, 2018", 12 pgs.

"Canadian Application Serial No. 2,821,927, Office Action mailed Jan. 25, 2018", 6 pgs.

"Canadian Application Serial No. 2,821,927, Response filed Jul. 18, 2018 to Office Action mailed Jan. 25, 2018", 10 pgs.

"Canadian Application Serial No. 2,821,927, Voluntary Amendment mailed Jun. 14, 2013", 7 pgs.

"Canadian Application Serial No. 2,824,527, Office Action mailed Mar. 17, 2014", 2 pgs.

"Canadian Application Serial No. 2,824,527, Response filed Sep. 17, 2014 to Office Action mailed Mar. 17, 2014", 14 pgs.

"Canadian Application Serial No. 2,856,070, Preliminary Amendment filed May 25, 2015", 27 pgs.

"Canadian Application Serial No. 2,856,571 Response filed Jan. 22, 2015 to Office Action mailed Jul. 22, 2014", 24 pgs.

"Canadian Application Serial No. 2,856,571, Office Action mailed Jul. 22, 2014", 2 pgs.

"Canadian Application Serial No. 2,863,375, Office Action mailed Apr. 20, 2018", 3 pgs.

"Canadian Application Serial No. 2,863,375, Response filed Oct. 22, 2018 Office Action mailed Apr. 20, 2018", 12 pgs.

"Canadian Application Serial No. 2,868,825, Office Action mailed Dec. 27, 2018", 3 pgs.

"Canadian Application Serial No. 2,956,119, Examiner's Rule 30(2) Requisition mailed Sep. 27, 2018", 4 pgs.

"Canadian Application Serial No. 2,956,119, Office Action mailed Jan. 22, 2018", 3 pgs.

(56)          References Cited

OTHER PUBLICATIONS

"Canadian Application Serial No. 2,956,119, Response Filed Mar. 27, 2019 to Examiner's Rule 30(2) Requisition mailed Sep. 27, 2018", 7 pgs.

"Canadian Application Serial No. 2,989,184, Office Action mailed Oct. 1, 2018", 4 pgs.

"Canadian Application Serial No. 2,989,184, Response filed Apr. 1, 2019 to Office Action mailed Oct. 1, 2018", 10 pgs.

"Canadian Application Serial No. 3,063,415, Office Action mailed Jul. 13, 2020", 3 pgs.

"Canadian Application Serial No. 3,063,415, Response filed Nov. 12, 2020 to Office Action mailed Jul. 13, 2020", 15 pgs.

"Canadian Application Serial No. 2,806,321, Office Action mailed Jun. 15, 2017", 3 pgs.

"Chinese Application Serial No. 201180045673.3, Office Action mailed Feb. 14, 2016", (W/ English Translation), 17 pgs.

"Chinese Application Serial No. 201180045673.3, Office Action mailed Mar. 29, 2015", (W/ English Translation), 6 pgs.

"Chinese Application Serial No. 201180045673.3, Office Action mailed Aug. 12, 2015", (W/ English Translation), 7 pgs.

"Chinese Application Serial No. 201180045673.3, Response filed Jun. 19, 2015 to Office Action mailed Mar. 29, 2015", (W/ English translation of claims), 11 pgs.

"Chinese Application Serial No. 201180045673.3, Response filed Oct. 27, 2015 to Office Action mailed Aug. 12, 2015", (W/ English translation of claims), 9 pgs.

"Chinese Application Serial No. 201180045681.8, Office Action mailed Jan. 22, 2015", (W/ English Translation), 11 pgs.

"Chinese Application Serial No. 201180045681.8, Response filed May 14, 2015 to Office Action mailed Jan. 22, 2015", W/ English Claims, 17 pgs.

"Chinese Application Serial No. 201180045683.7, Office Action mailed Mar. 9, 2015", (W/ English Translation), 6 pgs.

"Chinese Application Serial No. 201180045683.7, Response filed Jul. 14, 2015 to Office Action mailed Mar. 9, 2015", (W/ English translation of claims), 30 pgs.

"Chinese Application Serial No. 201180045689.4, Office Action mailed Jan. 5, 2015", (W/ English Translation), 4 pgs.

"Chinese Application Serial No. 201180045689.4, Office Action mailed Feb. 2, 2016", w/English Translation, 11 pgs.

"Chinese Application Serial No. 201180045689.4, Office Action mailed Aug. 5, 2015", (W/ English Translation), 11 pgs.

"Chinese Application Serial No. 201180045689.4, Response filed May 1, 2015 to Office Action mailed Jan. 5, 2015", W/ English Claims, 13 pgs.

"Chinese Application Serial No. 201180067430.X, Office Action mailed Aug. 28, 2014", (W/ English Translation), 8 pgs.

"Chinese Application Serial No. 201180067430.X, Response filed Jan. 4, 2015 to Office Action mailed Sep. 26, 2014", (W/ English Translation), 14 pgs.

"Chinese Application Serial No. 201180067757.7, Office Action mailed Mar. 2, 2015", (W/ English Translation), 18 pgs.

"Chinese Application Serial No. 201180067757.7, Office Action mailed Jun. 1, 2016", (W/ English Translation), 10 pgs.

"Chinese Application Serial No. 201180067757.7, Office Action mailed Nov. 16, 2015", (W/ English Translation), 17 pgs.

"Chinese Application Serial No. 201180067757.7, Response filed Jan. 27, 2016 to Office Action mailed Nov. 16, 2015", (W/ English Translation of Claims), 12 pgs.

"Chinese Application Serial No. 201180067757.7, Response filed Jul. 10, 2015 to Office Action mailed Mar. 2, 2015", (W/ English Translation), 13 pgs.

"Chinese Application Serial No. 201180067757.7, Response filed Aug. 11, 2016 to Office Action mailed Jun. 1, 2016", (W/ English Translation Of Claims), 9 pgs.

"Chinese Application Serial No. 201180067757.7, Voluntary Amendment mailed Feb. 14, 2014", (W/ English Translation of Claims), 8 pgs.

"Chinese Application Serial No. 201280067473.2, Office Action mailed Feb. 1, 2016", (W/ English Translation), 4 pgs.

"Chinese Application Serial No. 201280067473.2, Office Action mailed May 20, 2015", (W/ English Translation), 15 pgs.

"Chinese Application Serial No. 201280067473.2, Office Action mailed Nov. 20, 2015", W/ English Translation of Claims, 7 pgs.

"Chinese Application Serial No. 201280067473.2, Response filed Apr. 7, 2016 to Office Action mailed Feb. 1, 2016", (W/ English translation of claims), 11 pgs.

"Chinese Application Serial No. 201280067473.2, Response filed Sep. 7, 2015 to Office Action mailed May 20, 2015", (W/ English translation of claims), 12 pgs.

"Chinese Application Serial No. 201280067473.2, Response filed Dec. 4, 2015 to Office Action mailed Nov. 20, 2015", w/English Claims, 11 pgs.

"Chinese Application Serial No. 201280067481.7, Office Action mailed Sep. 30, 2015", (W/ English Translation), 7 pgs.

"Chinese Application Serial No. 201280071940.9, Office Action mailed Jul. 22, 2015", (W/ English Translation), 13 pgs.

"Chinese Application Serial No. 201280071940.9, Preliminary Amendment filed Mar. 23, 2015", W/ English Claims, 11 pgs.

"Chinese Application Serial No. 201380028572.4, Office Action mailed Aug. 13, 2015", (W/ English Translation), 16 pgs.

"Chinese Application Serial No. 201380028683.5, Office Action mailed Jun. 27, 2016", (W/ English Translation), 8 pgs.

"Chinese Application Serial No. 201380028683.5, Office Action mailed Nov. 4, 2015", (W/ English Translation), 16 pgs.

"Chinese Application Serial No. 201380028683.5, Office Action mailed Dec. 30, 2016", (W/ English Translation), 4 pgs.

"Chinese Application Serial No. 201380028683.5, Response filed Feb. 8, 2017 to Office Action mailed Dec. 30, 2016", (W/ English Translation), 13 pgs.

"Chinese Application Serial No. 201380028683.5, Response filed Mar. 18, 2016 to Office Action mailed Nov. 4, 2015", (W/ English Translation of Claims), 11 pgs.

"Chinese Application Serial No. 201380028683.5, Response filed Sep. 6, 2016 to Office Action mailed Jun. 27, 2016", (W/ English Translation of Claims), 11 pgs.

"Chinese Application Serial No. 201510394094.X, Office Action mailed May 24, 2017", (W/ English Translation), 11 pgs.

"Chinese Application Serial No. 201510394094.X, Office Action mailed Aug. 30, 2016", (W/ English Translation), 14 pgs.

"Chinese Application Serial No. 201510394094.X, Office Action mailed Nov. 3, 2017", (W/ English Translation), 10 pgs.

"Chinese Application Serial No. 201510394094.X, Response filed Jan. 16, 2017 to Office Action mailed Aug. 30, 2016", (W/ English Translation of Claims), 11 pgs.

"Chinese Application Serial No. 201510394094.X, Response filed Jan. 18, 2018 to Office Action mailed Nov. 3, 2017", (W/ English Claims), 10 pgs.

"Chinese Application Serial No. 201510394094.X, Response filed Jul. 10, 2017 to Office Action mailed May 24, 2017", (W/ English Translation), 10 pgs.

"Chinese Application Serial No. 201510640436.1, Office Action mailed Sep. 28, 2016", (W/ English Translation), 13 pgs.

"Chinese Application Serial No. 201510640436.1, Response filed Feb. 16, 2017 to Office Action mailed Sep. 28, 2016", (W/ English Translation), 18 pgs.

"Chinese Application Serial No. 201610634595.5, Office Action mailed Apr. 20, 2018", (W/ English Translation), 8 pgs.

"Chinese Application Serial No. 201610634595.5, Office Action mailed Jun. 21, 2017", w/English Translation, 9 pgs.

"Chinese Application Serial No. 201610634595.5, Response filed Jun. 4, 2018 to Office Action mailed Apr. 20, 2018", (W/ English Translation of Claims), 8 pgs.

"Chinese Application Serial No. 201610634595.5, Response filed Nov. 3, 2017 to Office Action mailed Jun. 21, 2017", w/English Claims, 8 pgs.

"Chinese Application Serial No. 201610685172.6, Office Action mailed Apr. 10, 2017", (W/ English Translation), 11 pgs.

"Chinese Application Serial No. 201610685172.6, Office Action mailed Sep. 28, 2017", (W/ English Translation), 9 pgs.

"Chinese Application Serial No. 201610685172.6, Response filed Dec. 13, 2017 to Office Action mailed Sep. 28, 2017", (W/ English Claims), 13 pgs.

(56) References Cited

OTHER PUBLICATIONS

"Chinese Application Serial No. 201680061268.3, Office Action mailed Apr. 24, 2019", (W/ English Translation), 11 pgs.
"Chinese Application Serial No. 201680061268.3, Response filed Aug. 21, 2019 to Office Action mailed Apr. 24, 2019", (W/ English Claims), 8 pgs.
"Chinese Application Serial No. 201880016775.4, Decision of Rejection mailed Jul. 12, 2021", (W/ English Translation), 13 pgs.
"Chinese Application Serial No. 201880016775.4, Office Action mailed Jan. 22, 2021", with English translation, 15 pages.
"Chinese Application Serial No. 201880031319.7, Office Action mailed May 15, 2020", (W/ English Translation), 12 pgs.
"Chinese Application Serial No. 201880031319.7, Office Action mailed Nov. 18, 2020", (W/ English Translation), 9 pgs.
"Chinese Application Serial No. 201880031319.7, Response filed Jan. 18, 2021 to Office Action mailed Nov. 18, 2020", (W/ English Claims), 16 pgs.
"Chinese Application Serial No. 201880031319.7, Response filed Jul. 22, 2020 to Office Action mailed May 15, 2020", (W/ English Claims), 10 pgs.
"Complete Knee Solution Surgical Technique for the CR-Flex Fixed Bearing Knee", Zimmer Nexgen, (2003), 22 pgs.
"European Application Serial No. 11738918.9, Examination Notification Art. 94(3) mailed Oct. 23, 2014", 5 pgs.
"European Application Serial No. 11738918.9, Preliminary Amendment mailed Sep. 24, 2013", 11 pgs.
"European Application Serial No. 11738918.9, Response filed Mar. 2, 2015 to Examination Notification Art. 94(3) mailed Oct. 23, 2014", 14 pgs.
"European Application Serial No. 11738919.7, Examination Notification Art. 94(3) mailed Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) mailed Jul. 7, 2014", 14 pgs.
"European Application Serial No. 11738920.5, Communication Pursuant to Article 94(3) EPC mailed Mar. 15, 2016", 4 pgs.
"European Application Serial No. 11738920.5, Preliminary Amendment Sep. 24, 2013", 9 pgs.
"European Application Serial No. 11738920.5, Response filed Jul. 25, 2016 to Communication Pursuant to Article 94(3) EPC mailed Mar. 15, 2016", 6 pgs.
"European Application Serial No. 11738920.5, Response filed Sep. 24, 2013 to Communication pursuant to Rules 161(2) and 162 EPC mailed Mar. 15, 2013", 22 pgs.
"European Application Serial No. 11758060.5, Communication Pursuant to Article 94(3) EPC mailed Jul. 12, 2016", 3 pgs.
"European Application Serial No. 11758060.5, Communication Pursuant to Article 94(3) EPC mailed Dec. 11, 2015", 4 pgs.
"European Application Serial No. 11758060.5, Preliminary Amendment filed Nov. 4, 2013", 15 pgs.
"European Application Serial No. 11758060.5, Response filed Apr. 21, 2016 to Communication Pursuant to Article 94(3) EPC mailed Dec. 11, 2015", 16 pgs.
"European Application Serial No. 11758060.5, Response filed Nov. 15, 2016 to Communication Pursuant to Article 94(3) EPC mailed Jul. 12, 2016", 23 pgs.
"European Application Serial No. 11802835.6, Communication Pursuant to Article 94(3) EPC mailed Dec. 11, 2017", 4 pgs.
"European Application Serial No. 11802835.6, Response filed Apr. 23, 2018 to Office Action mailed Dec. 11, 2017", 16 pgs.
"European Application Serial No. 11808493.8, Communication Pursuant to Article 94(3) EPC mailed Dec. 7, 2015", 4 pgs.
"European Application Serial No. 11808493.8, Examination Notification Art. 94(3) mailed Feb. 20, 2015", 6 pgs.
"European Application Serial No. 11808493.8, Response filed Feb. 26, 2014 to Communication pursuant to Rules 161(1) and 162 EPC mailed Aug. 16, 2013", 14 pgs.

"European Application Serial No. 11808493.8, Response filed Apr. 18, 2016 to Communication Pursuant to Article 94(3) EPC mailed Dec. 7, 2015", 15 pgs.
"European Application Serial No. 11808493.8, Response filed Jul. 2, 2015 to Examination Notification Art. 94(3) mailed Feb. 20, 2015", 13 pgs.
"European Application Serial No. 11815029.1, Communication Pursuant to Article 94(3) EPC mailed Sep. 29, 2016", 4 pgs.
"European Application Serial No. 11815029.1, Extended European Search Report mailed Dec. 10, 2013", 8 pgs.
"European Application Serial No. 11815029.1, Response filed Apr. 10, 2017 to Communication Pursuant to Article 94(3) EPC mailed Sep. 29, 2016", 22 pgs.
"European Application Serial No. 11815029.1, Response filed Jul. 21, 2014 Extended European Search Report mailed Dec. 10, 2013", 15 pgs.
"European Application Serial No. 12718882.9, Communication Pursuant to Article 94(3) EPC mailed Dec. 1, 2015", 11 pgs.
"European Application Serial No. 12718882.9, Response filed Feb. 10, 2015 to Communication Pursuant to Rules 161(1) and 162 EPC mailed Jul. 31, 2014", 11 pgs.
"European Application Serial No. 12718882.9, Response filed Apr. 11, 2016 to Communication Pursuant to Article 94(3) EPC mailed Dec. 1, 2015", 12 pgs.
"European Application Serial No. 12718883.7, Communication Pursuant to Article 94(3) EPC mailed Dec. 2, 2015", 4 pgs.
"European Application Serial No. 12718883.7, Communication Pursuant to Rules 161(1) and 162 EPC mailed Jul. 31, 2014", 2 pgs.
"European Application Serial No. 12718883.7, Intention to Grant mailed May 20, 2016", 5 pgs.
"European Application Serial No. 12718883.7, Response filed Feb. 10, 2015 to Communication Pursuant to Rules 161(1) and 162 EPC mailed Jul. 31, 2014", 16 pgs.
"European Application Serial No. 12718883.7, Response filed Apr. 12, 2016 to Communication Pursuant to Article 94(3) EPC mailed Dec. 2, 2015", 30 pgs.
"European Application Serial No. 12719236.7 Response filed Feb. 9, 2015 to Communication Pursuant to Rules 161(1) and 162 EPC mailed Jul. 30, 2014", 10 pgs.
"European Application Serial No. 12719236.7, Decision to Grant mailed Feb. 18, 2016", 3 pgs.
"European Application Serial No. 12719236.7, Office Action mailed Aug. 27, 2015", 7 pgs.
"European Application Serial No. 12720352.9 Response filed Feb. 9, 2015 to Communication Pursuant to Rules 161(1) and 162 EPC mailed Jul. 30, 2014", 10 pgs.
"European Application Serial No. 12756058.9, Communication Pursuant to Article 94(3) EPC mailed Feb. 18, 2019", 4 pgs.
"European Application Serial No. 12756058.9, Office Action mailed Jan. 17, 2017", 5 Pgs.
"European Application Serial No. 12756058.9, Preliminary Amendment filed Apr. 20, 2015", 12 pgs.
"European Application Serial No. 12756058.9, Response filed May 26, 2017 to Office Action mailed Jan. 17, 2017", 16 pgs.
"European Application Serial No. 12756058.9, Response filed Jun. 28, 2019 to Communication Pursuant to Article 94(3) EPC mailed Feb. 18, 2019", 21 pgs.
"European Application Serial No. 12756869.9 Response filed Feb. 10, 2015 to Communication Pursuant to Rule 161(1) and 162 EPC mailed Jul. 31, 2014", 14 pgs.
"European Application Serial No. 12756869.9, Examination Notification Art. 94(3) mailed Jul. 2, 2015", 4 pgs.
"European Application Serial No. 12756869.9, Response filed Nov. 12, 2015 to Examination Notification Art. 94(3) mailed Jul. 2, 2015", 28 pgs.
"European Application Serial No. 13716636.9, Communication Pursuant to Article 94(3) EPC mailed Nov. 16, 2015", 4 pgs.
"European Application Serial No. 13716636.9, Communication Pursuant to Article 94(3) EPC mailed Nov. 17, 2016", 4 pgs.
"European Application Serial No. 13716636.9, Communication Pursuant to Article 94(3) EPC mailed Jun. 6, 2016", 5 pgs.

(56)                References Cited

OTHER PUBLICATIONS

"European Application Serial No. 13716636.9, Communication pursuant to Rules 161(1) and 162 EPC mailed Dec. 12, 2014", 2 pgs.

"European Application Serial No. 13716636.9, Response filed Mar. 24, 2016 to Communication Pursuant to Article 94(3) EPC mailed Nov. 16, 2015", 18 pgs.

"European Application Serial No. 13716636.9, Response filed Mar. 27, 2017 to Communication Pursuant to Article 94(3) EPC mailed Nov. 17, 2016", 15 pgs.

"European Application Serial No. 13716636.9, Response filed Jun. 22, 2015 to Communication pursuant to Rules 161(1) and 162 EPC mailed Dec. 12, 2014", 10 pgs.

"European Application Serial No. 13716636.9, Response filed Oct. 17, 2016 to Communication Pursuant to Article 94(3) EPC mailed Jun. 6, 2016", 5 pgs.

"European Application Serial No. 14190180.1, Extended European Search Report mailed Sep. 24, 2015", 8 pgs.

"European Application Serial No. 15160934.4, Communication Pursuant to Article 94(3) EPC mailed Apr. 26, 2018", 5 pgs.

"European Application Serial No. 15160934.4, Extended European Search Report mailed Jun. 1, 2016", 8 pgs.

"European Application Serial No. 15160934.4, Response filed Aug. 30, 18 to Communication Pursuant to Article 94(3) EPC mailed Apr. 26, 2018", 63 pgs.

"European Application Serial No. 15160934.4, Response filed Dec. 21, 2016 to Extended European Search Report mailed Jun. 1, 2016", 5 pgs.

"European Application Serial No. 15174394.5, Extended European Search Report mailed Mar. 21, 2016", 8 pgs.

"European Application Serial No. 15174394.5, Response filed Nov. 18, 2016 to Extended European Search Report mailed Mar. 21, 2016", 12 pgs.

"European Application Serial No. 15191781.2, Communication Pursuant to Article 94(3) EPC mailed Jan. 8, 2018", 4 pgs.

"European Application Serial No. 15191781.2, Extended European Search Report mailed Mar. 1, 2017", 8 pgs.

"European Application Serial No. 15191781.2, Response filed May 17, 2018 to Communication Pursuant to Article 94(3) EPC mailed Jan. 8, 2018", 58 pgs.

"European Application Serial No. 15191781.2, Response filed Sep. 28, 2017 to Extended European Search Report mailed Mar. 1, 2017", 14pgs.

"European Application Serial No. 16156228.5, Extended European Search Report mailed May 11, 2017", 5 pgs.

"European Application Serial No. 16183635.8, Extended European Search Report mailed Jun. 30, 2017", 9 pgs.

"European Application Serial No. 16183635.8, Response filed Mar. 27, 2018 to Extended European Search Report mailed Jun. 30, 2017", 8 pgs.

"European Application Serial No. 16189084.3, Communication Pursuant to Article 94(3) EPC mailed Jul. 1, 2021", 6 pgs.

"European Application Serial No. 16189084.3, Extended European Search Report mailed Oct. 9, 2017", 9 pgs.

"European Application Serial No. 16189084.3, Response filed May 10, 2018 to Extended European Search Report mailed Oct. 9, 2017", 20 pgs.

"European Application Serial No. 16189084.3, Response filed Nov. 8, 2021 to Communication Pursuant to Article 94(3) EPC mailed Jul. 1, 2021", 61 pgs.

"European Application Serial No. 16770657.1, Communication Pursuant to Article 94(3) EPC mailed May 20, 2019", 3 pgs.

"European Application Serial No. 16770657.1, Response filed Sep. 30, 2019 to Communication Pursuant to Article 94(3) EPC mailed May 20, 2019", 26 pgs.

"European Application Serial No. 16770657.1, Response filed Nov. 26, 2018 to Office Action mailed May 14, 2018", 17 pgs.

"European Application Serial No. 17157909.7, Extended European Search Report mailed Jul. 17, 2018", 7 pgs.

"European Application Serial No. 17157909.7, Response Filed Feb. 15, 2019 to Extended European Search Report mailed Jul. 17, 2018", 37 pgs.

"European Application Serial No. 17163432.2, Extended European Search Report mailed May 14, 2018", 6 pgs.

"European Application Serial No. 17163440.5, Extended European Search Report mailed Jan. 3, 2019", 16 pgs.

"European Application Serial No. 17163440.5, Partial European Search Report mailed Jul. 23, 2018", 15 pgs.

"European Application Serial No. 17163440.5, Response filed Jul. 22, 2019 to Extended European Search Report mailed Jan. 3, 2019", 14 pgs.

"European Application Serial No. 17168095.2, Extended European Search Report mailed Jun. 8, 2018", 8 pgs.

"European Application Serial No. 17168095.2, Response Filed Jan. 17, 2019 Extended European Search Report mailed Jun. 8, 2018", 29 pgs.

"European Application Serial No. 17168308.9, Extended European Search Report mailed Jun. 13, 2018", 8 pgs.

"European Application Serial No. 17168308.9, Response Filed Jan. 17, 2019 to Extended European Search Report mailed Jun. 13, 2018", 24 pgs.

"European Application Serial No. 18206326.3, Extended European Search Report mailed Apr. 15, 2019", 10 pgs.

"European Application Serial No. 18206326.3, Response filed Nov. 22, 2019 to Extended European Search Report mailed Apr. 15, 2019", 15 pgs.

"European Application Serial No. 18711801.3, Response to Communication pursuant to Rules 161(1) and 162 EPC filed May 7, 2020", 14 pgs.

"European Application Serial No. 18726670.5, Response to Communication pursuant to Rules 161(1) and 162 EPC filed Jul. 20, 2020", 9 pgs.

"European Application Serial No. 19171990.5, Extended European Search Report mailed Oct. 16, 2019", 8 pgs.

"European Application Serial No. 19171990.5, Response filed May 13, 2020 to Extended European Search Report mailed Oct. 16, 2019", 31 pgs.

"European Application Serial No. 20175535.2, Extended European Search Report mailed Aug. 18, 2021", 16 pgs.

"European Application Serial No. 20175535.2, Partial European Search Report mailed May 18, 2021", 18 pgs.

"European Application Serial No. 20175535.2, Response Filed Mar. 15, 2022 to Extended European Search Report mailed Aug. 18, 2021", 31 pgs.

"European Application Serial No. 21178298.2, Extended European Search Report mailed Mar. 1, 2022", 9 pgs.

"Gender Solutions Natural Knee Flex System: Because Men and Women are Different", Zimmer, Inc., (2007, 2009), 6 pg.

"Gender Solutions Natural Knee Flex System: Surgical Technique", Zimmer, Inc., (2007, 2008, 2009), 36 pgs.

"Gender Solutions Natural-Knee Flex System", Zimmer, Inc., (2007, 2009), 6 pgs.

"Indian Application Serial No. 1544/DELNP/2013, Office Action mailed May 21, 2019", (W/ English Translation), 10 pgs.

"Indian Application Serial No. 1544/DELNP/2013, Response filed Nov. 18, 2019 to Office Action mailed May 21, 2019", (W/ English Translation), 34 pgs.

"Indian Application Serial No. 1545/DELNP/2013, Office Action mailed Dec. 9, 2019", (with English translation), 8 pages.

"Indian Application Serial No. 1545/DELNP/2013, Response filed Jun. 9, 2020 to Office Action mailed Dec. 9, 2019", (W/ English Claims), 78 pgs.

"International Application Serial No. PCT/US2011/045077, International Preliminary Report on Patentability mailed Jul. 5, 2012", 23 pgs.

"International Application Serial No. PCT/US2011/045077, International Search Report and Written Opinion mailed Jan. 9, 2012", 15 pgs.

"International Application Serial No. PCT/US2011/045078, International Preliminary Report on Patentability mailed Feb. 7, 2013", 11 pgs.

US 12,667,463 B2

Page 17

(56) References Cited

OTHER PUBLICATIONS

"International Application Serial No. PCT/US2011/045078, International Search Report and Written Opinion mailed Jan. 9, 2012", 14 pgs.
"International Application Serial No. PCT/US2011/045080, International Preliminary Report on Patentability mailed Feb. 7, 2013", 13 pgs.
"International Application Serial No. PCT/US2011/045080, International Search Report mailed Jan. 9, 2012", 7 pgs.
"International Application Serial No. PCT/US2011/045080, Written Opinion mailed Jan. 9, 2012", 11 pgs.
"International Application Serial No. PCT/US2011/045082, International Preliminary Report on Patentability mailed Feb. 7, 2013", 11 pgs.
"International Application Serial No. PCT/US2011/045082, International Search Report mailed Jan. 9, 2012", 5 pgs.
"International Application Serial No. PCT/US2011/045082, Written Opinion mailed Jan 9, 2012", 10 pgs.
"International Application Serial No. PCT/US2011/045083, International Preliminary Report on Patentability mailed Feb. 7, 2013", 8 pgs.
"International Application Serial No. PCT/US2011/045083, International Search Report mailed Dec. 7, 2011", 2 pgs.
"International Application Serial No. PCT/US2011/045083, Written Opinion mailed Dec. 7, 2011", 6 pgs.
"International Application Serial No. PCT/US2011/051021, International Preliminary Report on Patentability mailed Mar. 21, 2013", 8 pgs.
"International Application Serial No. PCT/US2011/051021, International Search Report mailed Nov. 23, 2011", 12 pgs.
"International Application Serial No. PCT/US2011/051021, Written Opinion mailed Nov. 23, 2011", 7 pgs.
"International Application Serial No. PCT/US2011/064435, International Preliminary Report on Patentability mailed Jun. 27, 2013", 9 pgs.
"International Application Serial No. PCT/US2011/064435, Search Report mailed Jun. 21, 2012", 5 pgs.
"International Application Serial No. PCT/US2011/064435, Written Opinion mailed Jun. 21, 2012", 7 pgs.
"International Application Serial No. PCT/US2011/065683, International Preliminary Report on Patentability mailed Jun. 27, 2013", 11 pgs.
"International Application Serial No. PCT/US2011/065683, International Search Report mailed Apr. 24, 2012", 12 pgs.
"International Application Serial No. PCT/US2011/065683, Written Opinion mailed Apr. 24, 2012", 10 pgs.
"International Application Serial No. PCT/US2012/035679, International Preliminary Report on Patentability mailed May 30, 2014", 8 pgs.
"International Application Serial No. PCT/US2012/035679, International Search Report mailed Jun. 8, 2012", 4 pgs.
"International Application Serial No. PCT/US2012/035679, Written Opinion mailed Jun. 8, 2012", 7 pgs.
"International Application Serial No. PCT/US2012/035680, International Preliminary Report on Patentability mailed May 30, 2014", 13 pgs.
"International Application Serial No. PCT/US2012/035680, Search Report mailed Oct. 9, 2012", 7 pgs.
"International Application Serial No. PCT/US2012/035680, Written Opinion mailed Oct. 9, 2012", 11 pgs.
"International Application Serial No. PCT/US2012/035683, International Preliminary Report on Patentability mailed May 30, 2014", 9 pgs.
"International Application Serial No. PCT/US2012/035683, International Search Report and Written Opinion mailed Jun. 5, 2012", 12 pgs.
"International Application Serial No. PCT/US2012/035684, International Preliminary Report on Patentability mailed May 30, 2014", 14 pgs.

"International Application Serial No. PCT/US2012/035684, International Search Report mailed Aug. 8, 2012", 9 pgs.
"International Application Serial No. PCT/US2012/035684, Written Opinion mailed Jun. 8, 2012", 12 pgs.
"International Application Serial No. PCT/US2012/052132, International Preliminary Report on Patentability mailed Jun. 5, 2014", 12 pgs.
"International Application Serial No. PCT/US2012/052132, International Search Report mailed Jan. 10, 2013", 5 pgs.
"International Application Serial No. PCT/US2012/052132, Invitation to Pay Additional Fees and Partial Search Report mailed Nov. 15, 2012", 7 pgs.
"International Application Serial No. PCT/US2012/052132, Written Opinion mailed Jan. 10, 2013", 10 pgs.
"International Application Serial No. PCT/US2012/052340, International Preliminary Report on Patentability mailed Aug. 14, 2014", 8 pgs.
"International Application Serial No. PCT/US2012/052340, Search Report mailed Oct. 12, 2012", 4 pgs.
"International Application Serial No. PCT/US2012/052340, Written Opinion mailed Oct. 12, 2012", 6 pgs.
"International Application Serial No. PCT/US2013/034286, International Preliminary Report on Patentability mailed Oct. 9, 2014", 8 pgs.
"International Application Serial No. PCT/US2013/034286, International Search Report mailed Jun. 25, 2013", 6 pgs.
"International Application Serial No. PCT/US2013/034286, Written Opinion mailed Jun. 25, 2013", 6 pgs.
"International Application Serial No. PCT/US2013/034293, International Preliminary Report on Patentability mailed Oct. 9, 2014", 9 pgs.
"International Application Serial No. PCT/US2013/034293, International Search Report mailed Jun. 25, 2013", 6 pgs.
"International Application Serial No. PCT/US2013/034293, Written Opinion mailed Jun. 25, 2013", 7 pgs.
"International Application Serial No. PCT/US2016/052163, International Preliminary Report on Patentability Mailed Apr. 5, 2018", 10 pgs.
"International Application Serial No. PCT/US2016/052163, International Search Report mailed Jan. 20, 2017", 7 pgs.
"International Application Serial No. PCT/US2016/052163, Invitation to Pay Add'l Fees and Partial Search Report mailed Nov. 7, 2016", 7 pgs.
"International Application Serial No. PCT/US2016/052163, Written Opinion mailed Jan. 20, 2017", 8 pgs.
"International Application Serial No. PCT/US2018/021571, International Preliminary Report on Patentability mailed Sep. 19, 2019", 8 pgs.
"International Application Serial No. PCT/US2018/021571, International Search Report mailed Jun. 7, 2018", 6 pgs.
"International Application Serial No. PCT/US2018/021571, Written Opinion mailed Jun. 7, 2018", 6 pgs.
"International Application Serial No. PCT/US2018/031177, International Preliminary Report on Patentability mailed Nov. 21, 2019", 8 pgs.
"International Application Serial No. PCT/US2018/031177, International Search Report mailed Jul. 31, 2018", 6 pgs.
"International Application Serial No. PCT/US2018/031177, Written Opinion mailed Jul. 31, 2018", 6 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995, 1997,1998), 36 pgs.
"Japanese Application Serial No. 2015-162707, Office Action mailed Jun. 28, 2016", (W/ English Translation), 8 pgs.
"Japanese Application Serial No. 2013-521854, Notice of Reason for Rejection mailed Sep. 16, 2014", (W/ English Translation), 6 pgs.
"Japanese Application Serial No. 2013-521854, Response filed Dec. 16, 2014 to Notice of Reason for Rejection mailed Sep. 16, 2014", W/ English Claims, 11 pgs.
"Japanese Application Serial No. 2013-521855, Amendment filed Jul. 22, 2014", (W/ English Translation), 20 pgs.

(56) References Cited

OTHER PUBLICATIONS

"Japanese Application Serial No. 2013-521855, Office Action mailed Mar. 24, 2015", W/ English Translation, 8 pgs.

"Japanese Application Serial No. 2013-521856, Notice of Allowance mailed Jan. 5, 2016", w/English Translation, 6 pgs.

"Japanese Application Serial No. 2013-521856, Office Action mailed Sep. 1, 2015", (W/ English Translation), 5 pgs.

"Japanese Application Serial No. 2013-521856, Response filed Dec. 1, 2015 to Office Action mailed Sep. 1, 2015", w/English Translation, 9 pgs.

"Japanese Application Serial No. 2013-521857, Notice of Allowance mailed Feb. 9, 2016", w/English Translation, 6 pgs.

"Japanese Application Serial No. 2013-521857, Notice of Reasons for Rejection mailed Aug. 18, 2015", (W/ English Translation), 6 pgs.

"Japanese Application Serial No. 2013-521857, Preliminary Amendment filed May 18, 2014", (W/ English translation of claims), 9 pgs.

"Japanese Application Serial No. 2013-521857, Response filed Jan. 25, 2016 to Notice of Reasons for Rejection mailed Aug. 18, 2015", (W/ English Translation), 17 pgs.

"Japanese Application Serial No. 2013-544655, Office Action mailed Mar. 8, 2016", (W/ English Translation), 8 pgs.

"Japanese Application Serial No. 2013-544655, Office Action mailed Sep. 29, 2015", (W/ English Translation), 7 pgs.

"Japanese Application Serial No. 2013-544655, Response filed Jan. 4, 2016 to Office Action mailed Sep. 29, 2015", (English Translation of Claims), 14 pgs.

"Japanese Application Serial No. 2013-544655, Response filed Jul. 14, 2016 to Office Action mailed Mar. 8, 2016", (w/ English Translation of Claims), 13 pgs.

"Japanese Application Serial No. 2013-544858, Request for Examination filed Feb. 4, 2014", (With English Translation), 14 pgs.

"Japanese Application Serial No. 2014-121515, Notice of Reasons for Rejection mailed Jan. 5, 2016", (W/ English Translation), 9 pgs.

"Japanese Application Serial No. 2014-121515, Office Action mailed Jun. 2, 2015", (W/ English Translation), 10 pgs.

"Japanese Application Serial No. 2014-121515, Response filed May 11, 2016 to Notice of Reasons for Rejection mailed Jan. 5, 2016", (W/ English Translation Of Claims), 11 pgs.

"Japanese Application Serial No. 2014-121515, Response filed Aug. 20, 2015 to Office Action mailed Jun. 2, 2015", (W/ English Translation Of Claims), 6 pgs.

"Japanese Application Serial No. 2014-542297, Office Action mailed May 31, 2016", (W/ English Translation Of Claims), 6 pgs.

"Japanese Application Serial No. 2014-542297, Office Action mailed Jun. 30, 2015", (W/ English Translation), 10 pgs.

"Japanese Application Serial No. 2014-542297, Office Action mailed Nov. 24, 2015", (W/ English Translation), 10 pgs.

"Japanese Application Serial No. 2014-542297, Response filed Feb. 23, 2016 to Office Action mailed Nov. 24, 2015", (W/ English Translation Of Claims), 15 pgs.

"Japanese Application Serial No. 2014-542297, Response filed Jun. 8, 2016 to Office Action mailed May 31, 2016", (W/ English Translation Of Claims), 14 pgs.

"Japanese Application Serial No. 2014-542297, Response filed Sep. 28, 2015 to Office Action mailed Jun. 30, 2015", (W/ English Translation Of Claims), 16 pgs.

"Japanese Application Serial No. 2014-542301, Office Action mailed May 12, 2015", (W/ English Translation), 6 pgs.

"Japanese Application Serial No. 2014-542301, Response filed Aug. 10, 2015 to Office Action mailed May 12, 2015", (W/ English translation of claims), 21 pgs.

"Japanese Application Serial No. 2014-554709, Office Action mailed Jul. 5, 2016", (W/ English Translation), 6 pgs.

"Japanese Application Serial No. 2014-554709, Preliminary Amendment filed Jul. 29, 2015", (W/ English translation of claims), 8 pgs.

"Japanese Application Serial No. 2014-554709, Response filed Dec. 19, 2016 to Office Action mailed Jul. 5, 2016", (W/ English Translation of Claims), 11 pgs.

"Japanese Application Serial No. 2015-162707, Office Action mailed Nov. 29, 2016", (W/ English Translation), 3 pgs.

"Japanese Application Serial No. 2015-162707, Response filed Jan. 26, 2017 to Office Action mailed Nov. 27, 2016", (W/ English Translation), 16 pgs.

"Japanese Application Serial No. 2015-199496, Office Action mailed Sep. 6, 2016", (W/ English Translation), 5 pgs.

"Japanese Application Serial No. 2015-199496, Response filed Dec. 5, 2016 to Office Action mailed Sep. 6, 2016", (W/ English Translation of Claims), 9 pgs.

"Japanese Application Serial No. 2015-503563, Office Action mailed Dec. 20, 2016", (W/ English Translation), 10 pgs.

"Japanese Application Serial No. 2015-503563, Response Filed Mar. 13, 2017 to Office Action Mailed Dec. 20, 2016", (W/ English Translation), 9 pgs.

"Japanese Application Serial No. 2016-145390, Office Action mailed Apr. 25, 2017", (W/ English Translation), 5 pgs.

"Japanese Application Serial No. 2016-145390, Response filed Jul. 3, 2017 to Office Action mailed Apr. 25, 2017", (W/ English Translation of Claims), 16 pgs.

"Japanese Application Serial No. 2017-161246, Office Action mailed May 15, 2018", (W/ English Translation), 6 pgs.

"Japanese Application Serial No. 2019-562605, Notification of Reasons for Refusal mailed Jun. 16, 2020", (W/ English Translation), 7 pgs.

"Japanese Application Serial No. 2019-562605, Notification of Reasons for Refusal mailed Nov. 10, 2020", (W/ English Translation), 5 pgs.

"Japanese Application Serial No. 2019-562605, Response filed Feb. 9, 2021 to Notification of Reasons for Refusal mailed Nov. 10, 2020", (W/ English Claims), 19 pgs.

"Japanese Application Serial No. 2019-562605, Response filed Sep. 15, 2020 to Notification of Reasons for Refusal mailed Jun. 16, 2020", (W/ English Claims), 15 pgs.

"Journey II XR, Bi-Cruciate Retaining Knee System", Smith & Nephew, Surgical Technique, (2015), 40 pgs.

"Legacy Implant Options", Nexgen Complete Knee Solution, (2002), 8 pgs.

"LPS-Flex Fixed Bearing Knee: Surgical Technique", Zimmer, Inc., (2004, 2007, 2008), 16 pgs.

"Mexican Application Serial No. 2016/001734, Response filed Aug. 31, 2021 to Office Action mailed Jun. 7, 2021", (W/ English Translation of Claims), 29 pgs.

"Mexican Application Serial No. MX/a/2013/000988, Office Action mailed Mar. 18, 2015", w/English Claims, 17 pgs.

"Mexican Application Serial No. MX/a/2013/000988, Response filed Jun. 1, 2015 to Office Action mailed Mar. 18, 2015", (W/ English Translation), 12 pgs.

"Mexican Application Serial No. MX/A/2013/000988. Office Action Mailed Jun. 5, 2015", w/ summary in English, 6 pgs.

"Mexican Application Serial No. MX/A/2013/000990, Final Office Action mailed Feb. 4, 2016", w/ summary in English, 4 pgs.

"Mexican Application Serial No. MX/A/2013/000990, Office Action mailed Feb. 19, 2015", (W/ English Translation), 4 pgs.

"Mexican Application Serial No. MX/A/2013/000990, Response filed Apr. 29, 2015 to Office Action mailed Feb. 19, 2015", W/ English Claims, 18 pgs.

"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.

"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.

"Natural-Knee II Primary System Surgical Technique", Zimmer, Inc., (2005), 48 pgs.

"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.

"Nexgen Complete Knee Solution", Extramedullary/Intramedullary Tibial Resector: Surgical Technique, Zimmer, Inc. 97-5997-02 Rev 1, (2000), 26 pgs.

(56)				References Cited

OTHER PUBLICATIONS

"Nexgen Complete Knee Solution for the Legacy Knee LPS-Flex Fixed Bearing Knee", Zimmer Surgical Technique, 97-5964-102-00, (2004, 2007), 12 pgs.

"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.

"NexGen Implant Options Surgeon-Specific", Zimmer Inc., (2000), 16 pgs.

"NexGen LPS Fixed Knee: Surgical Technique", Zimmer Inc., (2002, 2008), 44 pgs.

"NexGen LPS-Flex Mobile and LPS-Mobile Bearing Knees", Zimmer, Inc., (2007, 2008), 4 pgs.

"NexGen Trabecular Metal Modular Plates", Zimmer Inc., (2007), 19 pgs.

"Persona "Medial Congruent Articular Surface" System Overview", Zimmer, Inc., (2015), 6 pgs.

"Persona "The Personalized Knee System"", Medial Congruent Sales Training, Zimmer, Inc., (Jul. 2015), 53 pgs.

"Persona "The Personalized Knee System" Medial Congruent Advanced Bearings", Zimmer, Inc., (2015), 2 pgs.

"Persona "The Personalized Knee System" Medial Congruent Articular Surface Design Rationale", Zimmer, Inc., (2015), 20 pgs.

"Persona "The Personalized Knee System" Persona Medial Congruent", Mar. 24-28, 2015 at the American Academy of Orthopaedic Surgeons (AAOS) Annual Meeting., (Mar. 2015), 1 pg.

"Persona "The Personalized Knee System" Surgical Technique", Zimmer, Inc., (2015), 72 pgs.

"Persona Medial Congruent Articular Surface", Sales Training, Zimmer Biomet, (Jan. 2016), 71 pgs.

"PFC Sigma Knee System with Rotating Platform Technical/ Monograph", Depuy PFC Sigma RP, 0611-29-050 (Rev. 3), (1999), 70 pgs.

"Primary/Revision Surgical Technique for NexGen Rotating Hinge Knee (RHK)", Zimmer, Inc. Nexgen Complete Knee Solution, 97-5880-02, (2002), 116 pgs.

"Revision Instrumentation Surgical Technique for Legacy Knee Constrained Condylar Knee", Zimmer, Inc. Nexgen Complete Knee Solution, 97-5994-202, (2001), 61 pgs.

"Russian Application Serial No. 2013106942, Office Action mailed Apr. 16, 2015", W/ English Translation, 5 pgs.

"Russian Application Serial No. 2013106942, Response filed Jul. 15, 2015 Office Action mailed Apr. 16, 2015", (W/ English translation of claims), 146 pgs.

"Russian Application Serial No. 2013106943, Office Action mailed Jul. 1, 2015", (W/ English Translation), 6 pgs.

"Russian Application Serial No. 2013106943, Office Action mailed Dec. 28, 2015", w/ partial English Translation, 6 pgs.

"Russian Application Serial No. 2013106943, Response filed Apr. 28, 2016 to Office Action mailed Dec. 28, 2015", (W/ English translation of claims), 19 pgs.

"Russian Application Serial No. 2013106943, Response filed Oct. 30, 2015 to Office Action mailed Jul. 1, 2015", (W/ English translation of claims), 21 pgs.

"South African Application Serial No. 2013/01327, Amendment filed Apr. 24, 2014", W/ English Translation, 4 pgs.

"South African Application Serial No. 2013/01328, Amendment filed Apr. 24, 2014", W/ English Translation, 4 pgs.

"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.

"Surgical Technique for the CR-Flex Fixed Bearing Knee", NexGen Complete Knee Solution, Zimmer, Inc., (2003), 22 pgs.

"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.

"Surgical Technique for the Legacy Posterior Stabilized Knees", Zimmer, Inc. Nexgen Complete Knee Solution, 97-5996-02, (2002), 43 pgs.

"Surgical Technique—Nexgen Complete Knee Solution for the Legacy Knee LPS-Flex Fixed Bearing Knee", Zimmer, Inc., (2004, 2007), 12 pgs.

"The Zimmer Institute Surgical Technique MIS Quad-Sparing Surgical Technique for Total Knee Arthroplasty", NExGen Complete Knee Solution, (2004), 55 pgs.

"Tibial Baseplate: Pocket Guide (United States Version)", Zimmer, Inc.,, (2009), 17 pgs.

"Trabecular Metal Monoblock Tibial Components", Zimmer, Inc., (2007), 4 pgs.

"Trabecular Metal Monoblock Tibial Components Surgical Technique Addendum", Nexgen Zimmer, Inc., (2005, 2007), 12 pgs.

"Trabecular Metal Tibial Tray: Surgical Technique", NexGen Zimmer, Inc., (2007, 2009), 16 pgs.

"Turkish Application Serial No. 11808493.8, Working Requirements mailed Feb. 17, 2020", 3 pgs.

"Turkish Application Serial No. 12718882.9, Working Requirements mailed Feb. 13, 2020", 3 pgs.

"Vanguard® ID Total Knee, Surgical Technique", Zimmer Biomet; 0682.1-GLBL-en-REV0317, (2017), 36 pgs.

"Zimmer MIS Intramedullary Instrumentation Surgical Technique For NexGen Cruciate Retaining & NexGen Legacy Posterior Stabilized Knees", printed 2005, 2009, Zimmer, Inc., (2009), 45 pgs.

"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.

"Zimmer NexGen CR-Flex and LPS-Flex Knees Surgical Technique with posterior Referencing Instrumentation.", Zimmer Inc., (2010, 2011), 48 pgs.

"Zimmer NexGen LCCK Surgical Technique for use with LCCK 4-in-1 Instrumentation", Zimmer, Inc.; copyright 2009, 2010, 2011, (May 2011), 52 pgs.

"Zimmer NexGen MIS Modular Tibial Plate and Keel Cemented Surgical Technique", Zimmer Inc., (2006, 2011), 26 pgs.

"Zimmer NexGen MIS Tibial Component", Brochure-97-5950-001-00 7.5mm, (2005, 2006), 8 pgs.

"Zimmer NexGen MIS Tibial Component Cemented Surgical Technique", Zimmer, Inc, #97-5950-002-00 Rev.1 1.5ML, (2005), 14 pgs.

"Zimmer NexGen MIS Tibial Component Cemented Surgical Technique", Zimmer Inc., (2005, 2006, 2008, 2009, 2010), 16 pgs.

"Zimmer NexGen Trabecular Metal Augments—Abbreviated Surgical Technique", Zimmer, Inc., (2004, 2006), 6 pgs.

"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.

"Zimmer NexGen Trabecular Metal Primary Patella Surgical Technique", Zimmer. Inc., 97-7255-112-00, (2005), 10 pgs.

"Zimmer NexGen Trabecular Metal Tibial Tray", Surgical Technique, Zimmer, Inc., (2007, 2009), 16 pgs.

"Zimmer Patient Specific Instruments", Surgical Techniques for NexGen Complete Knee Solution Zimmer, Inc., (2010), 16 pgs.

Annayappa, Ramesh, "Tibial Prosthesis", U.S. Appl. No. 13/189,328, filed Jul. 22, 2011, 82 pgs.

Annayappa, Ramesh, et al., "Tibial Prosthesis", U.S. Appl. No. 13/189,324, filed Jul. 22, 2011, 50 pgs.

Bellemans, Johan, et al., "Is Neutral Mechanical Alignment Normal for All Patients?", Clinical Orthopaedics and Related Research; DOI 10.1007/s11999-011-1936-5, (Jun. 9, 2011), 9 pgs.

Ding, M., et al., "Age-related variations in the microstructure of human tibial cancellous bone", Journal of Orthopaedic Research, 20(3), (2002), 615-621.

Ding, M., et al., "Changes in the three-dimensional microstructure of human tibial cancellous bone in early osteoarthritis", Journal of Bone & Joint Surgery (British), 85-B(6), (Aug. 2003), 906-912.

Doyle, et al., "Comparative Analysis of Human Trabecular Bone and Polyurethane Foam", Purdue University., (Accessed online Jul. 24, 2013), 1 pg.

Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.

(56) References Cited

OTHER PUBLICATIONS

Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.

Freeman, M.A.R., et al., "The Movement of the Knee Studied by Magnetic Resonance Imaging", Advanced Bearings—Clinical Orthopedics & Related Research 2003, (2003), 1 pg.

Hofmann, Aaron A, et al., "Posterior Stabilization in Total Knee Arthroplasty with Use of an Ultracongruent Polyethylene", The Journal of Arthroplasty vol. 15, No. 5, (2000), 576-583.

Hutt, Jonathan, et al., "Functional joint line obliquity after kinematic total knee arthroplasty", International Orthopaedics; DOI 10.1007/s00264-015-2733-7, (Mar. 21, 2015), 6 pgs.

Hvid, Ivan, et al., "Trabecular bone Strength Patterns at the Proximal Tibial Epiphysis", Journal of Orthopaedic Research, vol. 3, No. 4, (1985), 464-472.

Klostermann, et al., "Distribution of bone mineral density with age and gender in the proximal tibia", Clinical Biomechanics 19, (2004), pp. 370-376.

Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.

Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.

Parisi, Raymond C, "Motion Facilitating Tibial Components for a Knee Prosthesis", U.S. Appl. No. 13/229,103, filed Sep. 9, 2011, 46 pgs.

Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.

Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.

Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.

Stilling, et al., "Superior fixation of pegged trabecular metal over screw-fixed pegged porous titanium fiber mesh", Acta Orthopaedica., (2011), 177-186.

Victor, Jan M. K., et al., "Constitutional Varus Does Not Affect Joint Line Orientation in the Coronal Plane", Joint Line Orientation in the Coronal Plane; 472; DOI 10.1007/s11999-013-2898-6, (Jun. 4, 2013), pp. 98-104.

Wentorf, Mary S. S, "Asymmetric Tibial Components for a Knee Prosthesis", U.S. Appl. No. 13/189,338, filed Jul. 22, 2011, 58 pgs.

Wentorf, Mary S. S, "Asymmetric Tibial Components for a Knee Prosthesis", U.S. Appl. No. 13/189,339, filed Jul. 22, 2011, 52 pgs.

Wentorf, Mary S. S, "Asymmetric Tibial Components for a Knee Prosthesis", U.S. Appl. No. 13/189,336, filed Jul. 22, 2011, 60 pgs.

U.S. Appl. No. 17/866,151, filed Jul. 15, 2022, Implants for Adding Joint Inclination to a Knee Arthroplasy.

"U.S. Appl. No. 16/179,201, Supplemental Notice of Allowability mailed Aug. 2, 2022", 2 pgs.

"U.S. Appl. No. 16/530,423, Notice of Allowance mailed Jun. 14, 2022", 6 pgs.

"U.S. Appl. No. 16/530,423, Response filed Jun. 1, 2022 to Non Final Office Action mailed Mar. 3, 2022", 14 pgs.

"U.S. Appl. No. 16/849,394, Examiner Interview Summary mailed Aug. 29, 2022", 2 pgs.

"U.S. Appl. No. 16/849,394, Non Final Office Action mailed Jun. 3, 2022", 9 pgs.

"U.S. Appl. No. 16/849,394, Notice of Allowance mailed Sep. 15, 2022", 8 pgs.

"U.S. Appl. No. 16/849,394, Response filed Aug. 24, 2022 to Non Final Office Action mailed Jun. 3, 2022", 15 pgs.

"U.S. Appl. No. 17/866,151, Preliminary Amendment filed Aug. 3, 2022", 6 pgs.

"European Application Serial No. 21177256.1, Extended European Search Report mailed May 17, 2022" 9 pgs.

"Japanese Application Serial No. 2021-097369, Notification of Reasons for Rejection mailed Jun. 14, 2022", w/ English Translation, 11 pgs.

"Japanese Application Serial No. 2021-097369, Response filed Sep. 12, 2022 to Notification of Reasons for Rejection mailed Jun. 14, 2022", w English claims, 17 pgs.

"European Application Serial No. 18726670.5, Communication Pursuant to Article 94(3) EPC mailed Dec. 15, 2022", 5 pgs.

"U.S. Appl. No. 18/081,481, Preliminary Amendment filed Jan. 11, 2023", 6 pgs.

"European Application Serial No. 21178298.2, Response filed Dec. 21, 2022 to Extended European Search Report mailed Mar. 1, 2022", 23 pgs.

"European Application Serial No. 21177256.1, Response filed Dec. 21, 2022 to Extended European Search Report mailed May 17, 2022", 35 pgs.

"European Application Serial No. 18726670.5, Response filed Apr. 25, 2023 to Communication Pursuant to Article 94(3) EPC mailed Dec. 15, 2022", 35 pgs.

"European Application Serial No. 21177256.1, Communication Pursuant to Article 94(3) EPC mailed Jun. 7, 2023", 4 pgs.

"U.S. Appl. No. 17/068,435, Non Final Office Action mailed Jun. 15, 2023", 13 pgs.

"U.S. Appl. No. 18/228,322, Preliminary Amendment filed Aug. 16, 2023", 6 pgs.

"U.S. Appl. No. 17/068,435, Response filed Sep. 12, 2023 to Non Final Office Action mailed Jun. 15, 2023", 11 pgs.

"U.S. Appl. No. 17/545,728, Non Final Office Action mailed Sep. 22, 2023", 16 pgs.

"U.S. Appl. No. 17/068,435, Notice of Allowance mailed Oct. 17, 2023", 5 pgs.

"European Application Serial No. 21177256.1, Response filed Oct. 17, 2023 to Communication Pursuant to Article 94(3) EPC mailed Jun. 7, 2023", 10 pgs.

"European Application Serial No. 21178298.2, Communication Pursuant to Article 94(3) EPC mailed Nov. 29, 2023", 5 pgs.

"U.S. Appl. No. 17/545,728, Response filed Dec. 12, 2023 to Non Final Office Action mailed Sep. 22, 2023", 16 pgs.

"Chinese Application Serial No. 202110590378.1, Office Action mailed Dec. 26, 2023", w English Translation, 15 pgs.

"U.S. Appl. No. 17/545,728, Final Office Action mailed Feb. 20, 2024", 17 pgs.

U.S. Appl. No. 18/081,481, filed Dec. 14, 2022, Tibial Prosthesis With Tibial Bearing Component Securing Feature.

U.S. Appl. No. 18/228,322, filed Jul. 31, 2023, Posterior Stabalized Prosthesis System.

"U.S. Appl. No. 17/134,885, PTO Response to Rule 312 Communication mailed Jul. 15, 2025", 2 pgs.

"U.S. Appl. No. 17/866,151, Non Final Office Action mailed Jul. 14, 2025", 14 pgs.

"U.S. Appl. No. 18/081,481, Notice of Allowance mailed Jul. 15, 2025", 7 pgs.

"European Application Serial No. 24215248.6, Response Filed Aug. 27, 2025 to Extended European Search Report mailed Mar. 18, 2025", 8 pgs.

"European Application Serial No. 25163024.0, Extended European Search Report mailed Jun. 25, 2025", 4 pgs.

"European Application Serial No. 25177136.6, Extended European Search Report mailed Sep. 3, 2025", 9 pgs.

"European Application Serial No. 21178298.2, Response filed Feb. 29, 2024 to Communication Pursuant to Article 94(3) EPC mailed Nov. 29, 2023", 21 pgs.

"Chinese Application Serial No. 202110590378.1, Response Filed Mar. 18, 2024 to Office Action mailed Dec. 26, 2023", W English Claims, 19 pgs.

"U.S. Appl. No. 17/545,728, Appeal Brief filed Sep. 9, 2024", 25 pgs.

(56)                 References Cited

OTHER PUBLICATIONS

"U.S. Appl. No. 18/081,481, Non Final Office Action mailed Oct. 9, 2024", 9 pgs.

"U.S. Appl. No. 17/545,728, Notice of Allowance mailed Nov. 8, 2024", 17 pgs.

"U.S. Appl. No. 17/134,885, Non Final Office Action mailed Nov. 21, 2024", 9 pgs.

"U.S. Appl. No. 18/081,481, Response filed Jan. 7, 2025 to Non Final Office Action mailed Oct. 9, 2024", 14 pgs.

"U.S. Appl. No. 19/038,621, Preliminary Amendment filed Jan. 28, 2025".

"U.S. Appl. No. 17/134,885, Response filed Feb. 12, 2025 to Non Final Office Action mailed Nov. 21, 2024", 12 pgs.

"U.S. Appl. No. 17/134,885, Notice of Allowance mailed Feb. 25, 2025", 5 pgs.

"European Application Serial No. 24215248.6, Extended European Search Report mailed Mar. 18, 2025", 4 pgs.

"U.S. Appl. No. 18/081,481, Final Office Action mailed Apr. 8, 2025", 6 pgs.

"U.S. Appl. No. 18/081,481, Response filed Jun. 2, 2025 to Final Office Action mailed Apr. 8, 2025", 14 pgs.

"European Application Serial No. 25162292.4, Extended European Search Report mailed May 20, 2025", 7 pgs.

"U.S. Appl. No. 17/866,151, Response filed Oct. 10, 2025 to Non Final Office Action mailed Jul. 14, 2025", 14 pgs.

"International Application Serial No. PCT US2011 045080, International Search Report mailed Feb. 29, 2012", 3 pgs.

"International Application Serial No. PCT US2011 045080, Written Opinion mailed Feb. 29, 2012", 5 pgs.

"International Application Serial No. PCT US2011 045080, International Preliminary Report on Patentability mailed Apr. 11, 2013", 7 pgs.

\* cited by examiner

| CCK | | PERSONA CCK FEMORAL SIZE | | | | | | | | | | | | |
|---|---|---|---|---|---|---|---|---|---|---|---|---|---|---|
| | | 1 | 1+ | 3 | 3+ | 5 | 5+ | 7 | 7+ | 9 | 9+ | 11 | 11+ | 13 |
| | A | 1-1+/AB | | 3-5+/AB | | | | | | | | | | |
| | B | | | | | | | | | | | | | |
| | C | 1-1+/CD | | 3-5+/CD | | | | 7-9+/CD | | | | | | |
| | D | | | | | | | | | | | | | |
| | E | | | 3-5+/EF | | | | 7-9+/EF | | | | 11-11+/EF | | |
| | F | | | | | | | | | | | | | |
| | G | | | | | | | | 7-9+/GH | | | 11-13+/GH | | |
| | H | | | | | | | | | | | | | |
| | J | | | | | | | | | | | 11-13/J | | |

302, 304

350 → PERSONA TIBIAL SIZE

352

FEMORAL PROSTHESES WITH UPSIZING AND DOWNSIZING CAPABILITIES

CLAIM OF PRIORITY

This application is a continuation of U.S. patent application Ser. No. 16/675,938, filed Nov. 6, 2019, which is a continuation of U.S. patent application Ser. No. 15/971,743, filed on May 4, 2018, now issued as U.S. Pat. No. 10,500, 054, which claims the benefit of U.S. Provisional Patent Application Ser. No. 62/505,322, filed on May 12, 2017, the benefit of priority of each of which is claimed hereby, and each of which is incorporated by reference herein in its entirety.

FIELD

The present subject matter relates to orthopedic prostheses and, more particularly, to prostheses and systems used in knee arthroplasties including revision knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral prosthesis implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

Overview

This disclosure pertains generally to femoral prostheses and systems for a knee arthroplasty including a revision knee arthroplasty. The present inventors have recognized, among other things, that it is desirable to offer versatile sizing options with regards to a combination of femoral posterior condylar offset and femoral medial-lateral condylar extent. More particularly, the present inventors have recognized a femoral prosthesis system that can have a plurality of sizing options using two families of femoral prostheses. The second family of femoral prostheses has a predetermined increase in the femoral posterior condylar offset relative to the first family of femoral prosthesis. In one example, the second family of femoral prostheses can have the predetermined increase in the femoral posterior condylar offset while maintaining substantially the same femoral medial-lateral condylar extent relative to the first family of femoral prostheses. Thus, for example, if sizing criteria dictate, a femoral prosthesis of a first size from the second family can be selected having a relatively larger femoral posterior condylar offset but a same femoral medial-lateral condylar extent to a correspondingly sized femoral prosthesis from the first family. Similarly, the systems allow for downsizing should sizing criteria dictate. For example, a femoral prosthesis of a first size from the first family can be selected having a femoral medial-lateral condylar extent that is larger than desired but having a femoral posterior condylar offset that is sized as desired. In such situation, the disclosed examples allow a correspondingly sized femoral prosthesis from the second family to be selected that has substantially a same femoral posterior condylar offset but a femoral medial-lateral condylar extent that differs from that of the femoral prosthesis of the first size from the first family by a predetermined amount. Such sizing versatility allows a patient appropriate femoral prosthesis from the first family or the second family to be selected more easily (e.g., selection is made using a consistent logical upsizing or downsizing scheme).

Regarding the first family of femoral prostheses, according to one example, the first family of femoral prostheses have a first range of posterior condylar offsets and a corresponding range of femoral medial-lateral condylar extents. The range for the femoral medial-lateral condylar extent of the first family can be between about 59 mm (for a size 1 femoral prosthesis) and about 80 mm (for a size 13 femoral prosthesis), for example. Similarly, the range of the posterior condylar offset can be between about 33 mm (for the size 1 femoral prosthesis) to about 52 mm (for the size 13 femoral prosthesis), for example. According to some examples, the femoral medial-lateral condylar extent can be substantially linearly incremented in a size increase from the size 1 to the size 13 femoral prosthesis such that for each increase in femoral size (e.g., going from a size 1 to size 3 or from a size 7 to a size 9) there is a corresponding known increase in the femoral medial-lateral condylar extent. The posterior condylar offset can be similarly substantially linearly incremented such that there is a known increase when moving up or down in prostheses size.

The present inventors have additionally recognized the prosthesis system can have the second family of femoral prostheses be compatible with the same tibial bearing component as a correspondingly sized femoral prosthesis from the first family of femoral prostheses. According to some examples, the second family of femoral prostheses can have a second range of posterior condylar offsets and corresponding femoral medial-lateral condylar extents. The range for the femoral medial-lateral condylar extent of the first family can be between about 59 mm (for a size 1+ femoral prosthesis) and about 77 mm (for a size 11+ femoral prosthesis), for example. Similarly, the range of the posterior condylar offset can be between about 37 mm (for the size 1+ femoral prosthesis) to about 52 mm (for the size 11+ femoral prosthesis), for example. According to some examples, the femoral medial-lateral condylar extent can be substantially linearly incremented in a size increase from the size 1+ to the size 11+ femoral prosthesis such that for each increase in femoral size there is a corresponding increase in the femoral medial-lateral condylar extent. The posterior condylar offset can be similarly substantially linearly incremented such that there is a known increase when moving up or down in prostheses size.

As discussed above, the size increase for the first family of femoral prostheses and the size increase for the second family of femoral prostheses can be related so as to be substantially the same (See FIGS. 5A-5C) according to some examples. However, the posterior condylar offset between the first family and the second family can be offset in that the femoral prostheses from the second family are always larger by a known amount (e.g., 3 mm) in the posterior condylar offset.

To further illustrate the apparatuses and systems disclosed herein, the following non-limiting examples are provided:

Example 1 is a system for knee arthroplasty that can optionally include: a first family having a first plurality of femoral prostheses with different stock sizes from one another, each of the first plurality of femoral prostheses having: a first stem housing extending along a first axis; and a first medial condyle and a first lateral condyle coupled to the first stem housing; wherein the first medial condyle and the first lateral condyle have a first posterior condylar offset as measured from the first axis to a first posterior-most point of the first medial condyle and the first lateral condyle; and wherein the first medial condyle and the first lateral condyle have a first femoral medial-lateral condylar extent from a medial most edge of the first medial condyle to a lateral most edge of the first lateral condyle; a second family having a second plurality of femoral prostheses with different stock sizes from one another, each of the second plurality of femoral prostheses having: a second stem housing extending along a second axis; and a second medial condyle and a second lateral condyle coupled to the second stem housing; wherein the second medial condyle and the second lateral condyle have a second posterior condylar offset from the second axis to a second posterior-most point of the second medial condyle and the second lateral condyle; and wherein the second medial condyle and the second lateral condyle have a second femoral medial-lateral condylar extent from a medial most edge of the second medial condyle to a lateral most edge of the second lateral condyle; wherein the first femoral medial-lateral condylar extent of at least one of the first plurality of femoral prostheses and the second femoral medial-lateral condylar extent of at least one of the second plurality of femoral prostheses are substantially the same.

In Example 2, the subject matter of Example 1 optionally can include the at least one of the first plurality of femoral prostheses and the at least one of the second plurality of femoral prostheses are configured to articulate with a same tibial bearing component.

In Example 3, the subject matter of any one or more of Examples 1-2 optionally can include the first posterior condylar offset of the at least one of the first plurality of femoral prostheses and the second posterior condylar offset of the at least one of the second plurality of femoral prostheses differ by a predetermined amount.

In Example 4, the subject matter of any one or more of Examples 1-3 optionally can include the predetermined amount comprises substantially 3 mm, and wherein the second medial condyle and a second lateral condyle are thickened along a posterior portion comprising at least a region between a posterior bone-contacting surface and a posterior portion of the J-curve when viewed in a sagittal plane relative to a corresponding thickness of the first medial condyle and the first lateral condyle.

In Example 5, the subject matter of any one or more of Examples 1-4 optionally can include the first posterior condylar offset of at least four of the first plurality of the femoral prostheses is substantially the same as the second posterior condylar offset of at least four of the second plurality of femoral prostheses.

In Example 6, the subject matter of any one or more of Examples 1-5 optionally include the first posterior condylar offset of at least six of the first plurality of the femoral prostheses is substantially the same as the second posterior condylar offset of at least six of the second plurality of femoral prostheses.

In Example 7, the subject matter of any one or more of Examples 1-6 optionally can include the first femoral medial-lateral condylar extent of at least four of the first plurality of the femoral prostheses is substantially the same as the second femoral medial-lateral condylar extent of at least four of the second plurality of femoral prostheses.

In Example 8, the subject matter of any one or more of Examples 1-7 optionally can include the first femoral medial-lateral condylar extent of at least six of the first plurality of the femoral prostheses is substantially the same as the second femoral medial-lateral condylar extent of at least six of the second plurality of femoral prostheses.

In Example 9, the subject matter of any one or more of Examples 1-8 optionally can include each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

In Example 10, the subject matter of any one or more of Examples 1-9 optionally can include each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

Example 11 is a system for knee arthroplasty can optionally include: a first family having a first plurality of femoral prostheses with different stock sizes from one another, each of the first plurality of femoral prostheses having: a first stem housing extending along a first axis; and a first medial condyle and a first lateral condyle coupled to the first stem housing; wherein the first medial condyle and the first lateral condyle have a first posterior condylar offset as measured from the first axis to a first posterior-most point of the first medial condyle and the first lateral condyle; and wherein the first medial condyle and the first lateral condyle have a first femoral medial-lateral condylar extent as measured from a medial most edge of the first medial condyle to a lateral most edge of the first lateral condyle; a second family having a second plurality of femoral prostheses with different stock sizes from one another, each of the second plurality of femoral prostheses having: a second stem housing extending along a second axis; and a second medial condyle and a second lateral condyle coupled to the second stem housing; wherein the second medial condyle and the second lateral condyle have a second posterior condylar offset as measured from the second axis to a second posterior-most point of the second medial condyle and the second lateral condyle; and wherein the second medial condyle and the second lateral condyle have a second femoral medial-lateral condylar extent as measured from a medial most edge of the second medial condyle to a lateral most edge of the second lateral condyle; wherein the first posterior condylar offset of at least one of the first plurality of femoral prostheses and the second posterior condylar offset of at least one of the second plurality of femoral prostheses are substantially the same; and wherein the first femoral medial-lateral condylar extent of the at least one of the first plurality of femoral prostheses and the second femoral medial-lateral condylar extent of the at least one of the second plurality of femoral prostheses differ by a first predetermined amount.

In Example 12, the subject matter of Example 11 optionally can include at least one of the first medial condyle and the first lateral condyle have a first thickness at a posterior portion between a first posterior bone-contacting surface and the first posterior-most point and at least one of the second medial condyle and the second lateral condyle have a second thickness at a corresponding posterior portion between a second posterior bone-contacting surface and the second posterior-most point, and wherein the first thickness differs from the second thickness by a second predetermined amount.

In Example 13, the subject matter of Example 12 optionally can include a third thickness of the at least one of the first medial condyle and the first lateral condyle as measured between a first posterior chamfer and an articular surface differs by a third predetermined amount from a fourth thickness of at least one of the second medial condyle and the second lateral condyle as measured between a corresponding second posterior chamfer and a corresponding articular surface.

In Example 14, the subject matter of Example 13 optionally can include an anterior bone-contacting surface of the at least one of the second plurality of femoral prostheses is disposed relatively nearer the second axis by a fourth predetermined amount than a corresponding anterior bone-contacting surface of the at least one of the first plurality of femoral prostheses.

In Example 15, the subject matter of Example 14 optionally can include one or both of the first predetermined amount and the second predetermined amount comprises substantially 3 mm, the third predetermined amount comprises substantially 1 mm and the fourth predetermined amount comprises substantially 1 mm.

In Example 16, the subject matter of any one or more of Examples 11-15 optionally can include the at least one of the first plurality of femoral prostheses and the at least one of the second plurality of femoral prostheses are configured to articulate with a same tibial bearing component.

In Example 17, the subject matter of any one or more of Examples 11-16 optionally can include the first posterior condylar offset of at least four of the first plurality of the femoral prostheses is substantially the same as the second posterior condylar offset of at least four of the second plurality of femoral prostheses.

In Example 18, the subject matter of any one or more of Examples 11-17 optionally can include the first posterior condylar offset of at least six of the first plurality of the femoral prostheses is substantially the same as the second posterior condylar offset of at least six of the second plurality of femoral prostheses.

In Example 19, the subject matter of any one or more of Examples 11-18 optionally can include the first femoral medial-lateral condylar extent of at least four of the first plurality of the femoral prostheses is substantially the same as the second femoral medial-lateral condylar extent of at least four of the second plurality of femoral prostheses.

In Example 20, the subject matter of any one or more of Examples 11-19 optionally can include the first femoral medial-lateral condylar extent of at least six of the first plurality of the femoral prostheses is substantially the same as the second femoral medial-lateral condylar extent of at least six of the second plurality of femoral prostheses.

In Example 21, the subject matter of any one or more of Examples 11-20 optionally can include each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

In Example 22, the subject matter of any one or more of Examples 11-21 optionally can include each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

In Example 23, the systems of any one or any combination of Examples 1-22 can optionally be configured such that all elements or options recited are available to use or select from.

These and other examples and features of the present devices and systems will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Figure 1:
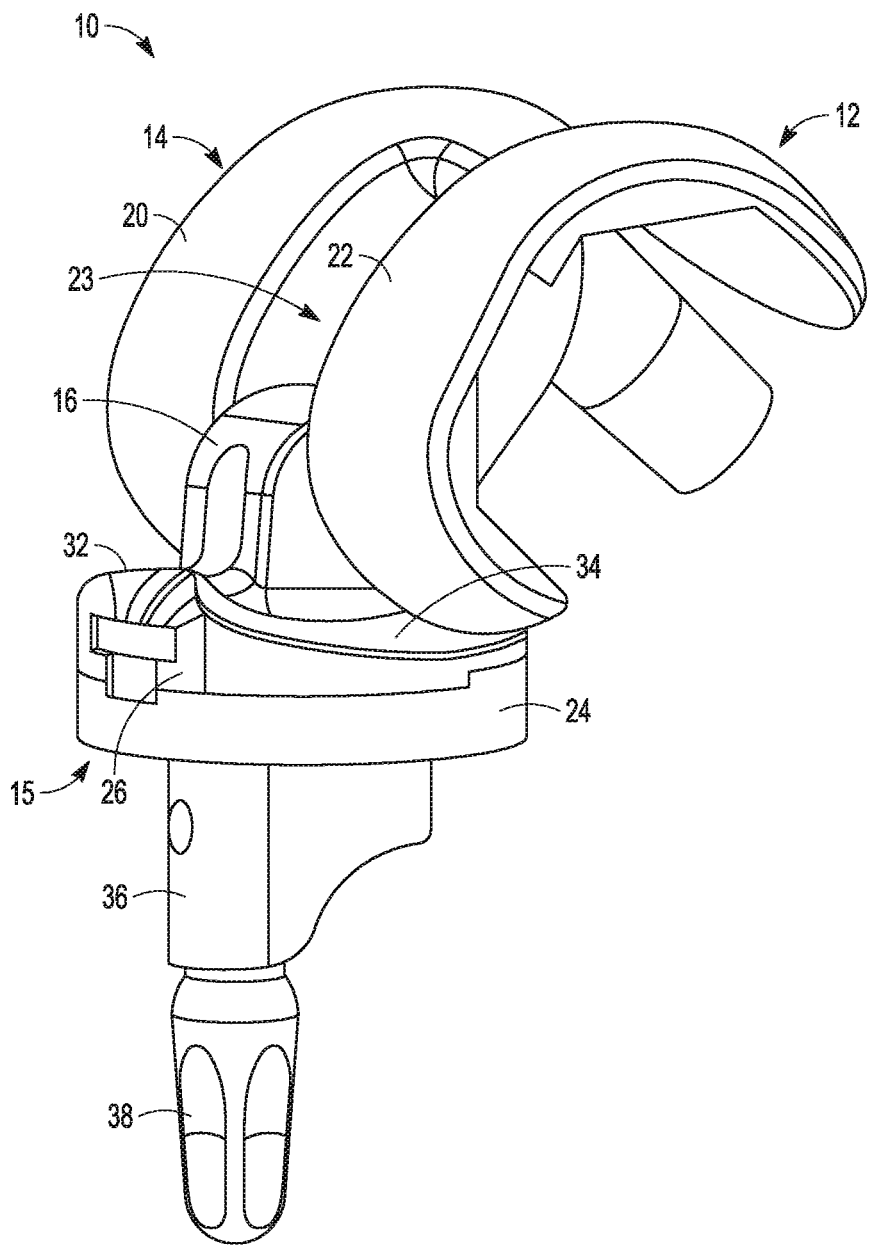
FIG. 1 shows a perspective view of a prosthesis assembly including a femoral prosthesis, a tibial bearing component and a tibial baseplate according to an example of the present application.

The present application relates femoral prostheses and systems. The systems, for example, can include a first family having a first plurality of femoral prostheses with different stock sizes from one another. The system can additional include a second family having a second plurality of femoral prostheses with different stock sizes from one another. Each of the first plurality of femoral prostheses can have a first stem housing extending along a first axis and a first medial condyle and a first lateral condyle coupled to the first stem housing. The first medial condyle and the first lateral condyle can have a first posterior condylar offset as measured from the first axis to a first posterior-most point of the first medial condyle and the first lateral condyle. The first medial condyle and the first lateral condyle can have a first femoral medial-lateral condylar extent as measured from a medial most edge of the first medial condyle to a lateral most edge of the first lateral condyle. Similarly, the second stem housing can extending along a second axis and a second medial condyle and a second lateral condyle can be coupled to the second stem housing. The second medial condyle and the second lateral condyle can have a second posterior condylar offset as measured from the second axis to a second posterior-most point of the second medial condyle and the second lateral condyle. The second medial condyle and the second lateral condyle can have a second femoral medial-lateral condylar extent as measured from a medial most edge of the second medial condyle to a lateral most edge of the second lateral condyle. The first femoral medial-lateral condylar extent of at least one of the first plurality of femoral prostheses and the second femoral medial-lateral condylar extent of at least one of the second plurality of femoral prostheses can be substantially the same according to some examples.

The present application relates to prostheses and systems that can be used in a knee arthroplasty and/or as part of a later knee revision surgery. As described herein, the term system or assembly can include both tibial prosthesis and a femoral prosthesis. This application focuses on aspects of the femoral prosthesis, which can include the stem housing, the medial condyle and the lateral condyle. As discussed previously, the femoral prostheses can be part of the system used to simplify sizing and offer various femoral options that can be compatible with the same tibial bearing component. Additional features and benefits of the various examples provided herein will be discussed and/or will be apparent to one of ordinary skill in the art.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior". Similarly, the term "lateral" refers to the opposite direction of "medial".

Figure 2:
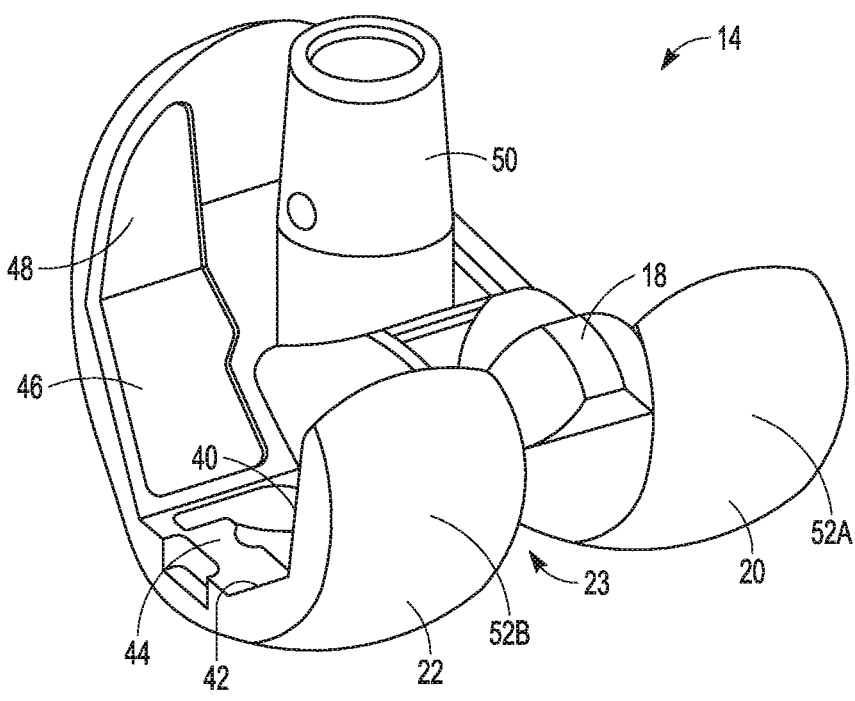
FIG. 2 shows a perspective view of the femoral prosthesis of FIG. 1 according to an example of the present application.
Figure 2A:
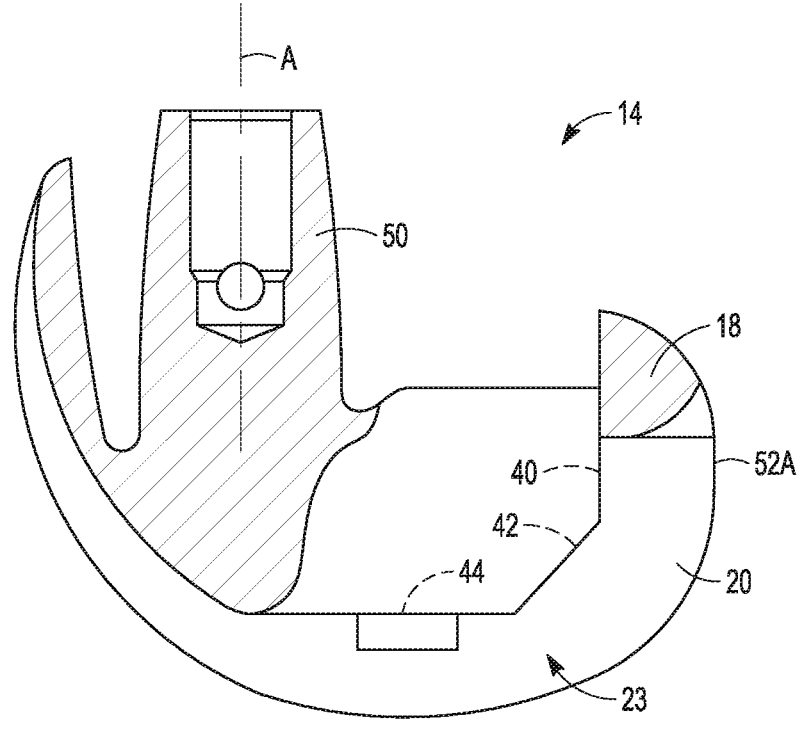
FIG. 2A shows a cross-sectional view of FIG. 2 in a sagittal plane extending through an intercondylar space between a medial condyle and a lateral condyle according to an example of the present application.
Figure 3:
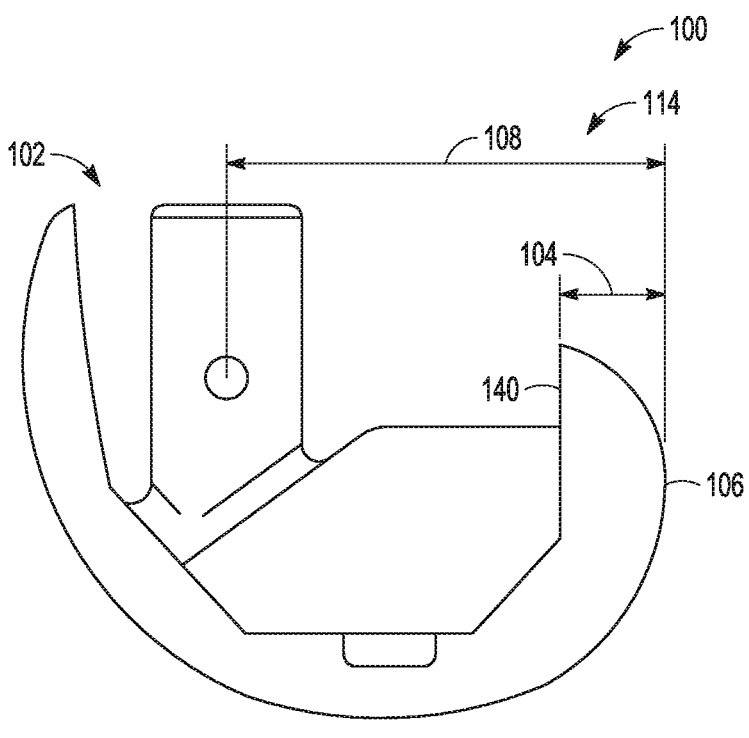
FIGS. 3 and 3A show a system that includes a first femoral prosthesis of a first size from a first family and a second femoral prosthesis from a second family, the second femoral prosthesis of a corresponding size but having an additional thickness in a posterior portion as compared with the first femoral prosthesis according to an example of the present application.
Figure 3A:
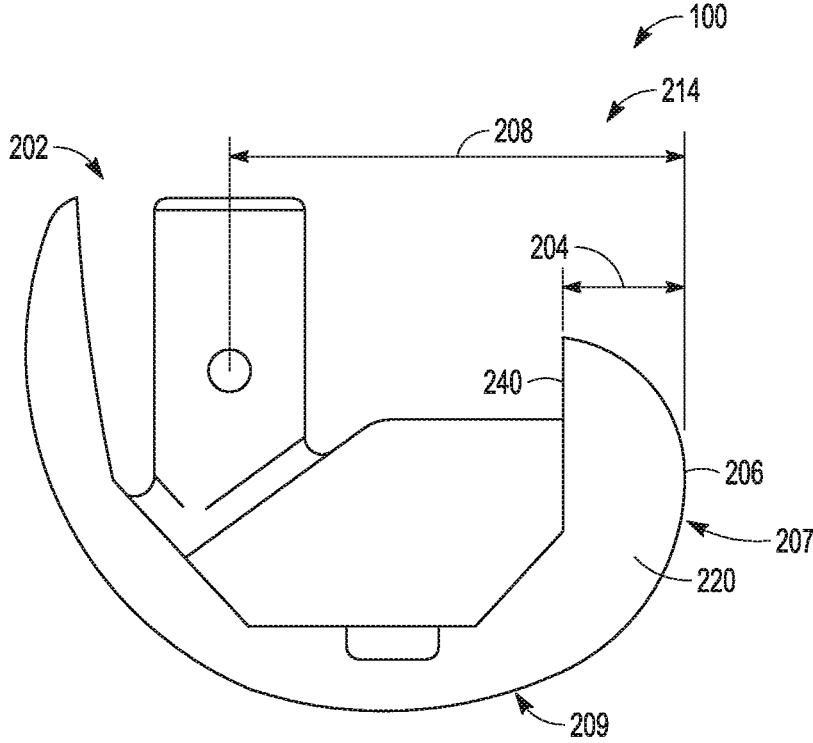

FIG. 1 illustrates a prosthesis assembly 10 that can be used as part of a system 12 described herein. The assembly 10 and system 12 can include a femoral prosthesis 14 and a tibial prosthesis 15. In the example of FIG. 1, the prosthesis assembly 10 is shown in a perspective view with the femoral prosthesis 14 articulated relative to the tibial prosthesis 15 to 1350 of flexion. FIGS. 2A, 3 and 3A show various examples of the femoral prosthesis 14 (sometimes indicated with other reference numbers) in a cross-sectional view along a sagittal plane. The sagittal plane extends along the anterior-posterior direction and the proximal-distal direction of the femoral prosthesis illustrated.

According to the examples provided herein, the prosthesis assembly 10 and system 12 can utilize posterior stabilized (PS) prostheses. Thus, the tibial prosthesis 15 can include a spine 16 and the femoral prosthesis 14 can include a cam 18 (FIGS. 2 and 2A). The spine 16 and the cam 18 can designed to cooperate with one another to stabilize the femoral prosthesis 14 with respect to tibial prosthesis 15 in lieu of a posterior cruciate ligament (PCL). However, other prosthesis designs are contemplated including a mid-level constraint (MLC) design, a cruciate retaining (CR) design, a constrained condylar (CC), an ultra-congruent (UC) design, for example. CR tibial prostheses are generally used in surgical procedures which retain the PCL. The CR and UC designs omit the spine 16 and cam 18. In any case, the femoral prosthesis 14 defines an intercondylar space 23 between medial and lateral condyles 20 and 22 (shown in FIGS. 1 and 2). In the case of a CR or UC, this intercondylar space can entirely open and uninterrupted by the cam 18 as it is in FIGS. 1, 2 and 2A.

Turning to the components illustrated in FIG. 1, the tibial prosthesis 15 can include a tibial bearing component 26 and a tibial baseplate 24. The tibial bearing component 26 can include the spine 16 (FIGS. 2 and 2A), a proximal medial articular surface 32 and a proximal lateral articular surface 34. The tibial baseplate 24 can include a keel 36. Additional components such as a stem 38 can be used with the prosthesis assembly 10 in some examples.

As shown in FIG. 1, the femoral prosthesis 14 can be disposed atop and can articulate relative to the tibial prosthesis 15. Such articulation can be between the medial and lateral femoral condyles 20 and 22 and the proximal medial articular surface 32 and the proximal lateral articular surface 34, respectively. The proximal medial articular surface 32 and the proximal lateral articular surface 34 can be shaped (e.g., curved) to facilitate such articulation during knee joint flexion. The spine 16 (FIGS. 2 and 2A) of the tibial bearing component 26 can be centrally located between the proximal medial articular surface 32 and the proximal lateral articular surface 34. The spine 16 can be configured to engage with the cam 18 during flexion. Such engagement provides additional stability that would otherwise be offered by ligaments such as the PCL.

The tibial bearing component 26 can be secured to the tibial baseplate 24 as shown in FIG. 1. Such securement can be facilitated by the use of rails, notches, bosses, an insert, and/or fastener according to various examples.

FIGS. 2 and 2A show the femoral prosthesis 14. FIG. 2 shows the femoral prosthesis 14 from a posterior-medial position. FIG. 2A shows the femoral prosthesis 14 in a cross-section along the sagittal plane, the cross-section extending along the intercondylar space 23 and bisecting the cam 18.

FIGS. 2 and 2A show the cam 18, which can have multiple radii according to the illustrated example. In addition to the medial and lateral condyles 20 and 22 (only the medial condyle 20 is shown in FIG. 2A), the femoral prosthesis 14 can include a posterior bone-interfacing surface 40 (shown partially dashed in FIG. 2A), a posterior bone-interfacing chamfer surface 42 (shown dashed in FIG. 2A), a distal bone-interfacing surface 44 (shown dashed in FIG. 2A), an anterior bone-interfacing chamfer surface 46 (not shown in FIG. 2A), an anterior bone-interfacing surface 48 (not shown in FIG. 2A) and a stem housing 50. The medial and lateral condyles 20 and 22 can include medial and lateral articular surfaces 52A and 52B, respectively. When viewed in the sagittal plane, (as in FIG. 2A) the articular surfaces 52A and 52B can form J-curves (only one is shown in FIG. 2A).

The cam 18 can be positioned at a posterior end of the intercondylar space 23 and can extend between the medial and lateral condyles 20 and 22. As shown in FIG. 2, portions of the posterior bone-interfacing surface 40, the posterior bone-interfacing chamfer surface 42, the distal bone-interfacing surface 44, the anterior bone-interfacing chamfer surface 46 and the anterior bone-interfacing surface 48 can be formed by the medial and lateral condyles 20 and 22. The medial and lateral articular surfaces 52A and 52B can be disposed opposite (spaced by a thickness of the medial and lateral condyles 20 and 22) from the posterior bone-interfacing surface 40, the posterior bone-interfacing chamfer surface 42, the distal bone-interfacing surface 44, the anterior bone-interfacing chamfer surface 46 and the anterior bone-interfacing surface 48. The medial and lateral condyles 20 and 22 can have varying thicknesses both medial-lateral and anterior-posterior.

The posterior bone-interfacing surface 40, the posterior bone-interfacing chamfer surface 42, the distal bone-interfacing surface 44, the anterior bone-interfacing chamfer surface 46 and the anterior bone-interfacing surface 48 are configured to abut resected portions of the femur (not shown) upon implantation of the femoral prosthesis 14. The stem housing 50 can be positioned generally between the medial and lateral condyles 20 and 22 and can be coupled thereto. The stem housing 50 can be positioned anterior of the intercondylar space 23. The stem housing 50 can extend generally proximally and can be symmetrical about a first axis A as shown in FIG. 2A. In some examples, the stem housing 50 can be canted medial-lateral so as to be both extend medial-lateral and proximal in extent from interconnection between the medial and lateral condyles 20 and 22.

FIGS. 3 and 3A shows examples of femoral prostheses 114, 214 that can be used according to a system 100. The femoral prostheses 114, 214 can be configured in a manner similar to that of the example femoral prosthesis 14 previously described. The femoral prosthesis 114 can be from a first family 102 of femoral prostheses of which the femoral prosthesis 114 is exemplary of one distinct predetermined size. Similarly, the femoral prosthesis 214 can be from a second family 202 of femoral prostheses of which the femoral prosthesis 214 is exemplary of one distinct predetermined size. The femoral prosthesis 114 can be similar in size with respect to the femoral prosthesis 214 according to some examples. Such similarity can be that a medial-lateral condylar extent (shown subsequently) of the femoral prosthesis 114 can be substantially the same as the medial-lateral condylar extent of the femoral prosthesis 214. Thus, according to some examples, the femoral prostheses 114, 214 can be compatible to articulate with the same tibial prosthesis (i.e. the same bearing component) as is discussed further subsequently. The medial-lateral condylar extent is illustrated in reference to FIGS. 4-5C and can comprise a distance from a medial most edge of the medial condyle to a lateral most edge of the lateral condyle.

However, as shown in FIGS. 3 and 3A, the femoral prosthesis 114 can differ in size from the femoral prosthesis 214 in that the femoral prosthesis 214 has a different thickness 204 between at least the posterior bone-interfacing surface 240 and the articular surface 206 than the femoral prosthesis 114. Thus, a thickness 104 between the posterior bone-interfacing surface 140 and the articular surface 106 differs from the thickness 204 as shown in the example of FIGS. 3 and 3A. Thus, for the femoral prosthesis 214, the second medial condyle 220 and the second lateral condyle (only the medial condyle 220 is shown in FIGS. 3 and 3A) are thickened along a posterior portion 207 comprising at least a region between the posterior bone-contacting surface 240 and a posterior portion of the J-curve 209 when viewed in a sagittal plane relative to a corresponding thickness of the first medial condyle and the first lateral condyle of the femoral prosthesis 114.

Due to the difference between the thickness 104 and the thickness 204, the femoral prosthesis 114 can have a posterior condylar offset 108 that differs from a posterior condylar offset 208 of the femoral prosthesis 214. According to some examples, the posterior condylar offset 108 can differ from the posterior condylar offset 208 by a predetermined amount (e.g., 1, 2, 3, 4 or 5 mm). Indeed, in the illustrated embodiment of FIGS. 3 and 3A, the predetermined amount can comprise substantially 3 mm difference between the posterior condylar offset 208 and the posterior condylar offset 108.

Figure 4:
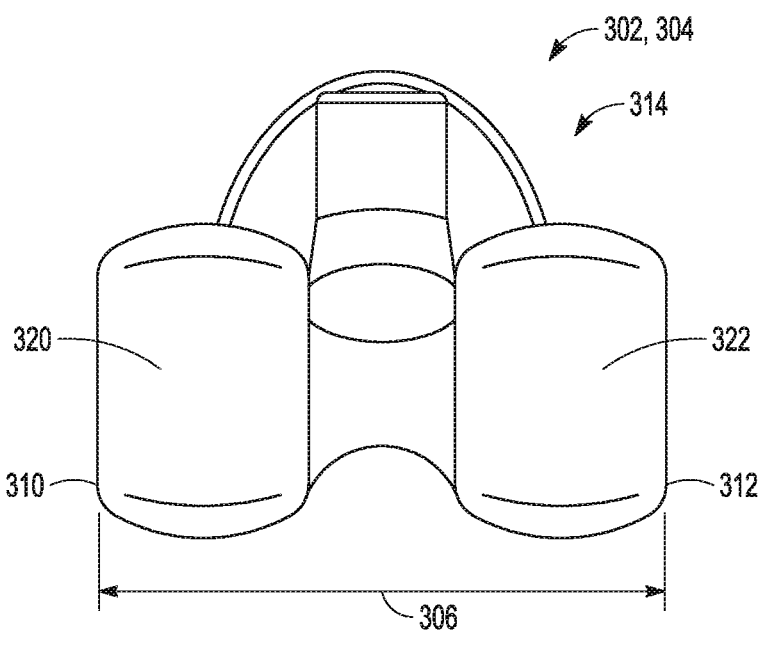
FIGS. 4 and 4A show a femoral prosthesis of either the first family or the second family showing femoral medial-lateral condylar extent and a posterior condylar offset according to an example of the present application.
Figure 4A:
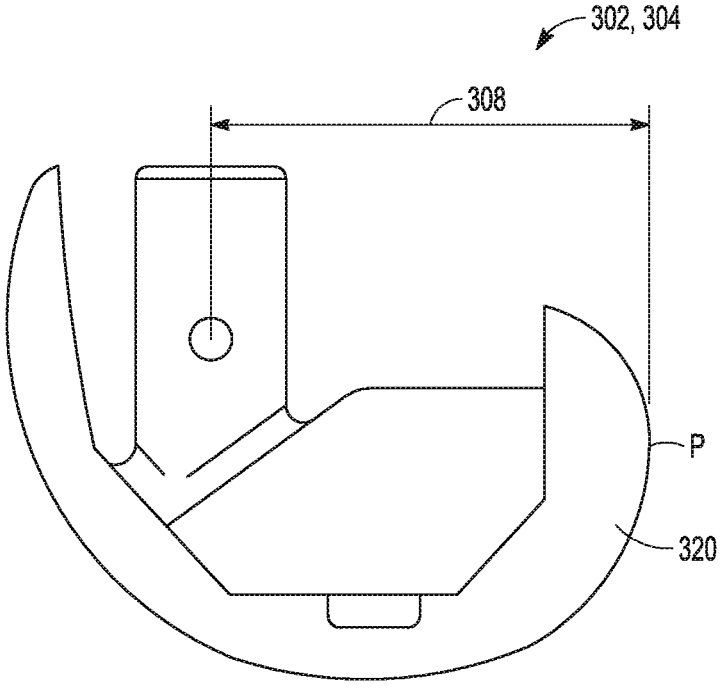

FIGS. 4 and 4A shows a femoral prosthesis 314 that can comprise one of either the first family of femoral prostheses 302 or the second family of femoral prostheses 304 discussed subsequently in regards to FIGS. 5A to 5C. As shown in FIGS. 4 and 4A, the femoral prosthesis 314 can include a medial-lateral condylar extent 306 and a posterior condylar offset 308.

The medial-lateral condylar extent 306 can be from a medial most edge 310 of a medial condyle 320 to a lateral most edge 312 of a lateral condyle 322. The posterior condylar offset 308 can extend from an axis A of a stem housing 314 to a posterior-most point P of at least one of the medial condyle 320 and the lateral condyle 322.

Figure 5A:
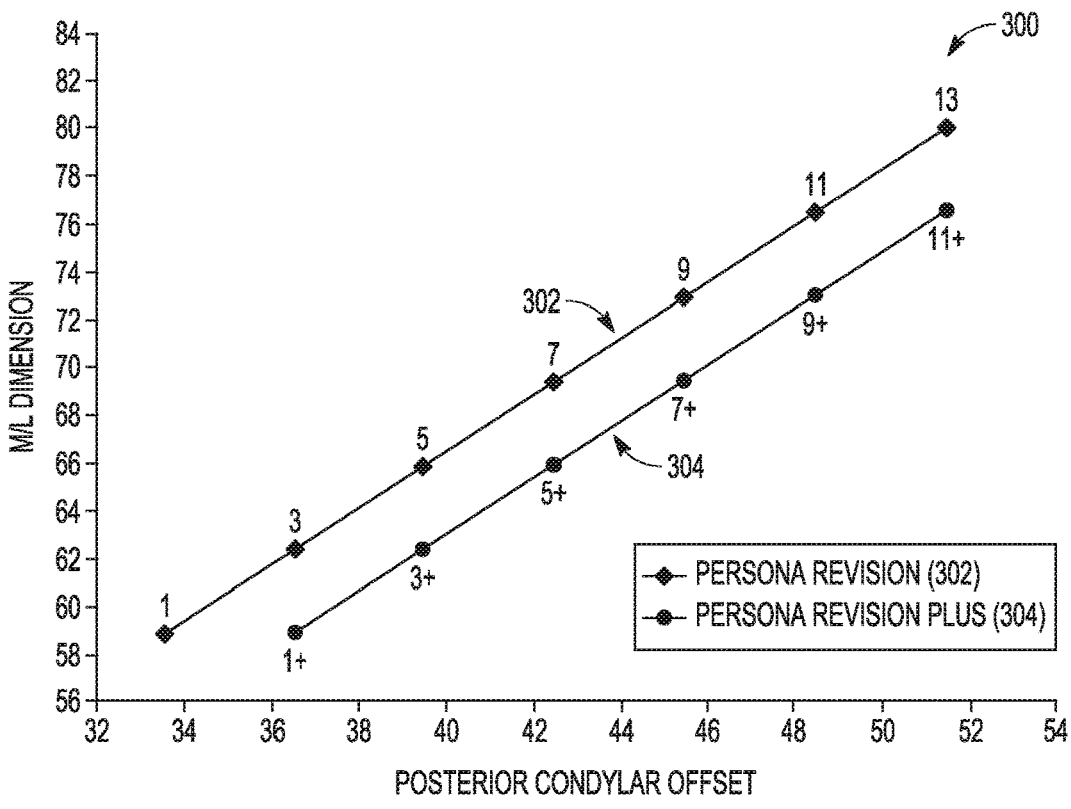
FIG. 5A is a graph of a system of femoral prostheses from the first family and the second family, the graph plotting the difference in sizes of the first family and the second family as measured by the femoral medial-lateral condylar extent and the posterior condylar offset according to an example of the present application.
Figure 5B:
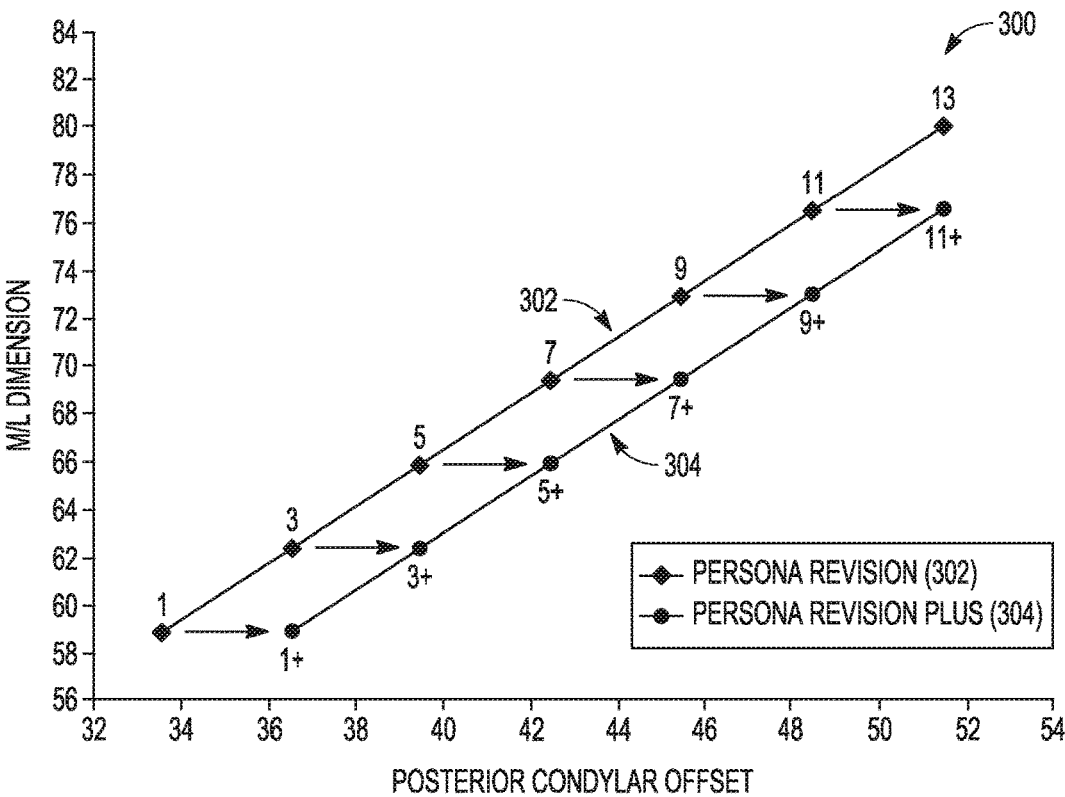
FIG. 5B is the graph of FIG. 5A but shows an upsizing technique whereby a physician can increase the posterior condylar offset while maintaining the femoral medial-lateral condylar extent by swapping a femoral prosthesis of a first size from the first family for a femoral prosthesis of the second family according to an example of the present application.
Figures 5C, 6:
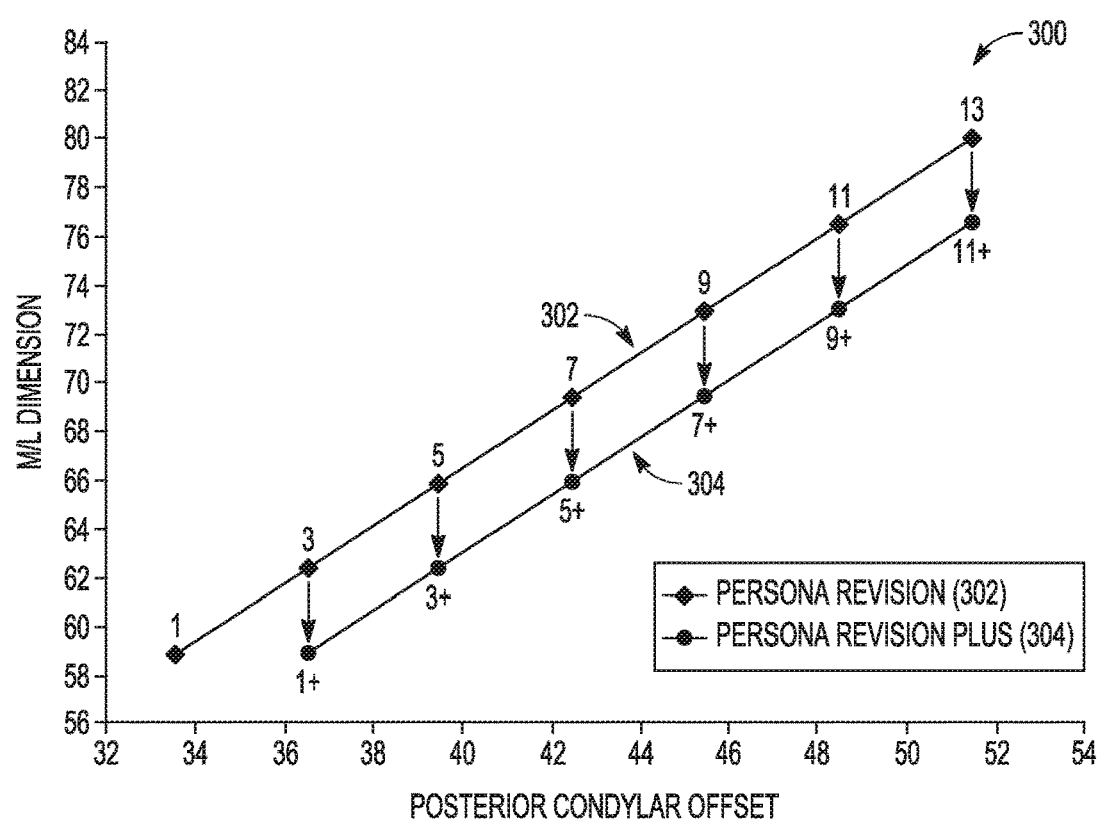
FIG. 5C is the graph of FIG. 5A but shows a downsizing technique whereby the physician can reduce the femoral medial-lateral condylar extent but maintain the posterior condylar offset by swapping a femoral prosthesis of a first size from the first family for a femoral prosthesis of the second family according to an example of the present application.
FIG. 6 shows a sizing chart for a family of tibial bearing components relative to a family of femoral prostheses and tibial baseplates and in accordance with an example of the present application

FIGS. 5A-5C provide a system 300 comprised of the first family of femoral prostheses 302 and the second family of femoral prostheses 304. Each of the first family of femoral prostheses 302 and the second family of femoral prostheses 304 include a plurality of distinct sizes as shown in the plot of FIGS. 5A-5C. In the example of FIGS. 5A-5C, the first family of femoral prostheses 302 can have seven distinct sizes indicated as sizes 1, 3, 5, 7, 9, 11 and 13. The second family of femoral prostheses 304 can have six distinct sizes indicated as sizes 1+, 3+, 5+, 7+, 9+ and 11+.

According to the example of FIG. 5A, the posterior condylar offset of at least four of the first family of femoral prostheses 302 (the first family of femoral prostheses 302 being of different distinct sizes from one another) can be substantially the same as the posterior condylar offset of at least four of the second family of femoral prostheses 304 (the second family of femoral prosthesis 304 being of different distinct sizes from one another). According to some examples, the posterior condylar offset of at least six of the first family of femoral prostheses 302 can be substantially the same as the posterior condylar offset of at least six of the second family of femoral prostheses 304 (e.g., sizes 3 and 1+ can have substantially the same posterior condylar offset, sizes 5 and 3+ can have substantially the same posterior condylar offset, sizes 7 and 5+ can have substantially the same posterior condylar offset, sizes 9 and 7+ can have substantially the same posterior condylar offset, sizes 11 and 9+ can have substantially the same posterior condylar offset and sizes 13 and 11+ can share substantially the same posterior condylar offset).

Similarly, the femoral medial-lateral condylar extent of at least four of the first family of femoral prostheses 302 (the first family of femoral prostheses 302 being of different distinct sizes from one another) can substantially the same as the femoral medial-lateral condylar extent of at least four of the second family of femoral prostheses 304 (the second family of femoral prosthesis 304 being of different distinct sizes from one another). According to some examples, the femoral medial-lateral condylar extent of at least six of the first family of femoral prostheses 302 can be substantially the same as the femoral medial-lateral condylar extent of at least six of the second family of femoral prostheses 304 (e.g., sizes 1 and 1+ can have substantially the same femoral medial-lateral condylar extent, sizes 3 and 3+ can have substantially femoral medial-lateral condylar extent, sizes 5 and 5+ can have substantially the same femoral medial-lateral condylar extent, sizes 7 and 7+ can have substantially the same femoral medial-lateral condylar extent, sizes 9 and 9+ can have substantially the same femoral medial-lateral condylar extent and sizes 11 and 11+ can share substantially the same femoral medial-lateral condylar extent).

As shown in FIGS. 5A and 5B, each of the different stock sizes of the first family of plurality of femoral prostheses 302 can differ with respect to the femoral medial-lateral condylar extent by a first amount (e.g., a few mm such as 3 mm) between a smaller size and a next larger size and each of the different stock sizes. Similarly, the second family of femoral prostheses 304 can differ with respect to the femoral medial-lateral condylar extent by a second amount (e.g., a few mm such as 3 mm) between a corresponding smaller size and a corresponding next larger size. In some cases, the first amount can be substantially the same as the second amount.

FIG. 5B shows that the system 300 can have the first family of femoral prostheses 302 be compatible with the second family of femoral prostheses 304 for a flexion fill. In particular, up to six of the first family of femoral prostheses 302 can be compatible with corresponding sizes of the second family of femoral prostheses 304 such that the posterior condylar offset can be changed by swapping a particular size of prosthesis from the first family of femoral prostheses 302 for a corresponding size of the second family of femoral prostheses 304 (e.g., a size 1 can be swapped for a size 1+, etc.). According to the example of FIG. 5B, the posterior condylar offset can be changed by a predetermined amount (e.g., 3 mm) when swapping a particular size of prosthesis from the first family of femoral prostheses 302 for a corresponding size of the second family of femoral prostheses 304. Furthermore, according to the example of FIG. 5B, while the posterior condylar offset can be changed, the femoral medial-lateral condylar extent between the first size of the first family of femoral prostheses 302 and the correspondingly size of the second family of femoral prostheses 304 can remain substantially the same.

FIG. 5C shows the system 300 can be used for a downsizing in the femoral medial-lateral condylar extent while the flexion fill can be maintained. In particular, up to six of the first family of femoral prostheses 302 can be compatible with other sizes of the second family of femoral prostheses 304 such that the femoral medial-lateral condylar extent can be changed by swapping a particular size of prosthesis from the first family of femoral prostheses 302 for a second size of the second family of femoral prostheses 304 (e.g., a size 3 can be swapped for a size 1+, etc.). According to the example of FIG. 5C, while the femoral medial-lateral condylar extent can be changed, the posterior condylar offset between the first size of the first family of femoral prostheses 302 and the second size of the second family of femoral prostheses 304 can remain substantially the same.

FIG. 6 shows a sizing chart for the family of tibial baseplates 350 relative to the first and second families of femoral prostheses 302, 304. As shown in FIG. 6 the least one of the first family of femoral prostheses 302 and the least one of the second family of femoral prostheses 304 can be configured to articulate with a same tibial bearing component. More particularly, the sizing chart shows the first and second families of femoral prostheses 302, 304 can have at least thirteen different stock sizes 1 to 13 (including+ sizes). As previously discussed and illustrated, each femoral prosthesis of the first and second families can be of a same design class but can include distinct sizes having different femoral medial-lateral condylar extent and/or posterior condylar offset.

The family of tibial baseplates 350 can have at least nine different stock sizes A to J. As shown in FIG. 6, a family of tibial bearing components 352 can be configured such that eleven stock sizes exist and that combinations of the at least nine different stock sizes of the family of tibial baseplates are compatible for operable use (e.g. to facilitate a desired articulation similar to that of a natural knee) with the at least thirteen different stock sizes of the first and second families of femoral prostheses 302, 304.

FIG. 6 also illustrates that at least six of the different stock sizes of tibial bearing components 352 are configured to be are compatible with at least four of the thirteen stock sizes of femoral prostheses while also being compatible with at least two of the tibial components 350.

According to further examples, eleven of the at least thirteen different stock sizes of the first and second families of femoral prostheses 302, 304 can be compatible for operable use with nine of the at least eleven different stock sizes of the family of tibial bearing components 352. According to further examples, twelve of the at least thirteen different stock sizes of the first and second families of femoral prostheses 302, 304 can be compatible for operable use with at least two of the at least eleven different stock sizes of the tibial bearing baseplates 350.

This overlapping sizing and the provision of many different compatible sizes can have benefits including providing for increased stability of the medial condyle of the femoral prosthesis. Additionally, the overlapping sizing allows for the flexion fill and downsizing in the femoral medial-lateral condylar extent as discussed previously with respect to FIGS. 5A-5C.

Figure 7:
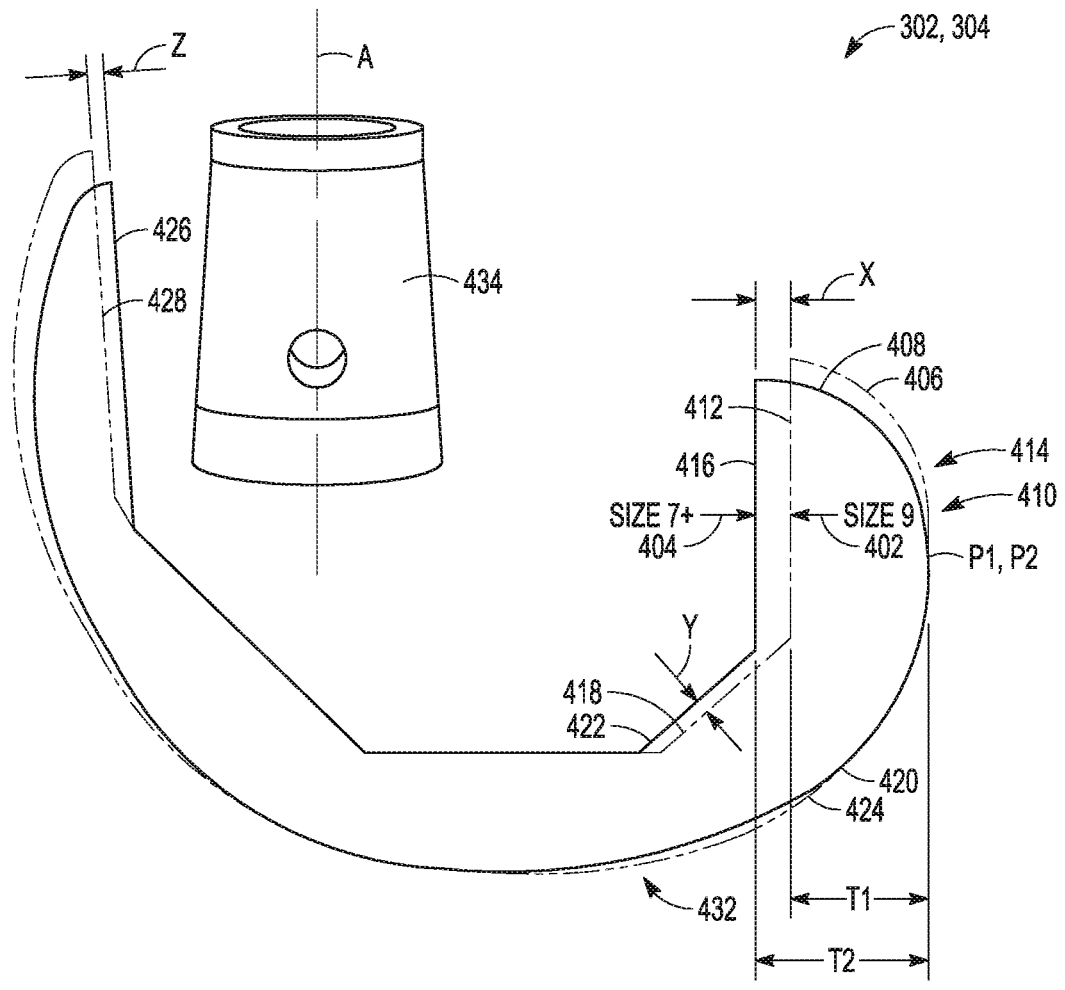
FIG. 7 shows example of the downsizing of FIG. 5C with regard to two juxtapositioned prostheses having substantially a same posterior condylar offset including one femoral prosthesis of the first family and one femoral prosthesis of the second family according to an example of the present application.

FIG. 7 provides a specific example of the downsizing in the femoral medial-lateral condylar extent while the flexion fill (substantially the same posterior condylar offset) can be maintained as previously discussed in reference to FIG. 5C. FIG. 7 shows a geometry of a first prosthesis 402 of a first size (e.g., size 9) of the first family of femoral prostheses 302 in a sagittal plane superimposed on the geometry of a second prosthesis 404 of a second size (e.g., size 7+) of the second family of femoral prostheses 304 in a sagittal plane.

FIG. 7 shows the first prosthesis 402 can include one of a first medial condyle or first lateral condyle (collectively 406). Similarly, the second prosthesis 404 can include one of a second medial condyle or second lateral condyle (collectively 408).

As shown in FIG. 7, at least one of the first medial condyle and the first lateral condyle 406 can have a first thickness T1 at a posterior portion 410 between a first posterior bone-contacting surface 412 and the first posterior-most point P1. Similarly, at least one of the second medial condyle and the second lateral condyle 408 can have a second thickness T2 at a corresponding posterior portion 414 between a second posterior bone-contacting surface 416 and the second posterior-most point P2 (points P1 and P2 can be disposed at a same posterior location). As shown in FIG. 7, according to some examples the first thickness T1 can differ from the second thickness T2 by a predetermined amount (e.g., X as shown in FIG. 7).

According to the example of FIG. 7, a third thickness of at least one of the first medial condyle and the first lateral condyle 406 as measured between a first posterior chamfer 418 and an articular surface 420 of the first prosthesis 402 differs by a predetermined amount Y from a fourth thickness of at least one of the second medial condyle and the second lateral condyle 408 as measured between a corresponding second posterior chamfer 422 and a corresponding articular surface 424 of the second prosthesis 404.

In some examples, an anterior bone-contacting surface 426 of the second prosthesis 404 (one of the second plurality of femoral prostheses 304 previously discussed) can be disposed relatively nearer to a stem housing axis A by another predetermined amount Z than a corresponding anterior bone-contacting surface 428 of the first prosthesis 402 (one of the first plurality of femoral prostheses 302).

As previously discussed, the downsizing in the femoral medial-lateral condylar extent can be by a predetermined amount (e.g., a few mm). Similarly, the predetermined amount X can be substantially 3 mm (or another desired amount), the predetermined amount Y can comprise substantially 1 mm (or another desired amount) and the predetermined amount Z comprises substantially 1 mm (or another desired amount).

At least one of the first medial condyle and the first lateral condyle 406 and at least one of the second medial condyle and the second lateral condyle 408 can have a similar sagittal J-curve 430 along a posterior and distal portion thereof 432 from the first and second posterior-most points P1 and P2, respectively, to a point distal of the stem housing 434, respectively.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for knee arthroplasty comprising:
   a family of femoral components having a plurality of different stock sizes, wherein at least two of the plurality of different stock sizes have a same first dimension but differ in at least a second dimension, each of the family of femoral components including a medial condyle and a lateral condyle; and
   a family of tibial bearing components having a plurality of different stock sizes, each of the tibial bearing components having an articular surface, the articular surface including a medial compartment and a lateral compartment;

wherein at least two of the plurality of different stock sizes of the family of femoral components are compatible for articulation with two of the plurality of different stock sizes of the family of tibial bearing components and a plurality of different stock sizes of a family of tibial components;

wherein the same first dimension comprises a femoral medial-lateral condylar extent as measured from a medial most edge of the medial condyle to a lateral most edge of the lateral condyle;

wherein the at least the second dimension comprises a posterior condylar offset as measured from an axis of a stem housing to a first posterior-most point of one or more of the medial condyle and the lateral condyle.

2. The system of claim 1, wherein at least one of a posterior condylar offset as measured from an axis of a stem housing to a first posterior-most point of one or more of the medial condyle and the lateral condyle or a femoral medial-lateral condylar extent as measured from a medial most edge of the medial condyle to a lateral most edge of the lateral condyle for at least two of the plurality of different stock sizes for the family of femoral components differs by a predetermined amount.

3. The system of claim 1, wherein a two smallest of the plurality of different stock sizes of the family of femoral prostheses and a two smallest of the plurality of different stock sizes of the family of tibial components are compatible with a same stock size of the family of tibial bearing components.

4. The system of claim 1, wherein at least four of the plurality of different stock sizes of the family of femoral components and at least six of the plurality of different stock sizes of the family of tibial components are compatible with three of the plurality of different stock sizes of the family of tibial bearing components.

5. The system of claim 1, wherein each the plurality of different stock sizes of the family of femoral components is compatible for articulation with at least two of the plurality of different stock sizes of the family of tibial bearing components.

6. The system of claim 1, wherein eight of the plurality of different stock sizes of the family of femoral components are compatible for articulation with six of the plurality of different stock sizes of the family of tibial bearing components.

7. The system of claim 1, wherein three out of at least eleven of the plurality of different stock sizes of the family of tibial bearing components are compatible with no more than two of the plurality of different stock sizes of the family of femoral components.

8. The system of claim 1, wherein, for the family of femoral components, at least six pairs of the plurality of different stock sizes have the same first dimension.

9. They system of claim 1, wherein at least a majority of the plurality of different stock sizes of the family of femoral components differ by a predetermined same amount with respect to at least the second dimension as compared with a next larger or next smaller stock size of the plurality of different stock sizes for the family of femoral components.

10. A system for knee arthroplasty comprising:

a family of femoral components having a plurality of different stock sizes, each of the femoral components including a medial condyle and a lateral condyle; and a family of tibial bearing components having a plurality of different stock sizes, each of the tibial bearing components having an articular surface including a medial compartment and a lateral compartment configured for articulation with the medial condyle and the lateral condyle of at least one of the family of femoral components, respectively;

wherein each the plurality of different stock sizes of the family of femoral components is compatible for articulation with at least two of the plurality of different stock sizes of the family of tibial bearing components;

and wherein three out of at least eleven of the plurality of different stock sizes of the family of tibial bearing components are compatible with no more than two of the plurality of different stock sizes of the family of femoral components.

11. The system of claim 10, wherein at least two of the plurality of different stock sizes of the family of femoral components have a same first dimension but differ in at least a second dimension.

12. The system of claim 10, wherein a two smallest of the plurality of different stock sizes of the family of femoral prostheses and a two smallest different stock sizes of a family of tibial components are compatible with a same stock size of the family of tibial bearing components.

13. The system of claim 10, wherein at least four of the plurality of different stock sizes of the family of femoral components and at least six different stock sizes of a family of tibial components are compatible with three of the plurality of different stock sizes of the family of tibial bearing components.

14. The system of claim 10, wherein eight of the plurality of different stock sizes of the family of femoral components are compatible for articulation with six of the plurality of different stock sizes of the family of tibial bearing components.

15. The system of claim 10, wherein at least a majority of the plurality of different stock sizes of the family of femoral prostheses differ by a predetermined same amount with respect to at least a second dimension as compared with a next larger or next smaller stock size of the plurality of different stock sizes of the family of femoral prostheses.

* * * * *